(12) United States Patent
Smith et al.

(10) Patent No.: US 11,478,275 B2
(45) Date of Patent: Oct. 25, 2022

(54) FLEXIBLE FASTENING BAND CONNECTOR

(71) Applicant: Spinal Elements, Inc., Carlsbad, CA (US)

(72) Inventors: Ketchen Smith, Escondido, CA (US); Gregory Martin, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 136 days.

(21) Appl. No.: 15/508,365

(22) PCT Filed: Sep. 16, 2015

(86) PCT No.: PCT/US2015/050441
§ 371 (c)(1),
(2) Date: Mar. 2, 2017

(87) PCT Pub. No.: WO2016/044432
PCT Pub. Date: Mar. 24, 2016

(65) Prior Publication Data
US 2017/0281232 A1    Oct. 5, 2017

Related U.S. Application Data

(60) Provisional application No. 62/051,454, filed on Sep. 17, 2014.

(51) Int. Cl.
*A61B 17/84*    (2006.01)
*A61B 17/62*    (2006.01)
(Continued)

(52) U.S. Cl.
CPC ............ *A61B 17/62* (2013.01); *A61B 17/707* (2013.01); *A61B 17/7053* (2013.01);
(Continued)

(58) Field of Classification Search
CPC ... A61B 17/62; A61B 17/7053; A61B 17/707; A61B 17/82; A61B 17/842
See application file for complete search history.

(56) References Cited

U.S. PATENT DOCUMENTS

| 86,016 A | 1/1869 | Howell |
| 1,630,239 A | 5/1927 | Binkley et al. |

(Continued)

FOREIGN PATENT DOCUMENTS

| CA | 2 437 575 | 4/2009 |
| DE | 93 04 368 | 5/1993 |

(Continued)

OTHER PUBLICATIONS

Sharpe Products, "Metal Round Disks", https://web.archive.org/web/20120705214756/https://shareproducts.com/store/metal-round-disks, as archived Jul. 5, 2017 in 3 pages.

(Continued)

*Primary Examiner* — Samuel S Hanna
(74) *Attorney, Agent, or Firm* — Knobbe, Martens, Olson & Bear, LLP

(57) ABSTRACT

A flexible fastening band connector can comprises a recess to receive a distal end portion of a flexible fastening band and lumen to receive the proximal end portion of the flexible fastening band. The lumen guides the proximal end portion of the flexible fastening band toward a fastening mechanism. The flexible fastening band connector can comprise an opening to receive a spinal rod. In operation, the spinal rod is coupled to additional devices to secure the spinal rod to portions of one or more vertebra. In some embodiments, a method of performing an operation, e.g. a spinal operation, on a patient using the disclosed connector is provided.

14 Claims, 27 Drawing Sheets

(51) Int. Cl.
    *A61B 17/70* (2006.01)
    *A61B 17/82* (2006.01)
(52) U.S. Cl.
    CPC ...... *A61B 17/7056* (2013.01); *A61B 17/7067* (2013.01); *A61B 17/82* (2013.01); *A61B 17/84* (2013.01); *A61B 17/842* (2013.01)

(56) References Cited

U.S. PATENT DOCUMENTS

| | | |
|---|---|---|
| 1,822,280 A | 9/1931 | Ervay |
| 1,822,330 A | 9/1931 | Anslie |
| 2,486,303 A | 10/1949 | Longfellow |
| 2,706,023 A | 4/1955 | Merritt |
| 2,967,282 A | 1/1961 | Schwartz et al. |
| 3,111,945 A | 11/1963 | Von Solbrig |
| 3,149,808 A | 9/1964 | Weckesser |
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,164,793 A | 8/1979 | Swanson |
| 4,166,292 A | 9/1979 | Bokros |
| 4,231,121 A | 11/1980 | Lewis |
| D261,935 S | 11/1981 | Halloran |
| 4,312,337 A | 1/1982 | Donohue |
| 4,323,217 A | 4/1982 | Dochterman |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,570,618 A | 2/1986 | Wu |
| 4,573,458 A | 3/1986 | Lower |
| 4,573,459 A | 3/1986 | Litton |
| 4,634,445 A | 1/1987 | Helal |
| 4,643,178 A | 2/1987 | Nastari et al. |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,880,429 A | 11/1989 | Stone |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,955,913 A | 9/1990 | Robinson |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,092,868 A | 3/1992 | Mehdian |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,404 A | 9/1992 | Downey |
| 5,171,280 A | 12/1992 | Baumgartner |
| 5,192,326 A | 3/1993 | Bao et al. |
| 5,192,327 A | 3/1993 | Brantigan |
| 5,209,755 A | 5/1993 | Abrahan et al. |
| 5,258,031 A | 11/1993 | Salib et al. |
| 5,282,861 A | 2/1994 | Kaplan |
| 5,286,249 A | 2/1994 | Thibodaux |
| 5,300,073 A | 4/1994 | Ray et al. |
| 5,304,178 A | 4/1994 | Stahurski |
| 5,306,275 A | 4/1994 | Bryan |
| 5,306,308 A | 4/1994 | Gross et al. |
| 5,306,309 A | 4/1994 | Wagner et al. |
| 5,326,364 A | 7/1994 | Clift, Jr. et al. |
| 5,330,479 A | 7/1994 | Whitmore |
| 5,360,431 A | 11/1994 | Puno et al. |
| 5,368,596 A | 11/1994 | Burkhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,142 A | 3/1996 | Fodor et al. |
| 5,496,318 A | 3/1996 | Howland et al. |
| 5,507,823 A | 4/1996 | Walston et al. |
| 5,509,918 A | 4/1996 | Romano |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,698 A | 7/1996 | Preissman |
| 5,540,703 A | 7/1996 | Barker, Jr. et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,716,415 A | 2/1998 | Steffee |
| 5,725,582 A | 3/1998 | Bevan et al. |
| 5,741,260 A | 4/1998 | Songer et al. |
| 5,741,261 A | 4/1998 | Moskovitz et al. |
| D395,138 S | 6/1998 | Ohata |
| 5,766,251 A | 6/1998 | Koshino |
| 5,766,253 A | 6/1998 | Brosnahan |
| 5,772,663 A | 6/1998 | Whiteside et al. |
| 5,797,916 A | 8/1998 | McDowell |

(56) References Cited

U.S. PATENT DOCUMENTS

| | | |
|---|---|---|
| 5,810,854 A | 9/1998 | Beach |
| 5,824,093 A | 10/1998 | Ray et al. |
| 5,824,094 A | 10/1998 | Serhan et al. |
| 5,836,948 A | 11/1998 | Zucherman et al. |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Breard et al. |
| 5,918,604 A | 7/1999 | Whelan |
| 5,951,555 A | 9/1999 | Rehak et al. |
| 5,964,765 A | 10/1999 | Fenton et al. |
| 5,993,452 A | 11/1999 | Vandewalle |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,768 A | 2/2000 | Wenstrom, Jr. et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,099,531 A | 8/2000 | Bonutti |
| 6,102,347 A | 8/2000 | Benoit |
| 6,106,558 A | 8/2000 | Picha |
| 6,113,637 A | 9/2000 | Gill et al. |
| 6,132,464 A | 10/2000 | Martin |
| 6,132,465 A | 10/2000 | Ray et al. |
| 6,146,422 A | 11/2000 | Lawson |
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,325,803 B1 | 12/2001 | Schumacher et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| 6,409,765 B1 | 6/2002 | Bianchi et al. |
| D460,188 S | 7/2002 | Michelson |
| D460,189 S | 7/2002 | Michelson |
| 6,419,678 B1 | 7/2002 | Asfora |
| 6,419,703 B1 | 7/2002 | Fallin et al. |
| 6,423,071 B1 | 7/2002 | Lawson |
| 6,436,099 B1 | 8/2002 | Drewry et al. |
| 6,436,101 B1 | 8/2002 | Hamada et al. |
| 6,436,146 B1 | 8/2002 | Hassler et al. |
| D463,560 S | 9/2002 | Michelson |
| 6,447,544 B1 | 9/2002 | Michelson |
| 6,470,207 B1 | 10/2002 | Simon et al. |
| 6,475,220 B1 | 11/2002 | Whiteside |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |
| 6,607,530 B1 | 8/2003 | Carl et al. |
| 6,610,091 B1 | 8/2003 | Reiley |
| D479,331 S | 9/2003 | Pike et al. |
| 6,626,944 B1 | 9/2003 | Taylor |
| 6,641,614 B1 | 11/2003 | Wagner et al. |
| 6,656,178 B1 | 12/2003 | Veldhuizen et al. |
| 6,656,195 B2 | 12/2003 | Peters et al. |
| 6,669,697 B1 | 12/2003 | Pisharodi |
| 6,669,729 B2 | 12/2003 | Chin |
| 6,679,914 B1 | 1/2004 | Gabbay |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,802,863 B2 | 10/2004 | Lawson et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| 7,004,971 B2 | 2/2006 | Serhan et al. |
| D517,404 S | 3/2006 | Schluter |
| 7,008,429 B2 | 3/2006 | Golobek |
| 7,013,675 B2 | 3/2006 | Marquez-Pickering |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Liao |
| 7,371,238 B2 | 5/2008 | Sololeski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,585,300 B2 | 9/2009 | Cha |
| 7,608,104 B2 | 10/2009 | Yuan et al. |
| 7,695,472 B2 | 4/2010 | Young |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 | 1/2011 | Lim et al. |
| 7,935,136 B2 | 5/2011 | Alamin et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,109,971 B2 | 2/2012 | Hale |
| 8,133,225 B2 | 3/2012 | Pieske |
| 8,163,016 B2 | 4/2012 | Linares |
| 8,172,877 B2 | 5/2012 | Winslow et al. |
| 8,177,810 B2 | 5/2012 | Ferree |
| 8,192,468 B2 | 6/2012 | Biedermann et al. |
| 8,216,275 B2 | 7/2012 | Fielding et al. |
| 8,231,661 B2 | 7/2012 | Carls |
| 8,246,655 B2 | 8/2012 | Jackson et al. |
| 8,267,966 B2 | 9/2012 | McCormack et al. |
| 8,292,954 B2 | 10/2012 | Robinson et al. |
| 8,306,307 B2 | 11/2012 | Koike et al. |
| 8,382,801 B2 | 2/2013 | Lamborne et al. |
| 8,394,125 B2 | 3/2013 | Assell |
| 8,460,346 B2 | 6/2013 | Ralph et al. |
| 8,486,078 B2 | 7/2013 | Carl et al. |
| 8,496,691 B2 | 7/2013 | Blain |
| 8,579,903 B2 | 11/2013 | Carl |
| 8,652,137 B2 | 2/2014 | Blain et al. |
| 8,740,942 B2 | 6/2014 | Blain |
| 8,740,949 B2 | 6/2014 | Blain |
| 8,753,345 B2 | 6/2014 | McCormack et al. |
| 8,784,423 B2 | 7/2014 | Kowarsch et al. |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |

(56) References Cited

U.S. PATENT DOCUMENTS

| | | |
|---|---|---|
| 9,060,787 B2 | 6/2015 | Blain et al. |
| 9,101,410 B1 | 8/2015 | Urrea |
| D739,935 S | 9/2015 | Blain et al. |
| 9,149,283 B2 | 10/2015 | Assell et al. |
| 9,161,763 B2 | 10/2015 | Assell et al. |
| 9,179,943 B2 | 11/2015 | Blain |
| 9,220,547 B2 | 12/2015 | Blain et al. |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 9,345,488 B2 | 5/2016 | Assell et al. |
| 9,421,044 B2 | 8/2016 | Blain et al. |
| D765,853 S | 9/2016 | Blain et al. |
| D765,854 S | 9/2016 | Blain et al. |
| 9,439,686 B2 | 9/2016 | Rooney et al. |
| 9,456,855 B2 | 10/2016 | Blain et al. |
| 9,517,077 B2 | 12/2016 | Blain et al. |
| D777,921 S | 1/2017 | Blain et al. |
| D780,315 S | 2/2017 | Blain et al. |
| 9,572,602 B2 | 2/2017 | Blain et al. |
| 9,615,861 B2 | 4/2017 | Perez-Cruet et al. |
| D790,062 S | 6/2017 | Blain et al. |
| 9,675,387 B2 | 6/2017 | Blain |
| 9,743,937 B2 | 8/2017 | Blain et al. |
| 9,808,294 B2 | 11/2017 | Blain |
| 9,820,784 B2 | 11/2017 | Blain et al. |
| 9,839,450 B2 | 12/2017 | Blain et al. |
| D810,942 S | 2/2018 | Blain et al. |
| D812,754 S | 3/2018 | Blain et al. |
| 9,936,984 B2 | 4/2018 | Blain |
| 10,022,161 B2 | 7/2018 | Blain |
| 10,085,776 B2 | 10/2018 | Blain |
| D834,194 S | 11/2018 | Blain et al. |
| 10,194,955 B2 | 2/2019 | Blain et al. |
| 10,251,679 B2 | 4/2019 | Blain et al. |
| D857,900 S | 8/2019 | Blain et al. |
| 10,368,921 B2 | 8/2019 | Blain |
| 10,426,524 B2 | 10/2019 | Blain |
| 10,624,680 B2 | 4/2020 | Blain |
| D884,896 S | 5/2020 | Blain et al. |
| 10,758,361 B2 | 9/2020 | Blain |
| D926,982 S | 8/2021 | Blain et al. |
| 11,272,961 B2 | 3/2022 | Blain et al. |
| 11,304,733 B2 | 4/2022 | Blain et al. |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0099444 A1 | 7/2002 | Boyd et al. |
| 2002/0120335 A1 | 8/2002 | Angelucci et al. |
| 2002/0123806 A1 | 9/2002 | Reiley |
| 2002/0138077 A1 | 9/2002 | Ferree |
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |
| 2002/0198527 A1 | 12/2002 | Muckter |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0093152 A1 | 5/2003 | Pedersen et al. |
| 2003/0093154 A1 | 5/2003 | Estes et al. |
| 2003/0120343 A1 | 6/2003 | Whelan |
| 2003/0176919 A1 | 9/2003 | Schmieding |
| 2003/0176922 A1 | 9/2003 | Lawson et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1* | 5/2004 | Allen ................. A61B 17/82 606/74 |
| 2004/0116927 A1 | 6/2004 | Graf |
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0195727 A1 | 10/2004 | Stoy |
| 2004/0199166 A1 | 10/2004 | Schmieding et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0107879 A1 | 5/2005 | Christensen et al. |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0154463 A1 | 7/2005 | Trieu |
| 2005/0159746 A1 | 7/2005 | Grab et al. |
| 2005/0171547 A1 | 8/2005 | Aram |
| 2005/0197700 A1 | 9/2005 | Boehm et al. |
| 2005/0204515 A1 | 9/2005 | Hewes |
| 2005/0216017 A1 | 9/2005 | Fielding et al. |
| 2005/0240201 A1 | 10/2005 | Yeung |
| 2005/0251256 A1 | 11/2005 | Reiley |
| 2005/0256494 A1 | 11/2005 | Datta |
| 2006/0004367 A1 | 1/2006 | Alamin et al. |
| 2006/0036323 A1 | 2/2006 | Carl et al. |
| 2006/0041311 A1 | 2/2006 | McLeer |
| 2006/0084985 A1 | 4/2006 | Kim |
| 2006/0085006 A1 | 4/2006 | Ek et al. |
| 2006/0085072 A1 | 4/2006 | Funk et al. |
| 2006/0111782 A1 | 5/2006 | Petersen |
| 2006/0116684 A1 | 6/2006 | Whelan |
| 2006/0149289 A1 | 7/2006 | Winslow et al. |
| 2006/0149375 A1 | 7/2006 | Yuan et al. |
| 2006/0190081 A1 | 8/2006 | Kraus et al. |
| 2006/0200137 A1 | 9/2006 | Soboleski et al. |
| 2006/0241597 A1 | 10/2006 | Mitchell et al. |
| 2006/0241601 A1 | 10/2006 | Trautwein et al. |
| 2006/0241758 A1 | 10/2006 | Peterman et al. |
| 2006/0241778 A1 | 10/2006 | Ogilvie |
| 2006/0247650 A1 | 11/2006 | Yerby et al. |
| 2006/0293691 A1 | 12/2006 | Mitra et al. |
| 2007/0055236 A1 | 3/2007 | Hudgins et al. |
| 2007/0055252 A1 | 3/2007 | Blain et al. |
| 2007/0055373 A1 | 3/2007 | Hudgins et al. |
| 2007/0073293 A1 | 3/2007 | Martz et al. |
| 2007/0078464 A1 | 4/2007 | Jones et al. |
| 2007/0100452 A1 | 5/2007 | Prosser |
| 2007/0118218 A1 | 5/2007 | Hooper |
| 2007/0123863 A1 | 5/2007 | Winslow et al. |
| 2007/0135814 A1 | 6/2007 | Farris |
| 2007/0149976 A1 | 6/2007 | Hale et al. |
| 2007/0179619 A1 | 8/2007 | Grab |
| 2007/0250166 A1 | 10/2007 | McKay |
| 2007/0255414 A1 | 11/2007 | Melkent et al. |
| 2007/0270812 A1 | 11/2007 | Peckham |

(56) References Cited

U.S. PATENT DOCUMENTS

| | | |
|---|---|---|
| 2008/0009866 A1 | 1/2008 | Alamin et al. |
| 2008/0046083 A1 | 2/2008 | Hewko |
| 2008/0058929 A1 | 3/2008 | Whelan |
| 2008/0082103 A1 | 4/2008 | Hutton et al. |
| 2008/0082172 A1 | 4/2008 | Jackson |
| 2008/0161853 A1 | 7/2008 | Arnold et al. |
| 2008/0177264 A1 | 7/2008 | Alamin et al. |
| 2008/0177326 A1 | 7/2008 | Thompson |
| 2008/0183209 A1 | 7/2008 | Robinson et al. |
| 2008/0183211 A1 | 7/2008 | Lamborne et al. |
| 2008/0228225 A1 | 9/2008 | Trautwein et al. |
| 2008/0255664 A1 | 10/2008 | Hogendijk et al. |
| 2008/0262549 A1 | 10/2008 | Bennett et al. |
| 2008/0287996 A1 | 11/2008 | Soholeski et al. |
| 2009/0005818 A1 | 1/2009 | Chin et al. |
| 2009/0005873 A1 | 1/2009 | Slivka et al. |
| 2009/0018662 A1 | 1/2009 | Pasquet et al. |
| 2009/0024166 A1 | 1/2009 | Carl et al. |
| 2009/0036926 A1 | 2/2009 | Hestad |
| 2009/0072006 A1 | 3/2009 | Clauson et al. |
| 2009/0076617 A1 | 3/2009 | Ralph et al. |
| 2009/0105766 A1 | 4/2009 | Thompson et al. |
| 2009/0125066 A1 | 5/2009 | Kraus et al. |
| 2009/0138048 A1 | 5/2009 | Baccelli et al. |
| 2009/0171360 A1 | 7/2009 | Whelan |
| 2009/0198282 A1 | 8/2009 | Fielding et al. |
| 2009/0198339 A1 | 8/2009 | Kleiner et al. |
| 2009/0248077 A1* | 10/2009 | Johns ................ A61B 17/7011 606/246 |
| 2009/0248082 A1 | 10/2009 | Crook et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2009/0270929 A1 | 10/2009 | Suddaby |
| 2009/0306716 A1 | 12/2009 | Beger et al. |
| 2009/0326589 A1 | 12/2009 | Lemoine et al. |
| 2010/0004657 A1 | 1/2010 | Dudasik |
| 2010/0010548 A1 | 1/2010 | Hermida Ochoa |
| 2010/0063550 A1 | 3/2010 | Felix et al. |
| 2010/0076503 A1 | 3/2010 | Beyar et al. |
| 2010/0087859 A1 | 4/2010 | Jackson, Jr. |
| 2010/0131008 A1 | 5/2010 | Overes et al. |
| 2010/0168864 A1 | 7/2010 | White et al. |
| 2010/0179553 A1 | 7/2010 | Ralph et al. |
| 2010/0185241 A1 | 7/2010 | Malandain et al. |
| 2010/0191286 A1 | 7/2010 | Butler |
| 2010/0204700 A1 | 8/2010 | Falahee |
| 2010/0204732 A1 | 8/2010 | Aschmann et al. |
| 2010/0234894 A1 | 9/2010 | Alamin et al. |
| 2010/0256680 A1 | 10/2010 | Pasquet et al. |
| 2010/0274289 A1* | 10/2010 | Carls .................... A61B 17/842 606/263 |
| 2010/0292698 A1 | 11/2010 | Hulliger et al. |
| 2010/0298829 A1 | 11/2010 | Schaller et al. |
| 2010/0318133 A1 | 12/2010 | Tornier |
| 2011/0015744 A1 | 1/2011 | Squires et al. |
| 2011/0022050 A1 | 1/2011 | McClellan et al. |
| 2011/0022089 A1 | 1/2011 | Assell et al. |
| 2011/0034956 A1* | 2/2011 | Mazda ............... A61B 17/7041 606/278 |
| 2011/0060366 A1 | 3/2011 | Heim et al. |
| 2011/0082504 A1 | 4/2011 | Singhatat et al. |
| 2011/0098816 A1 | 4/2011 | Jacob et al. |
| 2011/0106163 A1 | 5/2011 | Hochschuler et al. |
| 2011/0106259 A1 | 5/2011 | Lindenmann et al. |
| 2011/0160772 A1 | 6/2011 | Arcenio et al. |
| 2011/0172712 A1 | 7/2011 | Chee et al. |
| 2011/0245875 A1 | 10/2011 | Karim |
| 2011/0295318 A1 | 12/2011 | Alamin et al. |
| 2011/0301644 A1* | 12/2011 | Belliard ............. A61B 17/7008 606/263 |
| 2012/0022591 A1* | 1/2012 | Baccelli ............. A61B 17/7053 606/263 |
| 2012/0022649 A1 | 1/2012 | Robinson et al. |
| 2012/0035658 A1 | 2/2012 | Goble et al. |
| 2012/0041441 A1 | 2/2012 | Bernstein et al. |
| 2012/0046749 A1 | 2/2012 | Tatsumi |
| 2012/0101502 A1 | 4/2012 | Kartalian et al. |
| 2012/0150231 A1 | 6/2012 | Alamin et al. |
| 2012/0221060 A1 | 8/2012 | Blain |
| 2012/0245586 A1 | 9/2012 | Lehenkari et al. |
| 2012/0271354 A1 | 10/2012 | Baccelli et al. |
| 2012/0277801 A1 | 11/2012 | Marik et al. |
| 2013/0023878 A1 | 1/2013 | Belliard et al. |
| 2013/0041410 A1 | 2/2013 | Hestad et al. |
| 2013/0079778 A1 | 3/2013 | Azuero et al. |
| 2013/0123923 A1 | 5/2013 | Pavlov et al. |
| 2013/0197643 A1 | 8/2013 | Greenberg et al. |
| 2013/0204250 A1 | 8/2013 | McDevitt et al. |
| 2013/0253649 A1 | 9/2013 | Davis |
| 2013/0261625 A1* | 10/2013 | Koch .................. A61B 17/1691 606/74 |
| 2013/0325065 A1 | 12/2013 | Malandain et al. |
| 2014/0012318 A1 | 1/2014 | Goel |
| 2014/0018816 A1 | 1/2014 | Fenn et al. |
| 2014/0066758 A1 | 3/2014 | Marik et al. |
| 2014/0214084 A1 | 7/2014 | Jackson et al. |
| 2014/0228883 A1 | 8/2014 | Blain |
| 2014/0257397 A1* | 9/2014 | Akbarnia ........... A61B 17/8869 606/263 |
| 2014/0277142 A1 | 9/2014 | Blain |
| 2014/0277149 A1 | 9/2014 | Rooney et al. |
| 2014/0309699 A1* | 10/2014 | Houff .................. A61B 17/823 606/281 |
| 2014/0336653 A1 | 11/2014 | Bromer |
| 2014/0378976 A1 | 12/2014 | Garcia |
| 2015/0045794 A1* | 2/2015 | Garcia ............... A61B 17/8076 606/74 |
| 2015/0081023 A1 | 3/2015 | Blain |
| 2015/0094766 A1 | 4/2015 | Blain et al. |
| 2015/0119988 A1 | 4/2015 | Assell et al. |
| 2015/0164652 A1 | 6/2015 | Assell et al. |
| 2015/0190149 A1 | 7/2015 | Assell et al. |
| 2015/0196330 A1 | 7/2015 | Blain |
| 2015/0209096 A1 | 7/2015 | Gephart |
| 2015/0257773 A1 | 9/2015 | Blain |
| 2015/0313656 A1 | 11/2015 | Hulliger |
| 2015/0327872 A1 | 11/2015 | Assell et al. |
| 2015/0342648 A1 | 12/2015 | McCormack et al. |
| 2015/0342657 A1 | 12/2015 | Voisard et al. |
| 2016/0051294 A1 | 2/2016 | Blain |
| 2016/0113692 A1 | 4/2016 | Knoepfle |
| 2016/0128838 A1 | 5/2016 | Assell et al. |
| 2016/0213481 A1 | 7/2016 | Blain |
| 2016/0324549 A1 | 11/2016 | Blain |
| 2017/0000527 A1 | 1/2017 | Blain et al. |
| 2017/0105767 A1 | 4/2017 | Blain |
| 2017/0239060 A1 | 8/2017 | Blain |
| 2017/0296234 A1 | 10/2017 | Jackson et al. |
| 2017/0333091 A1 | 11/2017 | Taber et al. |
| 2017/0333205 A1 | 11/2017 | Joly et al. |
| 2018/0049780 A1 | 2/2018 | Blain |
| 2018/0085148 A1 | 3/2018 | Blain |
| 2018/0085149 A1 | 3/2018 | Blain |
| 2018/0132915 A1 | 5/2018 | Esser et al. |
| 2019/0142478 A1 | 5/2019 | Blain |
| 2019/0167314 A1 | 6/2019 | Mosnier et al. |
| 2019/0192194 A1 | 6/2019 | Blain |
| 2019/0328428 A1 | 10/2019 | Blain |
| 2019/0365433 A1 | 12/2019 | Blain et al. |
| 2020/0000608 A1 | 1/2020 | Bullard et al. |
| 2020/0214746 A1 | 7/2020 | Blain et al. |
| 2020/0367945 A1 | 11/2020 | Semingson et al. |
| 2021/0000608 A1 | 1/2021 | Blain et al. |
| 2021/0121207 A1 | 4/2021 | Semingson |
| 2021/0251667 A1 | 8/2021 | Blain et al. |

(56) References Cited

U.S. PATENT DOCUMENTS

2022/0151659 A1   5/2022   Smith et al.
2022/0175424 A1   6/2022   Blain et al.

FOREIGN PATENT DOCUMENTS

| | | |
|---|---|---|
| DE | 201 12 123 | 9/2001 |
| DE | 101 35 771 | 2/2003 |
| EP | 0 238 219 | 9/1987 |
| EP | 0 322 334 | 6/1989 |
| EP | 0 392 124 | 10/1990 |
| EP | 0 610 837 | 8/1994 |
| EP | 0 928 603 | 7/1999 |
| EP | 1 201 202 | 5/2002 |
| EP | 1 201 256 | 5/2002 |
| EP | 2 138 122 | 12/2009 |
| EP | 2 813 190 | 12/2014 |
| EP | 2 919 717 | 9/2015 |
| FR | 2 704 745 | 11/1994 |
| FR | 2 722 980 | 2/1996 |
| GB | 2 366 736 | 3/2002 |
| JP | 53-005889 | 1/1978 |
| JP | 62-270147 | 11/1987 |
| JP | 03-100154 | 4/1991 |
| JP | 03-240660 | 10/1991 |
| JP | 08-509918 | 10/1996 |
| JP | 10-179622 | 7/1998 |
| JP | 2000-201941 | 7/2000 |
| JP | 2000-210297 | 8/2000 |
| JP | 2003-079649 | 3/2003 |
| JP | 2004-508888 | 3/2004 |
| JP | 2004-181236 | 7/2004 |
| JP | 2004-537354 | 12/2004 |
| JP | 2006-230722 | 9/2006 |
| JP | 2006-528540 | 12/2006 |
| JP | 2007-503884 | 3/2007 |
| JP | 2007-517627 | 7/2007 |
| JP | 2007-190389 | 8/2007 |
| JP | 2007-521881 | 8/2007 |
| JP | 2008-510526 | 4/2008 |
| JP | 2008-522787 | 7/2008 |
| JP | 2008-537498 | 9/2008 |
| JP | 2009-533167 | 9/2009 |
| JP | 2010-510852 | 4/2010 |
| JP | 2010-173739 | 8/2010 |
| JP | 2012-509740 | 4/2012 |
| JP | 2012-521221 | 9/2012 |
| JP | 2013-534451 | 9/2013 |
| JP | 2013-535247 | 9/2013 |
| JP | 2014-513583 | 6/2014 |
| JP | 2014-523751 | 9/2014 |
| JP | 2015-500701 | 1/2015 |
| MX | 6012309 | 1/2007 |
| WO | WO 88/006022 | 8/1988 |
| WO | WO 93/014721 | 8/1993 |
| WO | WO 94/004088 | 3/1994 |
| WO | WO 97/047246 | 12/1997 |
| WO | WO 98/048717 | 11/1998 |
| WO | WO 99/023963 | 5/1999 |
| WO | WO 00/038582 | 7/2000 |
| WO | WO 00/053126 | 9/2000 |
| WO | WO 01/030248 | 5/2001 |
| WO | WO 02/045765 | 6/2002 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |
| WO | WO 2005/076974 | 8/2005 |
| WO | WO 2006/023980 | 3/2006 |
| WO | WO 2006/096803 | 9/2006 |
| WO | WO 2008/008522 | 1/2008 |
| WO | WO 2008/103843 | 8/2008 |
| WO | WO 2009/013397 | 1/2009 |
| WO | WO 2009/015100 | 1/2009 |
| WO | WO 2009/021876 | 2/2009 |
| WO | WO 2010/060072 | 5/2010 |
| WO | WO 2010/122472 | 10/2010 |
| WO | WO 2011/011621 | 1/2011 |
| WO | WO 2012/007941 | 1/2012 |
| WO | WO 2012/116266 | 8/2012 |
| WO | WO 2012/116267 | 8/2012 |
| WO | WO 2012/154265 | 11/2012 |
| WO | WO 2013/022880 | 2/2013 |
| WO | WO 2013/138655 | 9/2013 |
| WO | WO 2014/078541 | 5/2014 |
| WO | WO 2016/044432 | 3/2016 |
| WO | WO 2020/030656 | 2/2020 |
| WO | WO 2020/236229 | 11/2020 |
| WO | WO 2021/163313 | 8/2021 |

OTHER PUBLICATIONS

Official Communication in Australian Application No. AU2016231622, dated Dec. 5, 2017.
Official Communication in Australian Application No. AU2016231622, dated Nov. 22, 2018.
Notice of Acceptance in Australian Application No. AU2016231622, dated Dec. 4, 2018.
Official Communication in European Application No. 16180368.9, dated Jan. 11, 2018.
Official Communication in Canadian Application No. 2,804,223, dated Jun. 5, 2017.
Official Communication in Canadian Application No. 2,804,223, dated Mar. 14, 2018.
Official Communication in Japanese Application No. 2015-242990, dated May 8, 2017.
Official Communication in Japanese Application No. 2015-242990, dated Aug. 21, 2017.
Official Communication in European Application No. EP12749447.4, dated Nov. 14, 2018.
Official Communication in European Application No. 12749251.0, dated May 9, 2017.
Official Communication in Japanese Application No. 2016-246368, dated Oct. 30, 2017.
Official Communication in Japanese Application No. 2016-246368, dated Jul. 2, 2018.
Official Communication in Japanese Application No. JP 2013-555592, dated Jan. 5, 2018.
Official Communication in Japanese Application No. 2016-237460, dated Oct. 23, 2017.
Official Communication in Japanese Application No. 2016-237460, dated Apr. 16, 2018.
Official Communication in Australian Application No. 2014241989, dated Aug. 31, 2017.
Official Communication in Australian Application No. 2014241989, dated Jun. 20, 2018.
Official Communication in Australian Application No. 2014241989, dated Aug. 17, 2018.
Official Communication in Japanese Application No. JP 2016-500490, dated Nov. 27, 2017.
Official Communication in Japanese Application No. JP 2016-500490, dated May 7, 2018.
Official Communication in Australian Application No. 2014241994, dated Oct. 30, 2017.
Official Communication in Japanese Application No. JP 2016-500498, dated Jan. 5, 2018.
Official Communication in Japanese Application No. JP 2016-500498, dated Jul. 2, 2018.
Official Communication in Japanese Application No. JP 2016-500498, dated Mar. 4, 2019.
Official Communication in Australian Application No. 2014327083, dated May 31, 2018.
Official Communication in Japanese Application No. JP 2016-517392, dated Jun. 4, 2018.
Official Communication in European Application No. 16743832.4, dated Jul. 24, 2018.

(56) References Cited

OTHER PUBLICATIONS

International Preliminary Report on Patentability and Written Opinion in International Application No. PCT/US2016/013062, dated Aug. 10, 2017.
3rd Party Lab Notebook, "Facet Cartilage Repair," dated May 20, 2003 in 2 pages.
ArthroTek, "CurvTek® Bone Tunneling System," Surgical Technique, 2000, pp. 6.
ArthroTek, "CurvTek® Bone Tunneling System," User's Manual, 2000, pp. 20.
Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.
Beaman, MD et al., "Substance P Innervation of Lumbar Spine Facet Joints", SPINE, 1993, vol. 18, No. 8, pp. 1044-1049.
Butterman, et al., "An Experimental Method for Measuring Force on the Spinal Facet Joint: Description and Application of the Method", Journal of Biomechanical Engineering, Nov. 1991, vol. 113, pp. 375-386.
Cruess et al., "The Response of Articular Cartilage to Weight-Bearing Against Metal", The Journal of Bone and Joint Surgery, Aug. 1984, vol. 66-B, No. 4, pp. 592-597.
Dalldorf et al., "Rate of Degeneration of Human Acetabular Cartilage after Hemiarthroplasty", The Journal of Bone and Joint Surgery, Jun. 1995, vol. 77. No. 6, pp. 877-882.
E-mail from 3rd Party citing U.S. Appl. No. 60/721,909; U.S. Appl. No. 60/750,005 and U.S. Appl. No. 60/749,000, initial e-mail dated May 11, 2009, reply e-mail dated May 18, 2009.
Frost, Harold M., "From Wolff's Law to the Utah Paradigm: Insights About Bone Physiology and Its Clinical Applications", The Anatomical Record, 2001, vol. 262, pp. 398-419.
King et al., "Mechanism of Spinal Injury Due to Caudocephalad Acceleration," Symposium on the Lumbar Spine, Orthopedic Clinic of North America, Jan. 1975, vol. 6, pp. 19-31.
Kuriz, PhD et al., "Isoelastic Polyaryletheretherketone Implants for Total Joint Replacement", PEEK Biomaterials Handbook, Ch. 14, 2012, pp. 221-226.
Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.
Panjabi, PhD et al., "Articular Facets of the Human Spine: Quantitative Three-Dimensional Anatomy", SPINE, 1993, vol. 18, No. 10, pp. 1298-1310.
Parteq Innovations, "Facet Joint Implants & Resurfacing Devices," Technology Opportunity Bulletin, Tech ID 1999-012, Queen's University, Ontario Canada, pp. 2.
Ravikumar et al., "Internal Fixation Versus Hemiarthroplasty Versus Total Hip Arthroplasty for Displaced Subcapital Fractures of Femur—13 year Results of a Prospective Randomised Study", International Journal of the Care of the Injured (INJURY), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. AU2013237744, dated Sep. 2, 2014.
Notice of Acceptance in Australian Application No. AU2013237744, dated Apr. 23, 2015.
Official Communication in Australian Application No. AU2015205875, dated Apr. 2, 2016.
Official Communication in Australian Application No. AU2015205875, dated Jun. 15, 2016.
Official Communication in Canadian Application No. 2,555,355, dated Sep. 2, 2011.
Official Communication in Canadian Application No. 2,803,783, dated Sep. 29, 2014.
Official Communication in Canadian Application No. 2,803,783, dated Aug. 5, 2015.
Official Communication in Canadian Application No. 2,803,783, dated Jul. 7, 2016.
Official Communication in Canadian Application No. 2,803,783, dated Apr. 5, 2017.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in European Application No. 14175088.5, dated Nov. 18, 2015.
Official Communication in European Application No. 16180368.9, dated Mar. 31, 2017.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
Official Communication in Japanese Application No. 2012-272106, dated Feb. 23, 2015.
Official Communication in Japanese Application No. 2012-272106, dated Nov. 2, 2015.
International Search Report and Written Opinion in International Application No. PCT/US2005/003753, dated Dec. 5, 2006.
International Preliminary Report and Written Opinion in International App No. PCT/US2005/003753, dated Jan. 9, 2007.
Official Communication in European Application No. 08730413.5, dated Feb. 16, 2012.
Official Communication in European Application No. 14177951.2, dated Nov. 13, 2014.
International Search Report and Written Opinion in International Application No. PCT/US2008/054607, dated Jul. 10, 2008.
International Preliminary Report on Patentability in International Application No. PCT/US2008/054607, dated Sep. 3, 2009.
Official Communication in Australian Application No. 2011292297, dated Jul. 10, 2013.
Official Communication in Australian Application No. 2014277721, dated Sep. 8, 2016.
Official Communication in Australian Application No. 2014277721, dated Jan. 9, 2017.
Official Communication in European Application No. 11818586.7, dated Nov. 6, 2014.

(56) References Cited

OTHER PUBLICATIONS

Official Communication in European Application No. 11818586.7, dated Feb. 3, 2017.
Official Communication in Japanese Application No. 2013-524882, dated Mar. 2, 2015.
Official Communication in Japanese Application No. 2013-524882, dated Nov. 16, 2015.
Official Communication in Japanese Application No. 2015-242990, dated Dec. 12, 2016.
International Search Report and Written Opinion in International Application No. PCT/US2011/047432, dated Dec. 12, 2011.
International Preliminary Report on Patentability in International Application No. PCT/US2011/047432, dated Feb. 28, 2013.
Official Communication in Australian Application No. AU2012222229, dated Aug. 21, 2015.
Official Communication in Australian Application No. AU2012222229, dated May 11, 2016.
Official Communication in Australian Application No. AU2012222230, dated Aug. 21, 2015.
Official Communication in European Application No. EP12749447.4, dated Jan. 4, 2017.
Official Communication in European Application No. EP12749447.4, dated Apr. 4, 2017.
Official Communication in European Application No. 12749251.0, dated Jan. 4, 2017.
Official Communication in Japanese Application No. JP 2013-555591, dated Jan. 4, 2016.
Official Communication in Japanese Application No. JP 2013-555591, dated Nov. 21, 2016.
Official Communication in Japanese Application No. JP 2013-555592, dated Dec. 7, 2015.
Official Communication in Japanese Application No. JP 2013-555592, dated Aug. 8, 2016.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 12, 2014.
Official Communication in European Application No. 14774714.1, dated Oct. 21, 2016.
International Search Report and Written Opinion in International Application No. PCT/US2014/019302, dated May 18, 2015.
Official Communication in European Application No. 14776445.0, dated Nov. 7, 2016.
International Search Report and Written Opinion in International Application No. PCT/US2014/019325, dated Jun. 17, 2014.
International Preliminary Report on Patentability and Written Opinion in International Application No. PCT/US2014/019325, dated Sep. 24, 2015.
Official Communication in European Application No. 14850082.0, dated Aug. 31, 2016.
International Search Report and Written Opinion in International Application No. PCT/US2014/056598, dated Dec. 29, 2014.
International Preliminary Report on Patentability and Written Opinion in International Application No. PCT/US2014/056598, dated Apr. 7, 2016.
International Search Report and Written Opinion in International Application No. PCT/US2015/050441, dated Dec. 28, 2015.
International Preliminary Report on Patentability and Written Opinion in International Application No. PCT/US2015/050441, dated Mar. 30, 2017.
International Search Report and Written Opinion in International Application No. PCT/US2016/013062, dated Mar. 16, 2016.
International Search Report in International Application No. PCT/CA2002/000193 filed Feb. 15, 2002, dated Jun. 18, 2002.
International Search Report and Written Opinion in International Application No. PCT/US2004/028094, dated May 16, 2005.
International Preliminary Report on Patentability in International Application No. PCT/US2004/028094, dated Feb. 25, 2013.
International Search Report in International Application No. PCT/US2005/000987 filed Jan. 13, 2005, dated May 24, 2005.
International Preliminary Report on Patentability in International Application No. PCT/US2005/000987 filed Jan. 13, 2005, dated Jan. 17, 2006.
Official Communication in Australian Application No. AU2019201539, dated Jun. 25, 2019.
Official Communication in European Application No. 19158915.9, dated Jul. 1, 2019.
Official Communication in European Application No. 14774714.1, dated May 23, 2019.
Notice of Acceptance in Australian Application No. 2014327083, dated Apr. 3, 2019.
Official Communication in Japanese Application No. JP 2016-517392, dated Apr. 22, 2019.
Official Communication in European Application No. 12749251.0, dated Aug. 16, 2019.
Official Communication in Australian Application No. 2016212009, dated Sep. 6, 2019.
Official Communication in Japanese Application No. 2017-557269, dated Oct. 21, 2019.
Official Communication in Australian Application No. 2019201539, dated Apr. 3, 2020.
Official Communication in Australian Application No. 2018279003, dated Jan. 9, 2020.
Official Communication in Canadian Application No. 2,903,999, dated Dec. 9, 2019.
Official Communication in Australian Application No. 2014241994, dated Jan. 31, 2020.
Official Communication in Canadian Application No. 2,904,280, dated Dec. 9, 2019.
Official Communication in Australian Application No. 2016212009, dated May 26, 2020.
International Search Report and Written Opinion in International Application No. PCT/US2020/014985, dated Apr. 24, 2020.
Official Communication in Japanese Application No. JP 2016-500498, dated Aug. 9, 2019.
Official Communication in Japanese Application No. JP 2016-517392, dated Dec. 2, 2019.
Official Communication in Australian Application No. 2018279003, dated Sep. 18, 2020.
Official Communication in Canadian Application No. 2,903,999, dated Aug. 31, 2020.
Official Communication in Canadian Application No. 2,904,280, dated Sep. 1, 2020.
Official Communication in Japanese Application No. 2019-163133, dated Oct. 5, 2020.
Official Communication in Australian Application No. 2019206045, dated Sep. 8, 2020.
Official Communication in Canadian Application No. 2,923,623, dated Dec. 8, 2020.
Official Communication in European Application No. 14850082.0, dated Sep. 15, 2020.
Official Communication in Japanese Application No. 2019-236855, dated Nov. 24, 2020.
Official Communication in Australian Application No. 2016212009, dated Jul. 14, 2020.
Official Communication in Japanese Application No. 2017-557269, dated Jul. 13, 2020.
Official Communication in European Application No. 11818586.7, dated Apr. 8, 2021.
Official Communication in European Application No. EP12749447.4, dated Aug. 18, 2021.
Official Communication in Australian Application No. 2018279003, dated Jan. 12, 2021.
Official Communication in Canadian Application No. 2,904,280, dated Jun. 7, 2021.
Official Communication in European Application No. 14776445.0, dated Jun. 10, 2021.

(56) References Cited

OTHER PUBLICATIONS

Official Communication in Japanese Application No. 2019-163133, dated Jun. 7, 2021.
Official Communication in Australian Application No. 2019206045, dated Sep. 9, 2020.
Official Communication in Australian Application No. 2019206045, dated Jul. 16, 2021.
Official Communication in Japanese Application No. 2019-236855, dated Jun. 28, 2021.
Official Communication in Japanese Application No. 2020-181320, Sep. 21, 2021.
International Search Report and Written Opinion in International Application No. PCT/US2021/017643, dated Apr. 28, 2021.
Official Communication in Australian Application No. 2020244544, dated Nov. 15, 2021.
Official Communication in Austra2020281016lian Application No. 2016212009, dated Nov. 24, 2021.
Official Communication in Japanese Application No. 2017-557269, dated Nov. 1, 2021.
International Preliminary Report on Patentability and Written Opinion in International Application No. PCT/US2020/014985, dated Dec. 2, 2021.
Official Communication in Australian Application No. 2020244544, dated Apr. 27, 2022.
Official Communication in Australian Application No. 2020244544, dated Jun. 8, 2022.
Official Communication in Canadian Application No. 2,904,280, dated Apr. 1, 2022.
Official Communication in European Application No. 14776445.0, dated May 20, 2022.
Official Communication in Canadian Application No. 2,972,788, dated Jan. 31, 2022.
Invitation to Pay Additional Search Fees in International Application No. PCT/US2021/072351, dated Jan. 13, 2022.
International Search Report and Written Opinion in International Application No. PCT/US2021/072351, dated Mar. 18, 2022.
International Search Report and Written Opinion in International Application No. PCT/US2022/070851, dated May 13, 2022.

\* cited by examiner

FLEXIBLE FASTENING BAND CONNECTOR

CROSS-REFERENCE TO RELATED APPLICATIONS

This application is the U.S. National Phase under 35 U.S.C. § 371 of International Application No. PCT/US2015/050441, filed Sep. 16, 2015, titled FLEXIBLE FASTENING BAND CONNECTOR, which claims priority benefit to U.S. Provisional Patent Application No. 62/051,454, filed Sep. 17, 2014, the entirety of which is hereby incorporated by reference herein.

FIELD

The present application relates to surgical methods and apparatuses for stabilizing bone, and more particularly to the flexible fastening band connectors and a method of using the flexible fastening band connectors.

BACKGROUND

Traumatic, inflammatory, and degenerative disorders of the spine can lead to severe pain and loss of mobility. One source of back and spine pain is related to degeneration of the spine or arthritis. Bony contact or grinding of degenerated surfaces can play a role in some pain syndromes. Many technological advances have focused on the intervertebral disc and artificial replacement or repair of the intervertebral disc.

The current standard of care to address the degenerative problems is to fuse the two adjacent vertebrae. By performing this surgical procedure, the relative motion between the two adjacent vertebrae is stopped, thus stopping motion of the vertebra and any potential pain generated as a result thereof. Procedures to fuse two adjacent vertebrae often involve fixation and/or stabilization of the two adjacent vertebrae until the two adjacent vertebrae fuse.

Injuries and/or surgical procedure on and/or effecting other bones can also result in the desire to fixate and/or stabilize a bone until the bone, or bone portions, can fuse, for example, to stabilize a sternum after heart surgery, to stabilize a rib after a break, etc. Current procedures to fixate and/or stabilize adjacent vertebrae and/or other bones, however, can be slow and/or complex.

Accordingly, a need exists for an apparatus and methods to better stabilize and/or fixate a bone.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

These and other features, aspects and advantages of the described embodiments are described with reference to drawings of certain preferred embodiments, which are intended to illustrate, but not to limit. It is to be understood that the attached drawings are for the purpose of illustrating concepts of the described embodiments and may not be to scale.

DETAILED DESCRIPTION

As used in this specification, the singular forms "a," "an" and "the" include plural referents unless the context clearly dictates otherwise. Thus, for example, the term "a ratchet" is intended to mean a single ratchet or a combination of ratchets. As used in this specification, a substance can include any biologic and/or chemical substance, including, but not limited to, medicine, adhesives, etc. While exemplary references are made with respect to vertebra, in some embodiments another bone can be involved. While specific reference may be made to a specific vertebra and/or subset and/or grouping of vertebrae, it is understood that any vertebra and/or subset and/or grouping, or combination of vertebrae can be used. As will be described herein, various embodiments will be described as "substantially" matching, parallel, coplanar and/or perpendicular. In such embodiments, "substantially" can mean within plus or minus a few percent (e.g., 1, 2, 3, 4, or 5, etc.) from the given shape or orientation, in other embodiments, within plus or minus 10 degrees from the given orientation, and in other embodiments, within plus or minus 5 degrees from the given orientation.

Figure 1:
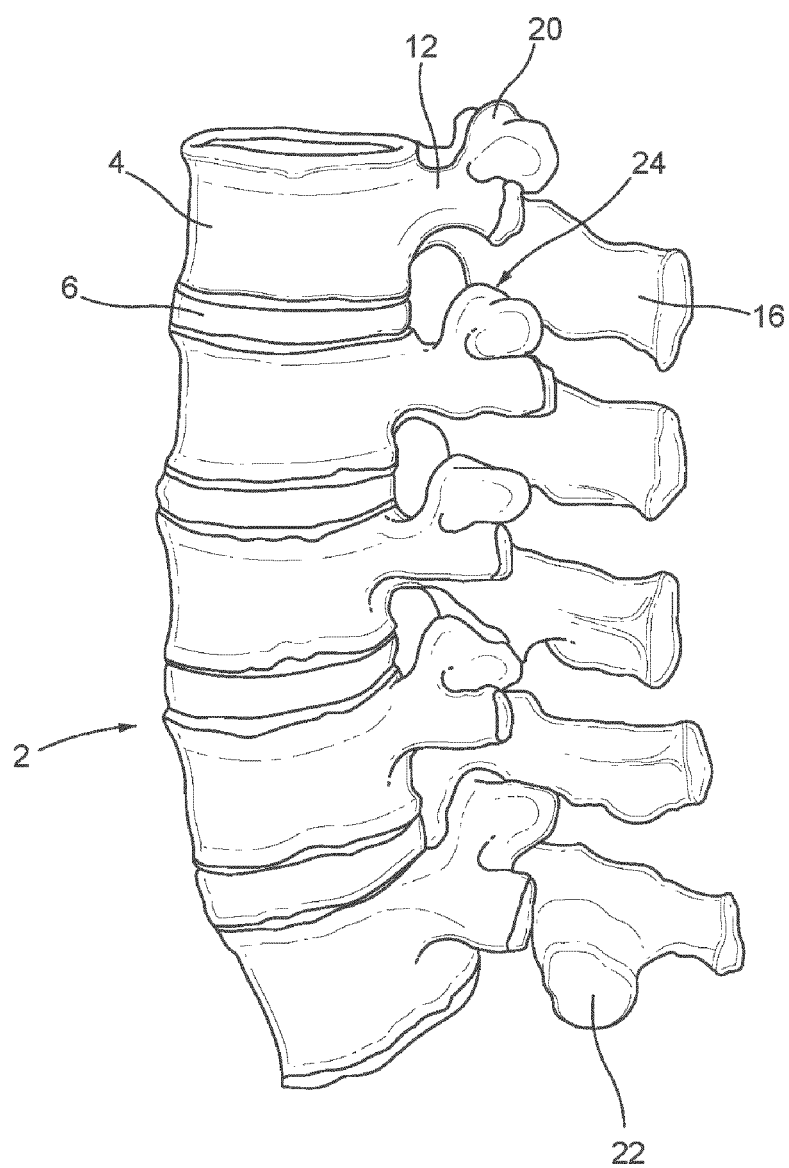
FIG. 1 is a lateral elevational view of a portion of the vertebral column.
Figure 2A:
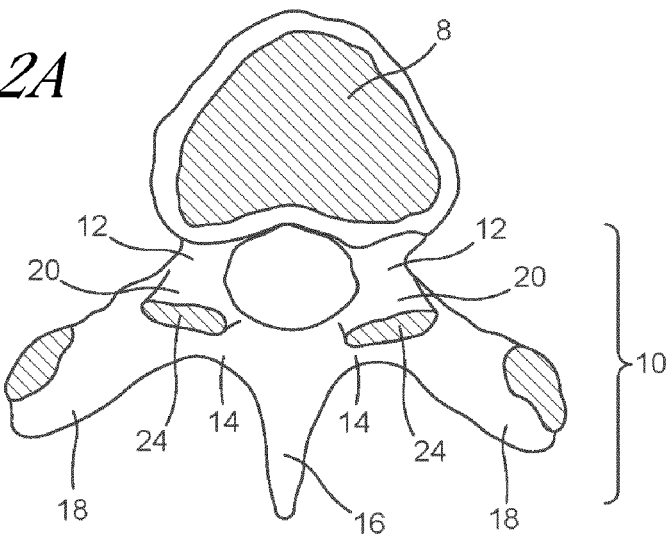
FIG. 2A is an example of a superior view of an isolated thoracic vertebra.
Figure 2B:
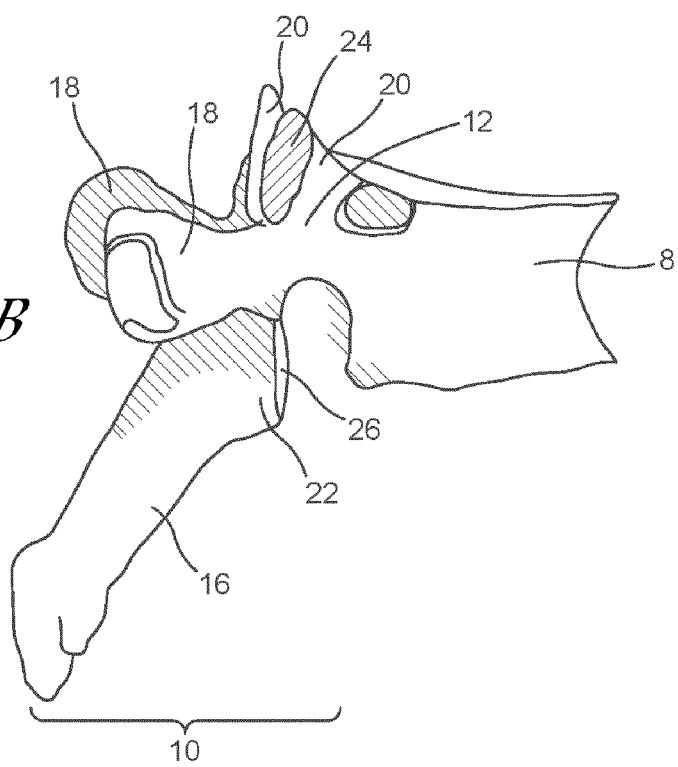
FIG. 2B is an example of a side view of an isolated thoracic vertebra.
Figure 3A:
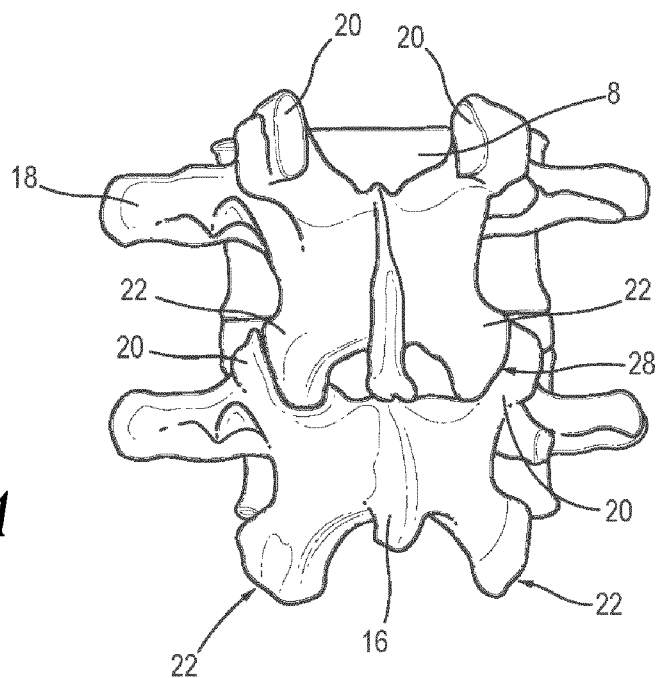
FIG. 3A is an example of a posterior elevational view of a portion of the vertebral column.
Figure 3B:
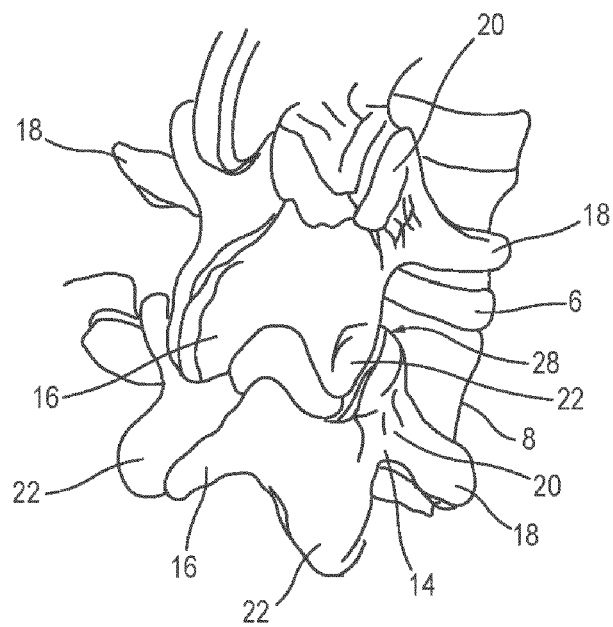
FIG. 3B is an example of a posterior-oblique elevational view of a portion of the vertebral column.
Figure 4A:
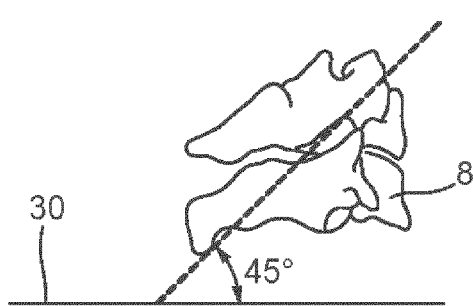
FIG. 4A is an example of a side view of a facet joint in the cervical vertebrae.
Figure 4B:
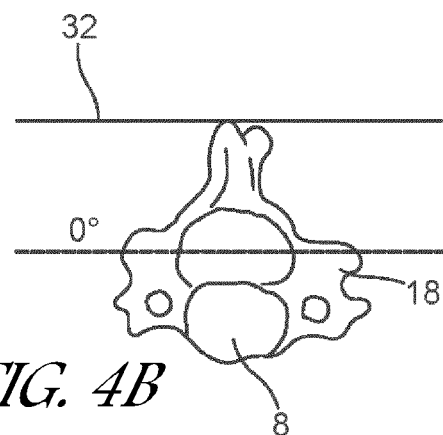
FIG. 4B is an example of a superior view of a facet joint in the cervical vertebrae.

As shown in FIG. 1, the vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 comprises two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 with the articular processes of the adjacent vertebrae (see FIGS. 3A and 3B). The facet joints are true synovial joints with cartilaginous surfaces and a joint capsule.

Figure 5A:
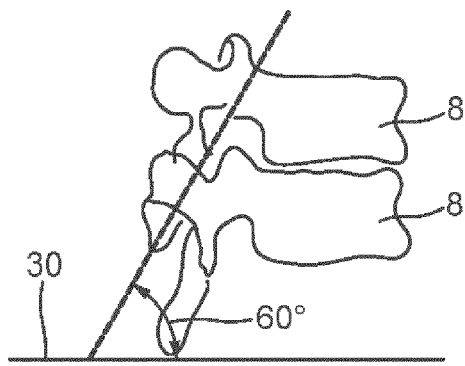
FIG. 5A is an example of a side view of a facet joint in the thoracic vertebrae.
Figure 5B:
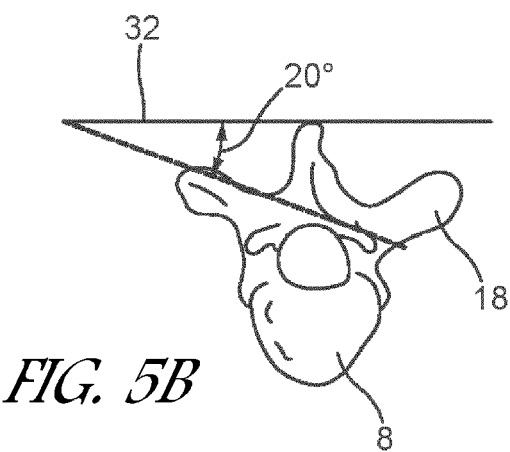
FIG. 5B is an example of a superior view of a facet joint in the thoracic vertebrae.
Figure 6A:
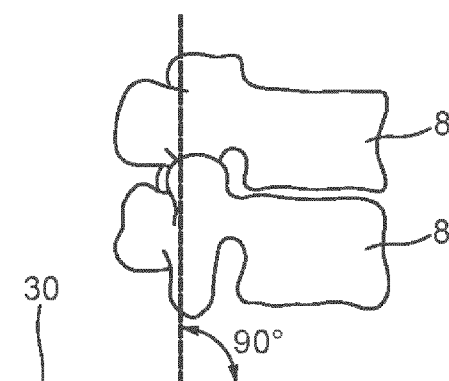
FIG. 6A is an example of a side view of a facet joint in the lumbar vertebrae.
Figure 6B:
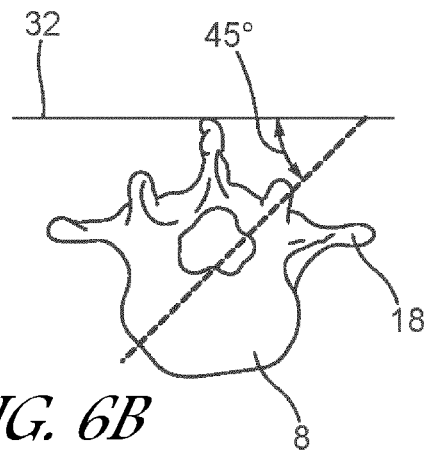
FIG. 6B is an example of a superior view of a facet joint in the lumbar vertebrae.

The orientation of the facet joints vary, depending on the level of the vertebral column. In the C1 and C2 vertebrae, for example the facet joints are parallel to the transverse plane. FIGS. 4A to 6B depict examples of the orientations of the facet joints at different levels of the vertebral column. In the C3 to C7 vertebrae examples shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict examples of the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate examples of the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, Orthop. Clin. North Am., 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

FIGS. 7-18C illustrates various embodiments of a flexible fastening band ("band") that can be used to provide fixation in a spinal (or other orthopedic or surgical) procedure. Additional description and embodiments of the flexible fastening band are described in U.S. Pat. No. 8,740,949 (issued on Jun. 3, 2014), U.S. Publication 2012/0221049 (filed Feb. 23, 2012) and Applicant's co-pending patent application Ser. No. 13/804,407 (filed Mar. 14, 2013) and Ser. No. 13/804,521 (filed Mar. 14, 2013), the entirety of these applications being incorporated by reference into this specification. As will be described in detail below, FIGS. 19-31 illustrate various embodiments of a flexible fastening band connector ("connector") that can be used in certain arrangements in combination with a band such as the band described herein and/or with other fixation devices. An advantage of certain embodiments is that the connector can align portions of the band or other fixation device with each other to ease the fixation process and/or to reduce wear and stress on the band.

Figure 7:
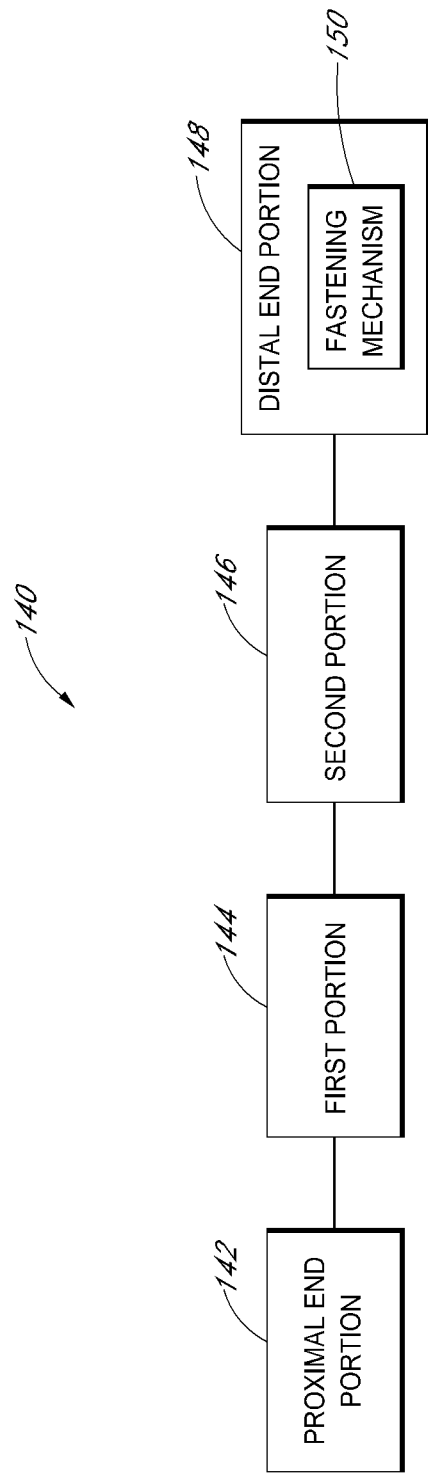
FIG. 7 is a block diagram of a bone stabilization and distraction apparatus according to an embodiment.

FIG. 7 depicts a block diagram of the flexible fastening band ("band") 140. The band 140 includes a flexible elongate body including a proximal end portion 142, a first portion 144, a second portion 146, and a distal end portion 148 that includes a fastening mechanism 150 (alternatively referred to herein as a fastener). In some embodiments, the band 140 can include a third portion (not shown in FIG. 7). In some embodiments, the band 140 can include a spacer (not shown in FIG. 7). The band 140 can be configured to anchor to a first vertebra (not shown in FIG. 7) and/or a second vertebra (not shown in FIG. 7). In some embodiments, the band 140 can be removed from the vertebra, e.g. by cutting, breaking, or otherwise releasing the band 140. In this manner, should the band 140 fail, a replacement band 140 can be inserted. Similarly, should the band 140 be deemed ineffective for a particular patient, the band 140 can be removed and an alternate treatment can be chosen without incurring permanent fusion of the vertebra. As will be described in more detail herein, the band 140 can be monolithically formed or separately formed. The band 140 can include any biocompatible material, e.g., stainless steel, titanium, PEEK, nylon, etc.

In some embodiments described herein, a flexible fastening band can be used to stabilize and/or fixate a first vertebra to a second vertebra to reduce the pain, to reduce further degradation of a spine, or of a specific vertebra of a spine, and/or until the first vertebra and the second vertebra have fused. Specifically, the band 140 can be coupled to a first bone portion and secured to one or more spinal devices, as described herein. In some embodiments, the band 140 can be extended around a bone portion. In some embodiments, the band 140 can be passed through a lumen formed through adjacent vertebra. The flexible fastening band is configured to form a loop either through one or more adjacent bone portions or around one or more bone portions.

The proximal end portion 142 is sized to pass through a fastening mechanism 150 of the distal end portion 148 to form a loop. In some embodiments, the proximal end portion 142 can be shaped to increase the ease of inserting the proximal end portion 142 into the fastening mechanism 150, e.g., the proximal end portion 142 can be tapered, rounded, and/or angled, etc., to reduce at least a portion of a cross-sectional area of the proximal end portion 142.

The first portion 144 can extend for a length between the proximal end portion 142 and the second portion 146, and can have a substantially uniform shape. The first portion 144 can have, for example, a substantially cuboidal shape, or a substantially cylindrical shape. In some embodiments, the length of the first portion 144 can be more than twice the length of the second portion 146. In some embodiments, the cross-sectional area of the first portion 144 can be smaller than the cross-sectional area of the second portion 146. In some embodiments, the cross-sectional area of the first portion 144 can be less than a cross-sectional area of a lumen defined by the fastening mechanism 150. The first portion 144 can include a gear rack (not shown in FIG. 7) configured to engage a ratchet (not shown in FIG. 7) of the fastening mechanism 150. The gear rack can be configured to allow the first portion 144 to travel through the fastening mechanism 150 in only one direction. The first portion 144 can be monolithically formed with the second portion 146. In some other embodiments, the first portion 144 can be separately formed from the second portion 146. The first portion 144 can be configured to be slidably disposed in a lumen of the second portion 146.

The second portion 146 can have a length between the first portion 144 and the distal end portion 148, and can include a substantially uniform shape. In embodiments including the third portion, the second portion 146 can have a length between the first portion 144 and the third portion. The second portion 146 can have, for example, a substantially cuboidal shape or a substantially cylindrical shape. The first portion 144 and the second portion 146 can have the same or different shapes, e.g., the first portion 144 and the second portion 146 can both be substantially cuboidal, the first portion 144 and the second portion 146 can both be substantially cylindrical, the first portion 144 can be substantially cuboidal while the second portion 146 can be substantially cylindrical, or the first portion 144 can be substantially cylindrical while the second portion 146 can be substantially cuboidal. In some embodiments, the length of the second portion 146 can be less than half the length of the first portion 144. In some embodiments, the cross-sectional area of the second portion 146 can be greater than the cross-sectional area of the first portion 144. In some embodiments, the cross-sectional area of the second portion 146 can be greater than a cross-sectional area of a lumen defined by the fastening mechanism 150. In this manner, as a portion of the band 140 is advanced through the fastening mechanism 150, the cross-sectional area of the second portion 146 can prevent the band 140 from advancing beyond the first portion 144. The second portion 146 can include a gear rack (not shown in FIG. 7) configured to engage the ratchet of the fastening mechanism 150. The gear rack can be configured to allow the second portion 146 to travel through the fastening mechanism 150 in only one direction. The second portion 146 can be monolithically formed with the first portion 144. In some embodiments, the second portion 146 can be separately formed from the first portion 144. The second portion 146 can define a lumen configured to slidably accept the first portion 144.

The distal end portion 148 includes the fastening mechanism 150 configured to accept at least the portion of proximal end portion 142, the first portion 144, and/or the second portion 146. In some embodiments, the distal end portion 148, the second portion 146, the first portion 144, and the proximal end portion 142 can be monolithically formed. The fastening mechanism 150 includes a lumen (not shown in FIG. 7) configured to accept at least a portion of the proximal end portion 142, a portion of the first portion 144, and/or a portion of the second portion 146. In some embodiments, the cross-sectional area of the lumen of the fastening mechanism 150 is smaller than the cross-sectional area of the second portion 146. In this manner, the second portion 146 can be prevented from advancing through the fastening mechanism 150. In some embodiments, the fastening mechanism 150 can include a ratchet (not shown in FIG. 7) configured to engage the gear rack of the first portion 144 and/or second portion 146. In this manner, the fastening mechanism 150 can allow the first portion 144 and/or the second portion 146 to advance through the fastening mechanism 150 in only one direction.

In some embodiments, at least one of the distal end portion 148, the second portion 146, the first portion 144, and the proximal end portion 142 can be formed separately from the other(s) of the distal end portion 148, the second portion 146, the first portion 144, and the proximal end portion 142. Said another way, and by way of example, the distal end portion 148, the first portion 144, and the proximal end portion 142 can be monolithically formed together, while the second portion 146 can be separately formed. In this manner, the band 140 can include an initial second portion 146 configured to be replaced and/or covered with a replacement second portion 146. By way of a first example, the initial second portion 146 can be monolithically formed with the first portion 144 and the replacement second portion 146 can be slidably disposed over the initial second portion 146. By way of a second example, the initial second portion 146 can be separately formed from the first portion 144, can be removed from the band 140, and the replacement second portion 146 can be slidably disposed over the first portion 144. By way of a third example, the initial second portion 146 can be separately or monolithically formed from the first portion 144, and the replacement second portion 146 can be slidably disposed over the first portion 144 and the initial second portion 146. In some embodiments, the initial second portion 146 and the replacement second portion 146 can have the same shape, e.g., the initial second portion 146 can include a substantially cylindrical shape and the replacement second portion 146 can include a substantially cylindrical shape. In some embodiments, the initial second portion 146 and the replacement second portion 146 can have different shapes, e.g., the initial second portion 146 can include a substantially cuboidal shape and the replacement second portion 146 can include a substantially cylindrical shape.

In some embodiments, the shape of first portion 144 and the shape of second portion 146 can be determined based on the shape of an artificial lumen formed through an articular process of a vertebra. By way of example, if the shape of the artificial lumen is cuboidal, the shape of the first portion 144 and the shape of the second portion 146 can be cuboidal to allow the first portion 144 and the second portion 146 to slidably advance through the artificial lumen. By way of a second example, if the shape of the artificial lumen is cylindrical, the shape of the first portion 144 and the shape of the second portion 146 can be either cuboidal or cylindrical. Continuing with the second example, the shape of the first portion 144 can be cuboidal to allow the first portion 144 to advance easily through the artificial lumen, while the shape of the second portion 146 can be cylindrical to allow the second portion 146 to fit more tightly within the artificial lumen as compared to a cuboidal shape.

In some embodiments, the shape of the first portion 144 and the shape of the second portion 146 can be determined based on characteristics of the bone or bone portion against which the first portion 144 and the second portion 146 may contact. By way of example, while the first portion 144 and/or the second portion 146 can be substantially cuboidal, the edges of the first portion 144 and/or the second portion 146 can be rounded, partially rounded, and/or otherwise shaped to compliment the shape of a bone or bone portion, and/or to reduce digging or grinding into the bone or bone portion. In this manner, use of the band 140 may cause little or no damage to the bone or bone portions contacted by the band 140.

In some embodiments, the band 140 can include a third portion (not shown in FIG. 7). The third portion can have a length between the second portion 146 and the distal end portion 148, and can have a substantially uniform shape. In some embodiments, the third portion can have, for example, a substantially cuboidal shape or a substantially cylindrical shape. In some embodiments, the length of the third portion can be less than half the length of first portion 144. The third portion can be monolithically formed with first portion 144 and/or the second portion 146. In some other embodiments, the third portion can be separately formed from the second portion 146 and/or the first portion 144.

While each of the first portion 144, the second portion 146, and the third portion can be a substantially uniform shape, in some embodiments any one of the first portion 144, the second portion 146, and the third portion can include a transition portion to transition the band 140 from a first substantially uniform shape to a second substantially uniform shape. By way of example, in some embodiments, the first portion 144 and the third portion can be substantially cuboidal and the second portion 146 can be substantially cylindrical. In this example, the second portion 146 can include an angled, conical, or other shaped transition portion.

Figure 8:
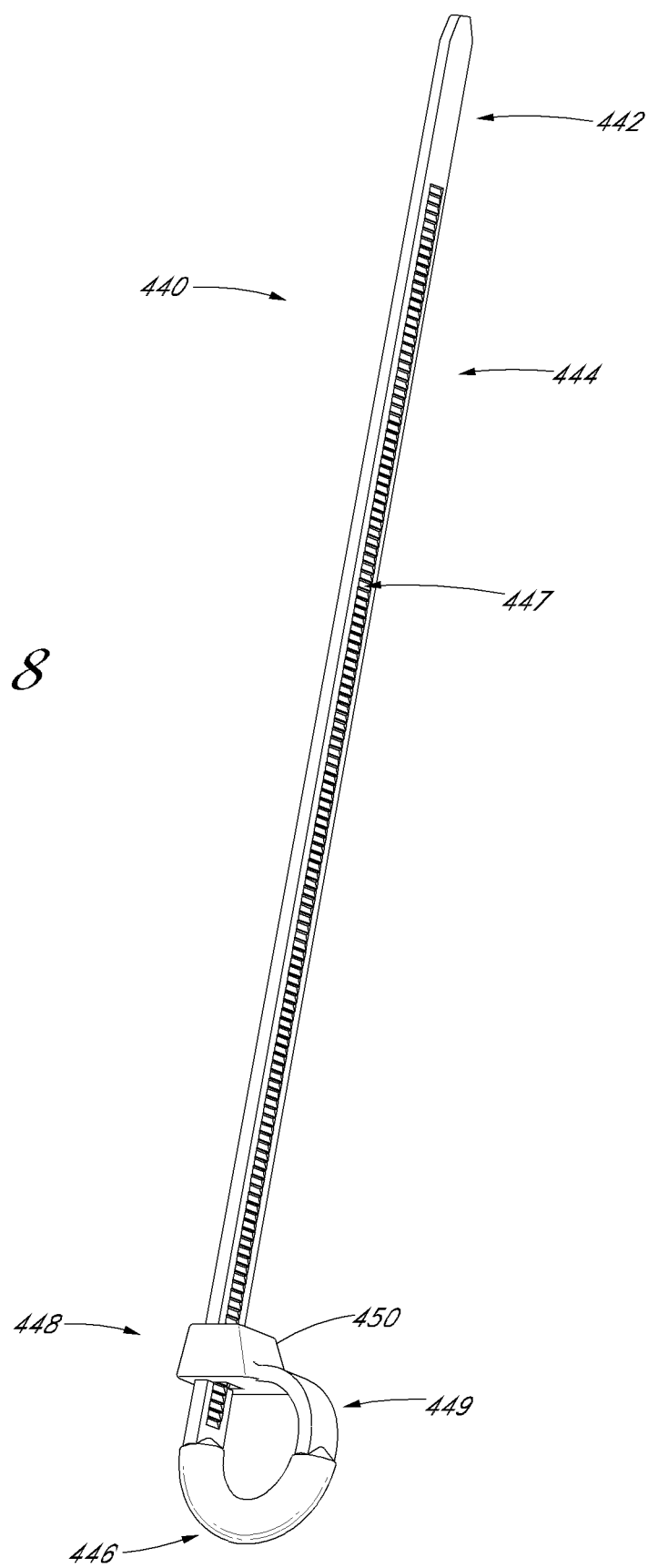
FIG. 8 is a perspective view of a flexible fastening band according to an embodiment.
Figure 9:
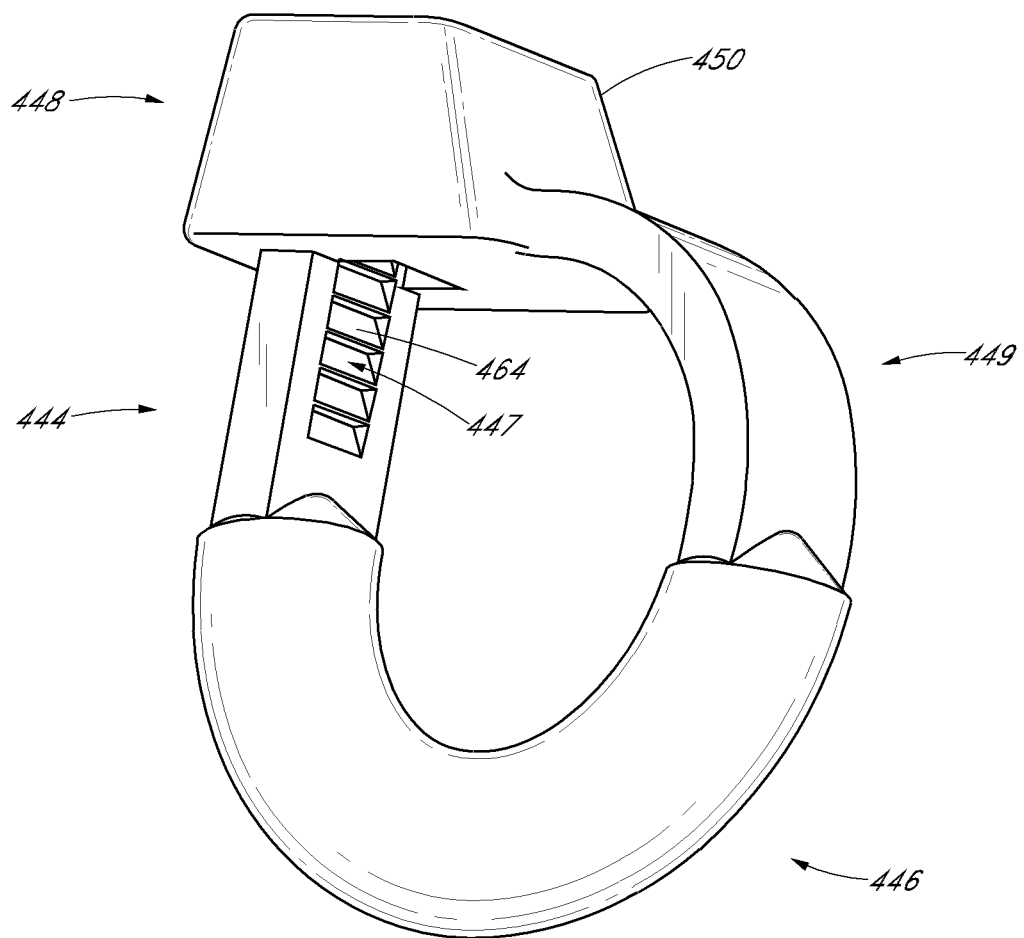
FIG. 9 is a perspective view of a portion of the flexible fastening band depicted in FIG. 8.

FIG. 8 depicts views of a flexible fastening band ("band") 440 and FIG. 9 depicts a view of a portion of band 440. The band 440 can be similar to the band 140 described above and can include similar components. By way of example, the band 440 includes a proximal end portion 442, a first portion 444, a second portion 446, and a distal end portion 448 including a fastening mechanism 450. The band 440 includes a cylindrical second portion 446 and a third portion 449. As depicted in FIGS. 8-9, third portion 449 is substantially the same shape as first portion 442. Second portion 446 can be substantially the same diameter as the diameter of the lumen in a first bone portion and/or second bone portion. When the diameter of the second portion is substantially the same as the lumen, the amount of open space within the lumen can be minimized, the amount of surface area of the second portion 446 of the band 440 in contact with the lumen can increase, and subsequently the movement of bone portions can be reduced or minimized. Furthermore, when movement of the bone portions does occur, forces acting against the band 440 can be more equally distributed throughout the second portion of the band, due at least to the increased surface area of the band 440 in contact with the lumen. As shown in FIGS. 8 and 9, the band 440 includes a gear rack 447 and gears 464. Each of the gears 464 can be wedge shaped to allow each of the gears 464 to displace the ratchet of the fastening mechanism 450 in only one direction. In some embodiments, the gears 464 can be other shapes, such as blocks, etc.

A band according to this embodiment may be particularly useful in deployments where a single band in used to stabilize adjacent vertebrae. In this manner, the second portion 446 can be disposed within the lumen of a first bone portion (e.g., the first articular process of the first vertebra) and a portion of the first portion 444 can be disposed within the lumen of the first bone portion or a second bone portion (e.g., the second articular process of the second vertebra). In these embodiments the portion of the band within the first articular process of the first vertebra and the portion of the band within in the second articular process of the second vertebra can both have substantially the same shape as the lumen in the first articular process of the first vertebra and the lumen in the second articular process of the second vertebra.

Figure 10:
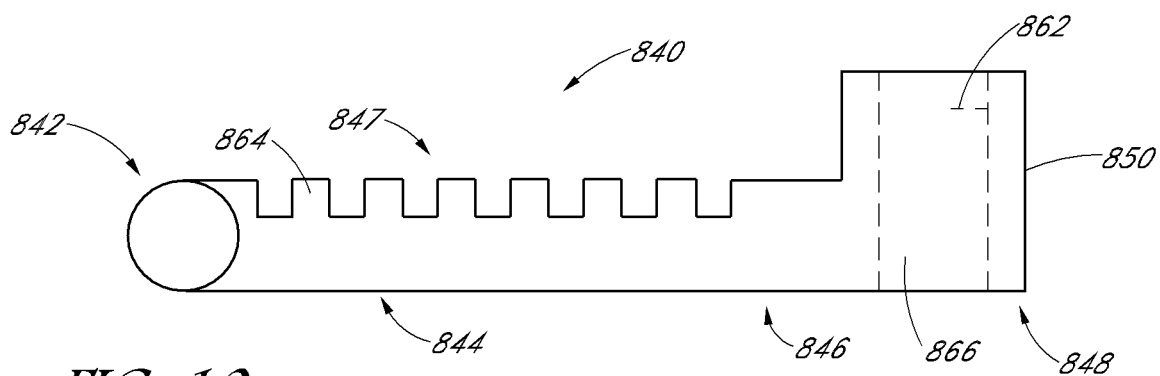
FIG. 10 is a side view of a flexible fastening band according to an embodiment.
Figure 11:
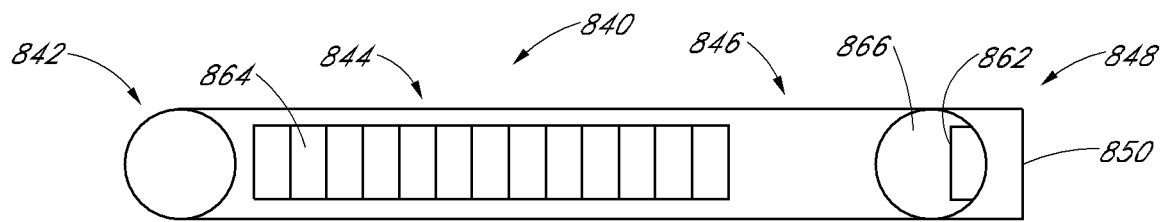
FIG. 11 is a top view the flexible fastening band depicted in FIG. 10.

FIG. 10 is a side view and FIG. 11 is a top view of a flexible fastening band ("band") 840 according to another embodiment. The band 840 can be similar to the band 140 and the band 440 described above and can include similar components. By way of example, the band 840 includes a proximal end portion 842, a first portion 844 including a gear rack 847, a second portion 846, and a distal end portion 848 including a fastening mechanism 850 and a ratchet 862. In contrast to the gear rack 447, a cross sectional area of each gear 864 of gear rack 847 is rectangular in shape instead of wedge shaped. Furthermore, the first portion 844 is cylindrical in shape instead of cuboidal in shape. In this manner, the lumen 866 of the fastening mechanism 850 is cylindrical in shape.

Figure 12:
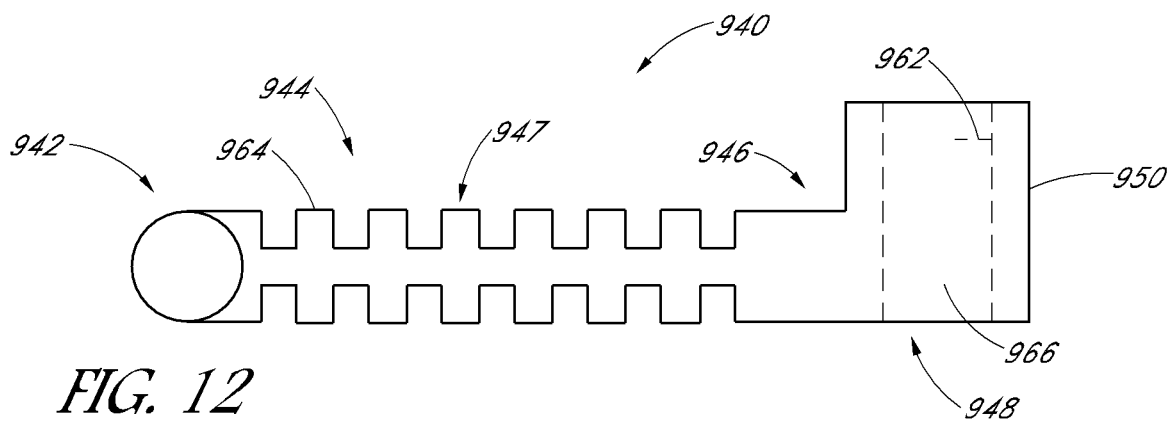
FIG. 12 is a side view of a flexible fastening band according to an embodiment.

FIG. 12 is a side view a flexible fastening band ("band") 940 according to an embodiment. The band 940 can be similar to the band 140, the band 440, and the band 840 described above and can include similar components. By way of example, the band 940 includes a proximal end portion 942, a first portion 944 including a gear rack 947, a second portion 946, and a distal end portion 948 including a fastening mechanism 950. Similar to the gear rack 847, a cross sectional area of each gear 964 of gear rack 947 is rectangular in shape. In contrast to the gear rack 847, each of the gears 964 extend the entire circumference of the first portion 944 instead of only a portion of the circumference of the first portion 944. Furthermore, the first portion 944 is cylindrical in shape instead of cuboidal in shape. In this manner, the lumen 966 of the fastening mechanism 950 is cylindrical in shape. A band according to this embodiment may be particularly useful in deployments where the movement and repositioning of the band after implantation may be difficult. In this manner, because each of the gears can be the entire circumference of the first portion and/or the second portion, the first portion and/or the second portion can enter the fastening mechanism in any radial orientation and still engage the ratchet.

Figure 13:
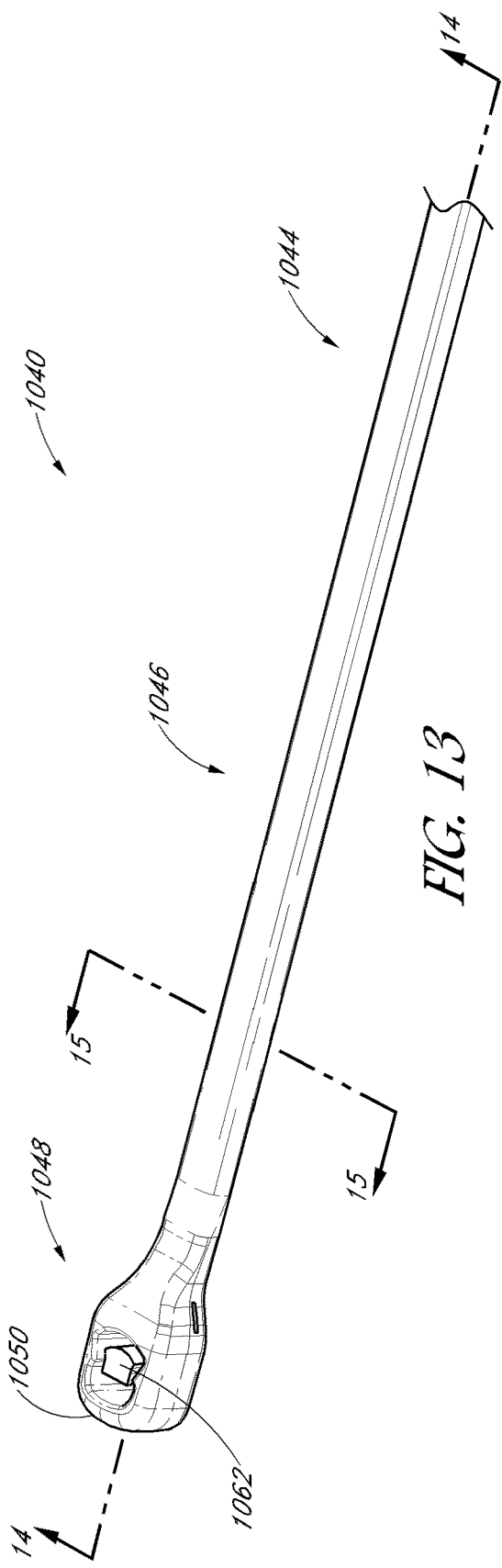
FIG. 13 is a perspective view of a flexible fastening band according to an embodiment.
Figure 14:
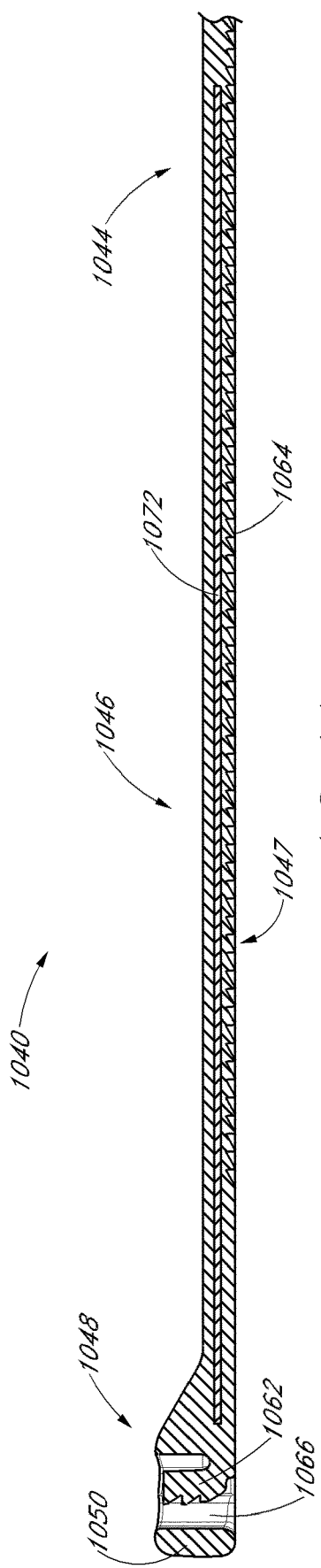
FIG. 14 is a cross-sectional side view taken along line 14-14 of the flexible fastening band depicted in FIG. 13.
Figure 15:
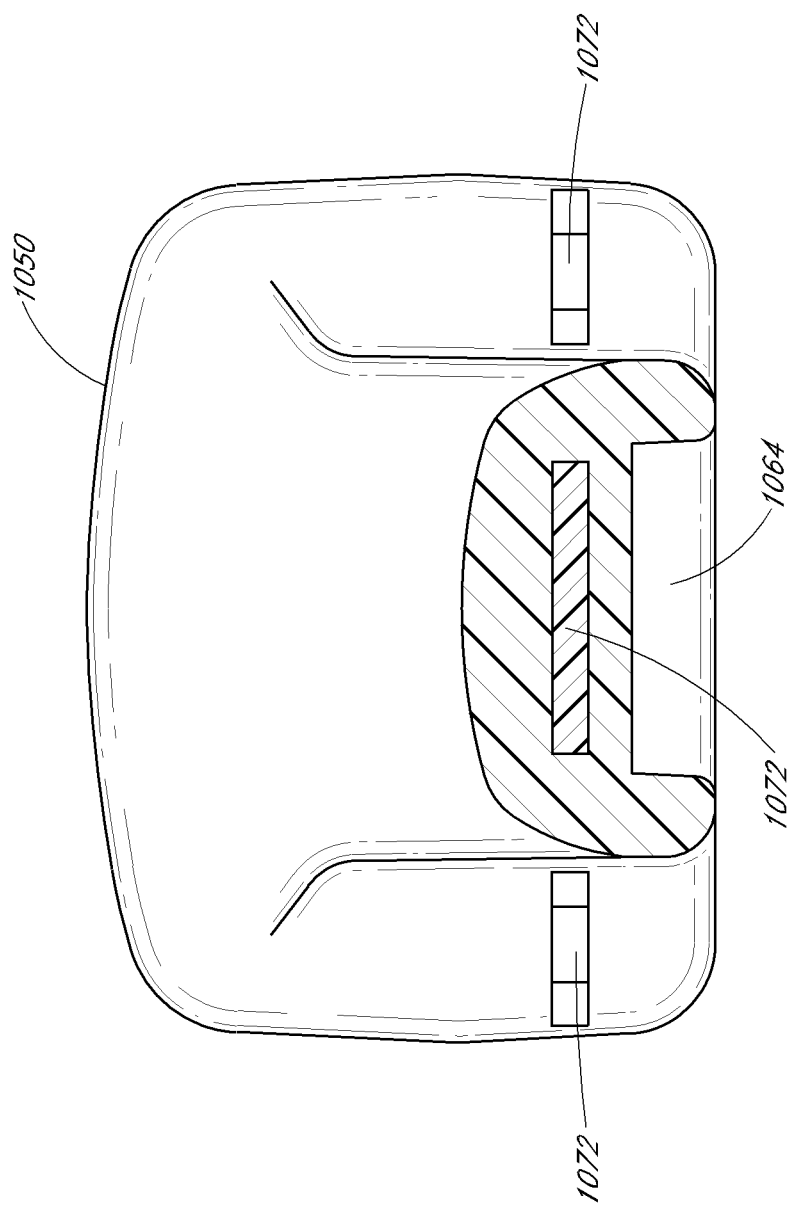
FIG. 15 is a cross-sectional view taken along line 15-15 of the flexible fastening band depicted in FIG. 13.
Figure 16:
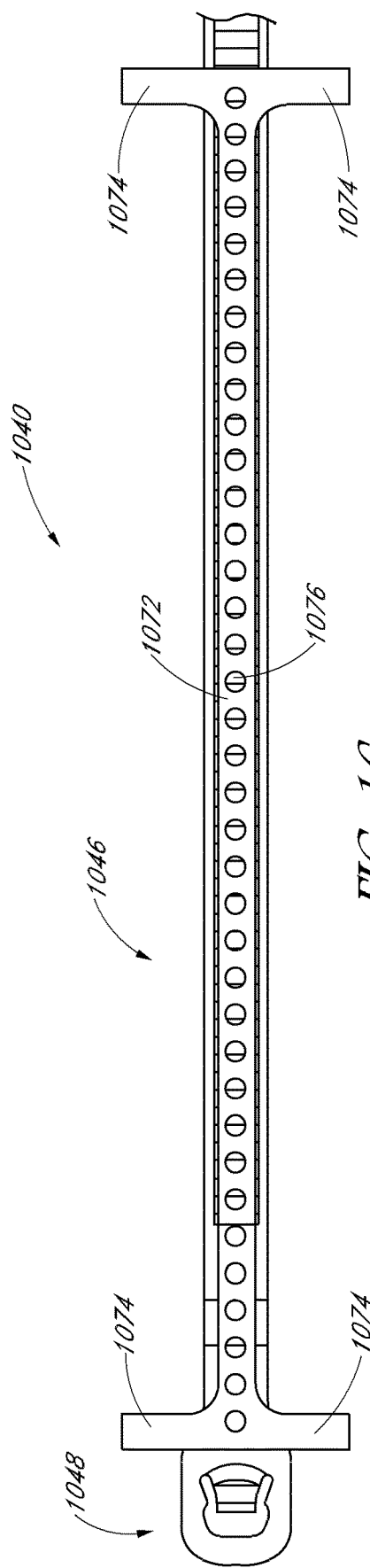
FIG. 16 is a cross-sectional top view of the flexible fastening band depicted in FIG. 13 in a first configuration.
Figure 17:
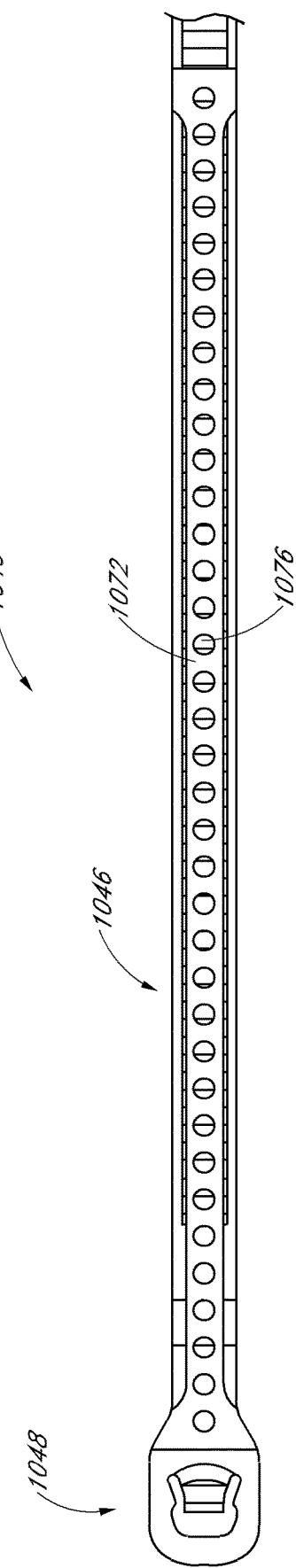
FIG. 17 is a cross-sectional top view of the flexible fastening band depicted in FIG. 13 in a second configuration.

FIGS. 13-17 are views of a flexible fastening band ("band") 1040 according to another embodiment. FIG. 13 is a perspective view and FIG. 14 is a cross-sectional side view of the band 1040. FIG. 15 is a cross-sectional view of the band 1040 taken along line 15-15. FIG. 16 is a cross-sectional top view of the band 1040 in a first configuration and FIG. 17 is a cross-sectional top view of the band 1040 in a second configuration. The band 1040 can be similar to the band 140, the band 440, the band 840, and/or the band 940 described above and can include similar components. By way of example, the band 1040 includes a proximal end portion (not shown), a first portion 1044 including a gear rack 1047 (see FIG. 14), a second portion 1046, and a distal end portion 1048 including a fastening mechanism 1050, a ratchet 1062 and a lumen 1066. In contrast to the band 140, the band 1040 includes a reinforcement piece 1072.

The reinforcement piece 1072 can include any of the materials described above for the band 140. In some embodiments, the reinforcement piece 1072 can include a material stronger than the second portion 1046 and/or the first portion 1044, for example, the first portion 1044 and the second portion 1046 can include PEEK and the reinforcement piece 1072 can include titanium. As shown in FIG. 14, the reinforcement piece 1072 can be disposed within the band 1040 approximately along the entire length of the second portion 1046, and a portion of the reinforcement piece 1072 can be disposed within the distal end portion 1048. In some embodiments, the reinforcement piece can include a length along at least a portion of the length of the second portion 1046 and/or first portion 1044 but not the distal end portion 1048. In some embodiments, the reinforcement piece 1072 can be disposed only within the second portion 1046. The reinforcement piece 1072 can have a length in first dimension (length), a length in a second dimension (width), and a length in a third dimension (height). As described herein, a reinforcement piece can be different shapes that can include more or fewer dimensions.

The reinforcement piece 1072 can be molded within the band 1040. Said another way, in embodiments where the first portion, the second portion, and/or the distal end portion are moldable materials, the reinforcement piece 1072 can be placed in the mold and the moldable materials can be injected or otherwise put in the mold around the reinforcement piece. In other embodiments, each portion of the band (for example, the proximal end portion, the first portion, the second portion, the third portion, and/or the distal end portion) around the reinforcement piece can have a top half and a bottom half, and each of the top half and the bottom half can be placed around the reinforcement piece, and sealed. As shown in FIG. 16, reinforcement piece 1072 includes support members 1074. While FIG. 16 shows reinforcement piece 1072 including four support members 1074, in some embodiments, more or fewer support members 1074 can be used. The support members 1074 can maintain the position of the reinforcement piece 1072 during the molding and/or assembly process of the band 1040. As shown in FIG. 17, the support members 1074 are removed before the band 1040 is used.

As shown in FIG. 15, the reinforcement piece 1072 can has a substantially uniform cuboidal shape. In other embodiments, the reinforcement piece 1072 can have other shapes. The shape of the reinforcement piece can be selected depending on the desired bending and/or torsion characteristics of the material chosen. By way of example, a substantially planar cuboidal shape can provide a greater increase in bending strength while providing a lesser increase in torsion strength, a cylindrical shape can provide an increase in bending strength while providing very little increase in torsion strength, a substantially square and/or tubular cuboidal shape can provide similar bending and torsion increases. Any shape can be selected to achieve the desired bending and torsion strength. Combinations of materials and shapes can also be considered. For example, a material having higher torsion strength may be combined with a shape having a lower torsion strength to combine for the desired torsion strength. As shown in FIGS. 16 and 17, the reinforcement piece 1072 can include one or more holes 1076 distributed along the length of the first dimension. While FIGS. 16 and 17 shows the band 1040 including many holes 1076, in some embodiments, more or fewer holes 1076 can be used. FIGS. 16 and 17 depict the holes 1076 distributed substantially equally along the length of the first dimension, in some embodiments, the holes can be distributed differently or along different dimensions depending on the shape and/or material chosen, and/or whether the reinforcement piece is solid or hollow. The holes 1076 can be configured to reduce the weight of the reinforcement piece 1072 while still provided the band 1040 additional strength. The holes 1076 can be round, oval, square, or any other shape.

Figure 18A:
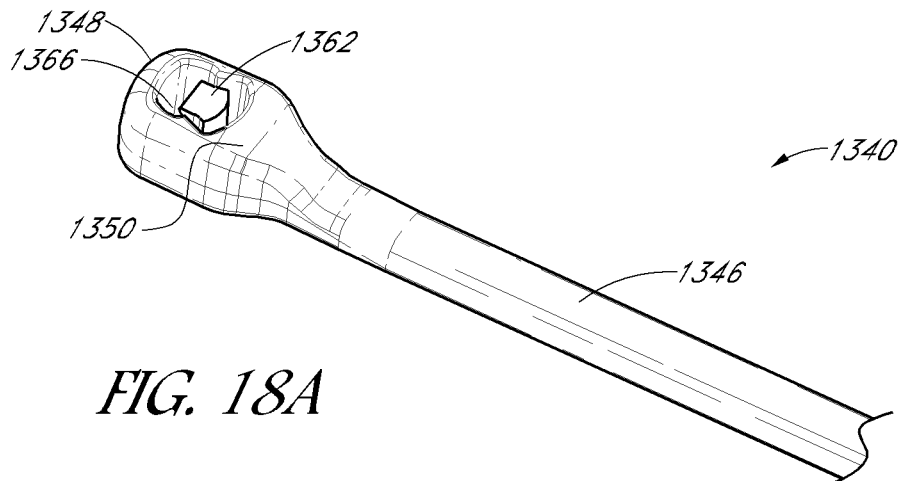
FIGS. 18A-18C are various perspective views of a flexible fastening band according to another embodiment.
Figure 18B:
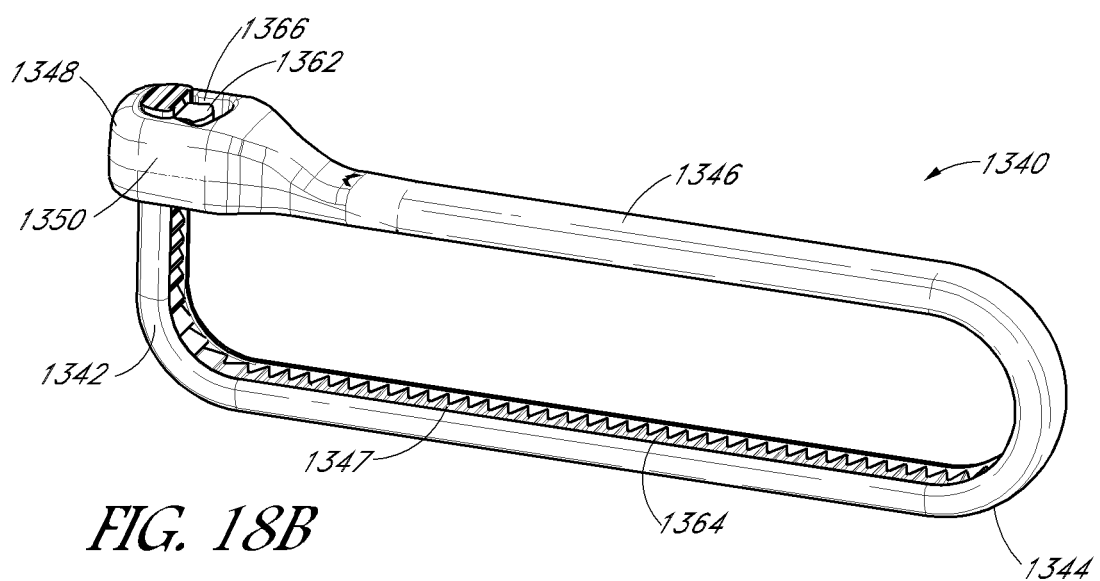
Figure 18C:
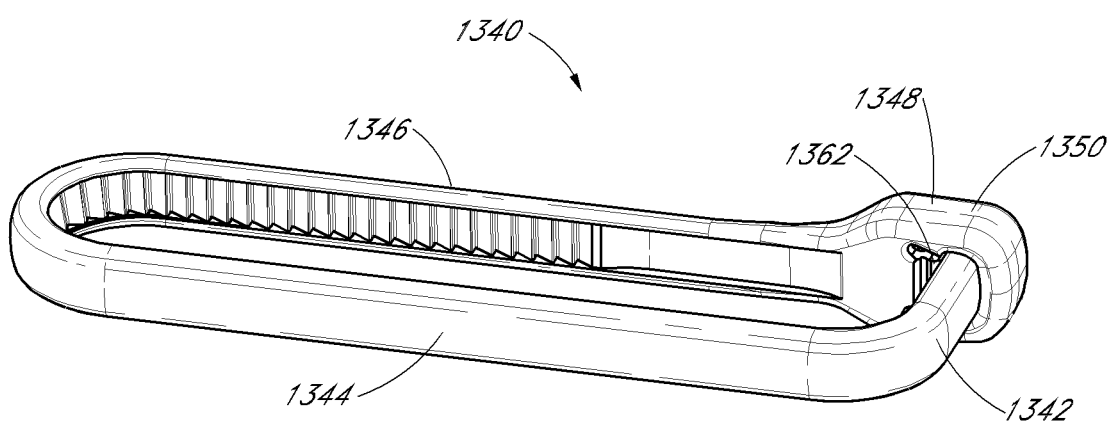

FIGS. 18A-18C illustrate a flexible fastening band 1340 (also referred to herein as "band") according to an embodiment. The band 1340 can be similar to the band 140, the band 440, the band 840, the band 940, and the band 1040 and can include similar components. By way of example, the band 1340 includes a distal end portion 1348, a fastener mechanism 1350 including a ratchet 1362, a second portion 1346, a first portion 1344, and a proximal end portion 1342. Accordingly, components of the band 1340 that are similar to corresponding components of the band 140 described above with reference to FIG. 7 are not described in further detail herein.

Each gear 1364 included in the gear rack 1347 includes a cross sectional area that is rectangular in shape. Said another way, each gear 1364 can be a rectangular protrusion configured to extend from a surface of the band 1340 (e.g., the first portion 1344 and/or the second portion 1346). The gear rack 1347 is configured to engage the ratchet 1362 of the fastener mechanism 1350, as further described herein. The fastener mechanism 1350 defines a lumen 1366. The lumen 1366 can be any suitable shape, size, or configuration. For example, as shown in FIG. 18A the lumen 1366 can have a substantially circular cross-sectional area. The ratchet 1362 extends from an inner surface of the fastener member 1350 such that the ratchet 1362 substantially reduces the size (e.g., the perimeter, circumference, and/or cross-sectional area) of the lumen 1366. In this manner, the ratchet 1366 can engage the gear rack 1347. More specifically, as described in detail with reference to FIG. 7, the proximal end portion 1342 can be inserted into the lumen 1366 of the fastener mechanism 1350 and advanced in a first direction such that the gear rack 1347 of the first portion 1344 engages the ratchet 1362. In some embodiments, the proximal end portion 1342 can be inserted into the lumen 1366 of the fastener mechanism 1350 and advanced in a first direction such that the gear rack 1347 of the second portion 1346 engages the ratchet 1362.

In some embodiments, the proximal end portion 1342 can be advanced through the lumen 1366 a sufficient distance such that a portion of the first portion 1344 and/or the second portion 1346 is disposed within the lumen 1366. In such embodiments, a portion of the gear rack 1347 disposed on (e.g., included in or defined by) the first portion 1344 and/or the second portion 1346 can engage the ratchet 1362. In this manner, the arrangement of the ratchet 1362 and the gear rack 1347 can be such that the proximal end portion 1342 can be moved in the first direction, thereby tightening the band 1340, and the proximal end portion 1342 can be prevented from moving in a second direction, opposite the first direction, thereby preventing the band 1340 from loosening.

As shown in FIGS. 18A-18C, the band 1340 can be monolithically (or unitarily) constructed in an elongate shape and can have a substantially rectangular cross-sectional shape. More specifically, the band 1340 can have a substantially rectangular shape including rounded edges configured to reduce digging or grinding into the bone or portion thereof. The fastener mechanism 1350 defines a lumen 1366 and includes the ratchet 1362. The first portion 1344 and/or the second portion 1346 includes a gear rack 1347 having a set of gears 1364. In this manner, the proximal end portion 1342 can be inserted into the lumen 1366 of the fastener member 1350 such that the gear rack 1347 engages the ratchet 1362, as described in detail above.

The flexible fastening band can have alternative configurations than those illustrated above. Examples of alternative flexible fastening bands are shown and described in U.S. patent application Ser. No. 13/804,407; filed Mar. 14, 2013, and titled "Apparatus for Spinal and Methods of Use," which is incorporated herein by reference in its entirety.

Connector

Figure 19:
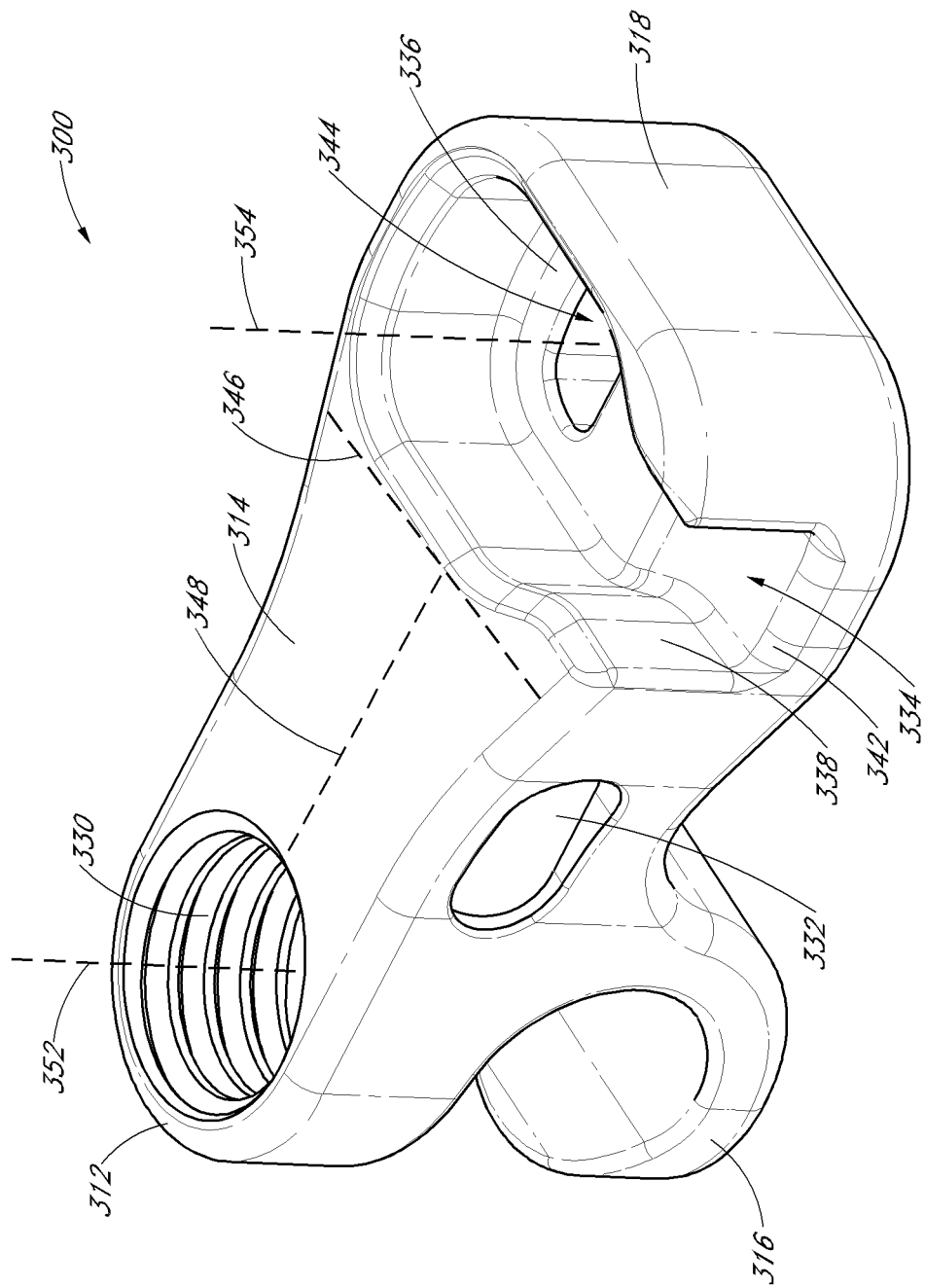
FIG. 19 is a perspective view of a flexible fastening band connector according to an embodiment.
Figure 20:
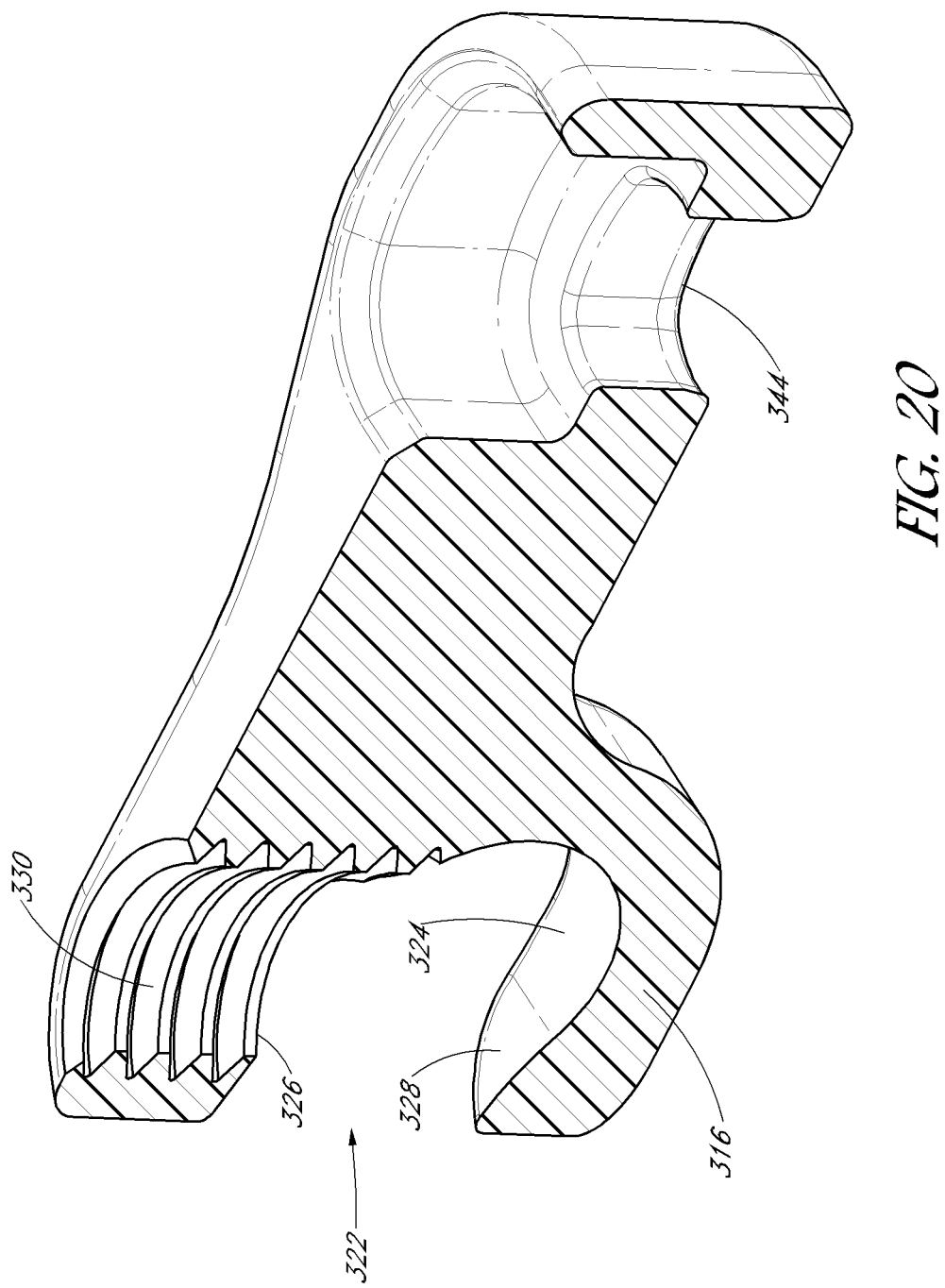
FIG. 20 is a cross-sectional view the flexible fastening band connector depicted in FIG. 19.

In some embodiments described herein, a connector can be used to couple a flexible fastening band to another spinal device, such as a spinal rod. FIG. 19 depicts a connector 300 (also referred to herein as a "flexible fastening band connector") according to an embodiment. FIG. 19 is a perspective view and FIG. 20 is a cross-sectional side view of connector 300. For clarity, components of band 140 are described for use with connector 300, but any band described herein may be utilized.

The connector 300 can include an elongate body including a first portion 312 for engaging a fixation device and a second portion 318 for engaging a flexible fastening band. In some embodiments, the first portion 312 and the second portion 318 are on opposite ends of the connector 300. In some embodiments, the first portion 312 and the second portion 318 are on the same end (e.g., both on the proximal end) of the connector 300. In some embodiments, the first portion 312 is near a proximal end of the connector 300. In some embodiments, the first portion 312 is near the middle of the connector 300 (not shown). In some embodiments, the first portion 312 is near a distal end of the connector 300 (not shown). In some embodiments, the second portion 318 is near a proximal end of the connector 300. In some embodiments, the second portion 318 is near the middle of the connector 300 (not shown). In some embodiments, the second portion 318 is near the distal end of the connector 300 (not shown). The connector 300 can be coupled to the band 140 (or any band described herein) and/or a spinal device, such a support system with a spinal rod. As will be described in more detail herein, the connector 300 can be monolithically formed or formed from a plurality of parts. The connector 300 can include any biocompatible material, e.g., stainless steel, titanium, PEEK, nylon, etc.

In some embodiments, the connector 300 can be coupled to the band 140 and a spinal fixation device or portion thereof such as a spinal rod 240. The spinal rod 240 can be received within an opening 322 of the first portion 312. The opening 322 can be formed in part by a lip portion 316. In the illustrated embodiment, the lip portion 316 forming the opening 322 has a curvature 324 which can match the curvature of the spinal rod 240. In other embodiments, the lip portion 316 can be flat, substantially flat, angled, curved, elliptical or any other shape that corresponds to the shape of the spinal rod 240 and/or is otherwise configured to engage the rod and/or spinal fixation device. In the illustrated embodiment, the first portion 312 forming the opening 322 can have a curvature 326 which matches the curvature of the spinal rod 240 and/or is otherwise configured to engage the rod and/or spinal fixation device. In other embodiments, the first portion 312 can be flat, substantially flat, angled, curved, elliptical or any other shape that corresponds to the shape of the spinal rod 240 and/or is otherwise configured to engage the rod and/or spinal fixation device.

The lip portion 316 can have a dimension (e.g., length along a longitudinal axis 348) equal to or greater than the diameter of the spinal rod 240 to support essentially the entire cross-section of the spinal rod 240. The lip portion 316 can have a dimension (e.g., length) less than the diameter of the spinal rod 240 (e.g., greater than 50% of the diameter, 55%, 60%, 65%, 70%, 75%, 80%, 85%, 90%, 95%, 100%, between 50-80%, between 60-90%, between 70-100%, etc.). The connector 300 can encompass a portion of the circumference of the spinal rod 240 (e.g., greater than 50% of the circumference, 55%, 60%, 65%, 70%, 75%, 80%, 85%, 90%, 95%, 100%, between 50-80%, between 60-90%, between 70-100%, etc.). In some embodiments, the connector 300 can encompass the entire circumference of the spinal rod 240. In some embodiments, the lip portion 316 can encompass a portion of the circumference of the spinal rod 240 (e.g., greater than 25%, 30%, 40%, 45%, 50%, 55%, 60%, 65%, 70%, 75%, 80%, 85%, 90%, 95%, 100%, between 50-80%, between 60-90%, between 70-100%, etc.). In some embodiments, the spinal rod 240 slides into the opening 322 from the proximal end of the connector 300 toward the middle of the connector 300. In some embodiments, the spinal rod 240 slides into the opening 322 from the side of the connector 300 toward the middle of the connector 300 (not shown). In some embodiments, the spinal rod 240 is seated adjacent to the lip portion 316. In the illustrated embodiment, the curvature 324 can include a ridge 328. The ridge 328 can prevent the spinal rod 240 from becoming disengaged. In some embodiments, the spinal rod 240 is seated adjacent to the first portion 312.

The first portion 312 can include a threaded bore 330. The threaded bore 330 can receive a locking mechanism (not shown in FIG. 19) such as, for example, a set screw. Advancing the locking mechanism through the threaded bore 330 can cause the locking mechanism to engage the spinal rod 240. Further advancement of the locking mechanism can cause the locking mechanism to apply a force to the spinal rod 240, which will push the spinal rod 240 toward the lip portion 316. The threaded bore 330 can be perpendicular or substantially perpendicular to a longitudinal axis of the spinal rod 240 when the spinal rod 240 is received within the opening 322. Therefore the applied force would be perpendicular to a longitudinal axis of the spinal rod 240 received within the opening 322. The locking mechanism can apply a force to the surface of the spinal rod 240 to push the spinal rod 240 toward the lip portion 316. In certain embodiments, the locking mechanism can comprise a clamping member, cam member or other device configured to secure the rod or other fixation device within the opening 322 of the first portion 312.

In the embodiments of FIGS. 19-31, the connector 300 is illustrated as connecting a band 140 to a spinal rod 240. In other embodiments, the connector 300 can be configured with openings, slots, grooves, and/or other structures etc. to engage other fixation devices or spinal fixation devices such as, for example, pedicle screws, trans-facet or trans-pedicle screws, spinous process spacers, plates, intervertebral bodies etc.

In the illustrated embodiment, the longitudinal axis 242 of the spinal rod 240 (shown in FIG. 26) received within the opening 322 forms an angle with the longitudinal axis 348 of the connector 300 (e.g., 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, between 90-120°, between 100-130°, between 110-140°, between 120-150°, between 130-160°, between 140-170°, between 150-180°, etc.). In the illustrated embodiment, the longitudinal axis of the spinal rod 240 is perpendicular or substantially perpendicular relative to the longitudinal axis 348 of the connector 300 when the spinal rod 240 is received within the opening 322. In the illustrated embodiment, the longitudinal axis 352 of the threaded bore 330 forms an angle with the longitudinal axis 348 of the connector 300 (e.g., 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, between 90-120°, between 100-130°, between 110-140°, between 120-150°, between 130-160°, between 140-170°, between 150-180°, etc.). In the illustrated embodiment, the longitudinal axis 352 of the threaded bore 330 is perpendicular or substantially perpendicular relative to the longitudinal axis 348 of the connector 300.

In some embodiments, a connecting portion 314 can extend for a length between the first portion 312 and the second portion 318. In the illustrated embodiment, the connecting portion 314 has a curved shape between the first portion 312 and the second portion 318. In some embodiments, the connecting portion 314 has a substantially uniform shape. The connecting portion 314 can have, for example, a substantially cuboidal shape, or a substantially cylindrical shape. In some embodiments, the length of connecting portion 314 can be more than twice the length of the first portion 312. In some embodiments, the cross-sectional area of the connecting portion 314 can be smaller than the cross-sectional area of the first portion 312 and the lip portion 316. In some embodiments, the cross-sectional area of connecting portion 314 can be less than a cross-sectional area of the second portion 318. The connecting portion 314 can include one or more engagement features 332 configured to engage a tool (not shown in FIG. 19) for placement of the connector 300. The engagement features 332 can be a pair of notches disposed on opposite sides of the connecting portion 314. In certain embodiments, the engagement features 332 can be notches, grooves, protrusions and/or other features or combinations thereof configured to facilitate engagement with at tool. The connecting portion 314 can be monolithically formed with the first portion 312 and/or the second portion 318. The connecting portion 314 can be monolithically formed with the lip portion 316. In some embodiments, the lip portion 316 can be separately formed from the connecting portion 314.

The second portion 318 can include a recess 334 sized to accept the distal end portion 148 of the band 140. The recess 334 can have a bottom surface 336 and a side surface 338. In the illustrated embodiment, the bottom surface 336 is flat or substantially flat to match the surface of the distal end portion 148. In other embodiments, the bottom surface 336 can be angled, curved, ribbed or any other shape that corresponds to the surface of the distal end portion 148. In the illustrated embodiment, the side surface 338 is curved to match the shape of the distal end portion 148. In other embodiments, the side surface 338 can be flat angled, ribbed or any other shape that corresponds to the shape of the distal end portion 148. In some embodiments, the side surface 338 can be shaped to increase the ease of inserting the distal end portion 148 into the recess 334, e.g., the side surface 338 can be tapered, rounded, and/or angled, etc., to enlarge at least a portion of a cross-sectional area of the recess 334.

The recess 334 has an opening 342 which causes the side surface 338 to be discontinuous. The opening 342 is sized to receive the first portion 144 and/or the second portion 146 of the band 140. The opening 342 allows the first portion 144 and/or the second portion 146 to extend from the recess 334 when the distal end portion 148 is placed within the recess 334. When viewed from the distal end of the connector 300 (as shown in FIG. 19), the opening 342 can be on the left side of the second portion 318. In the illustrated embodiment, the longitudinal axis 346 of the recess 334 is angled relative to the longitudinal axis 348 of the connector 300. The longitudinal axis 346 of the recess 334 can be at any angle relative to the longitudinal axis 348 of the connector 300 (e.g., 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, between 90-120°, between 100-130°, between 110-140°, between 120-150°, between 130-160°, between 140-170°, between 150-180°, etc.). In the illustrated embodiment, the longitudinal axis 346 of the recess 334 is perpendicular or substantially perpendicular the longitudinal axis 348 of the connector 300.

The side surface 338 and the opening 342 can create a neck which limits the movement of the distal end portion 148 and the fastener 150 in the recess 334. In the illustrated embodiments, the distal end portion 148 is greater in at least one dimension than the first portion 144 and/or the second portion 146 (e.g., length, width, height). In some embodiments, the distal end portion 148 is greater in all three dimensions than the first portion 144 and/or the second portion 146 (e.g., length, width, height). The distal end portion 148 may not fit through the opening 342 and may abut the side surface 338. The distal end portion 148 abuts bottom surface 336. The configuration of the recess 334 including the neck created by the opening 342 and the side surface 338 can limit the movement of the band 140. The opening 342 and the side surface 338 can match or substantially match the shape of the band 140. In some embodiments, there is minimal excess space in the recess (e.g., the side surface 338 abuts at least one side wall of the distal end portion 148). In some embodiments, the distal end portion 148 can be placed in the recess 334 in only one orientation (e.g., to enable the first portion 144 and/or the second portion 146 to extend outward from the recess). This orientation ensures that the lumen 166 of the fastener 150 aligns with the lumen 344 of the connector 300 to permit the proximal end portion 142 to traverse there through. The configuration of the recess 334 including the neck created by the opening 342 and the side surface 338 can align the lumen 166 of the fastener 144 with the lumen 344 of the connector 300.

In the illustrated embodiment, the recess 334 extends from the top surface of the connector 300 toward the bottom surface of the connector 300. In some embodiments, the recess 334 extends from the bottom surface of the connector 300 toward the top surface of the connector 300. In some embodiments, the recess 334 extends from the left side surface of the connector 300 toward the right side surface of the connector 300 when viewed from the distal end of the connector 300. In some embodiments, the recess 334 extends from the right side surface of the connector 300 toward the left side surface of the connector 300 when viewed from the distal end of the connector 300. In the illustrated embodiment, the top surface of the recess 334 is open allowing the distal end portion 148 to be lowered into the recess. In some embodiments, the recess 334 is enclosed such that the distal end portion 148 is enclosed on at least three sides (e.g., four sides, five sides, six sides, etc.).

In some embodiments, the distal end portion 148 lies below the surface of the connector 300 when the distal end portion 148 is disposed in the recess 334. The side surface of the recess 338 can have a depth equal or greater than the depth of the distal end portion 148. The recess 334 can be sized to be greater than the distal end portion 148 in all three dimensions (e.g., length, width, height). In some embodiments, the distal end portion 148 does not protrude from the connector 300 when the distal end portion 148 is disposed in the recess 334. In some embodiments, the distal end portion 148 lies slightly above the surface of the connector 300 when the distal end portion 148 is disposed in the recess 334. The side surface of the recess 338 has a depth less than the depth of the distal end portion 148. The recess 334 can be sized to be greater than the distal end portion 148 in two dimensions (e.g., length, width) but not all three dimensions (e.g., length, width, height). In some embodiments, the distal end portion 148 protrudes from the connector 300 when the distal end portion 148 is disposed in the recess 334.

The recess 334 has a lumen 344. The lumen 344 is sized to receive the proximal end portion 142 of the band 140. The lumen 344 allows proximal end portion 142 to extend through the fastening mechanism 150 when the distal end portion 148 is placed within the recess 334. In some embodiments, the longitudinal axis 354 of the lumen 344 forms an angle with the bottom surface 336. For instance, the longitudinal axis 354 of the lumen 344 can form any angle with the bottom surface 336 (e.g., 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, between 90-120°, between 100-130°, between 110-140°, between 120-150°, between 130-160°, between 140-170°, between 150-180°, etc.). In the illustrated embodiment, the longitudinal axis 354 of the lumen 344 is perpendicular or substantially perpendicular relative to the bottom surface 336. In some embodiments, the longitudinal axis of the lumen 344 forms an angle with the longitudinal axis 348 of the connector 300 (e.g., 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, between 10-40°, between 20-50°, between 30-60°, between 40-70°, between 50-80°, between 60-90°, between 70-100°, between 80-110°, between 90-120°, between 100-130°, between 110-140°, between 120-150°, between 130-160°, between 140-170°, between 150-180°, etc.). In the illustrated embodiment, the longitudinal axis 354 of the lumen 344 is perpendicular or substantially perpendicular relative to the longitudinal axis 348 of the connector 300.

In the illustrated embodiment, the lumen 344 extends from the bottom surface of the connector 300 toward the bottom surface 336 of the recess 334. In some embodiments, the lumen 344 extends from any exterior surface of the connector 300 toward the bottom surface 336 of the recess 334. In some embodiments, the lumen 344 extends from any exterior surface of the connector 300 toward any interior surface. In some embodiments, the lumen 344 extends from any exterior surface of the connector 300 toward any other exterior surface of the connector 300.

In some embodiments, the recess 334 is formed on a first side of the connector 300 and the lumen 344 formed on a second side of the connector 300. The lumen 344 can extend to the recess 334. In some embodiments, the first side of the connector 300 and the second side of the connector 300 are opposed parallel sides of the connector 300. In FIG. 19, the first side of the connector 300 is the top of the connector 300 and the second side of the connector 300 is the bottom of the connector 300. In such configurations, the longitudinal axis 354 of the lumen 344 extends from the top surface to the bottom surface. In some embodiments, the longitudinal axis 354 of the lumen 344 is substantially perpendicular or perpendicular to the longitudinal axis 242 of the spinal rod 240. In other embodiments (see FIGS. 30-31), the first side of the connector 300 is a side surface of the connector 300 and the second side of the connector 300 is the opposed side surface. In such configurations, the longitudinal axis 354 of the lumen 344 can extend from the right side surface to the left side surface. In some embodiments, the longitudinal axis 354 of the lumen 344 is substantially parallel or parallel to the longitudinal axis 242 of the spinal rod 240.

The lumen 344 can serve as a guide for the proximal end portion 142 of the band 140. The lumen 344 can be substantially the same shape as the proximal end portion 142. In some embodiments, the lumen 344 can be substantially the same diameter as the diameter of the proximal end portion 142. When the diameter of the lumen 344 is substantially the same diameter as the proximal end portion 142, the amount of open space within the lumen 344 can be minimized, the amount of surface area of the proximal end portion 142 of the band 140 in contact with the lumen 344 can increase, and the misalignment of the band 140 can be reduced or minimized. Furthermore, when misalignment of the band 140 does occur, forces acting against the band 140 can be more equally distributed throughout the proximal end portion 142, due at least to the increased surface area of the band 140 in contact with the lumen 344.

The proximal end portion 142 can be passed through the lumen 344. The proximal end portion 142 then can pass through the fastening mechanism 150 of the distal end portion 148 received within the recess 334. In some embodiments, the proximal end portion 142 can be shaped to increase the ease of inserting the proximal end portion 142 into the lumen 344, e.g., the proximal end portion 142 can be tapered, rounded, and/or angled, etc., to reduce at least a portion of a cross-sectional area of the proximal end portion 142. In some embodiments, edges of the lumen 344 can be shaped to increase the ease of inserting the proximal end portion 142 into the lumen 344, e.g., the edges of lumen 344 can be tapered, rounded, and/or angled, etc., to enlarge at least a portion of a cross-sectional area of the lumen 344.

In some embodiments, the bands disclosed herein have gear rack with gears. One embodiment is shown in FIGS. 8-9, in which the band 440 includes the gear rack 447 and gears 464. Each of gears 464 can be wedge shaped to allow each of gears 464 to displace the ratchet of fastening mechanism 450 in only one direction. In some embodiments, the gears 464 can be other shapes, such as rectangular, etc. The lumen 344 prevents misalignment between the gear rack of the first portion and/or second portion and the ratchet of the fastening mechanism. The lumen 344 aligns the gear rack in the optimal position to enable engagement of the gears and the ratchet. FIG. 9 shows one such optimal position, with the connector 300 removed for clarity. The gear rack 447 can be perpendicular or substantially perpendicular to the fastening mechanism 450. In many embodiments, the gear rack is perpendicular or substantially perpendicular to the ratchet. Other angles between the gear rack and the ratchet may cause uneven wear or failure of the gear rack and/or the ratchet. Such failure may cause the band to loosen around the bone portion and/or break.

Figure 21:
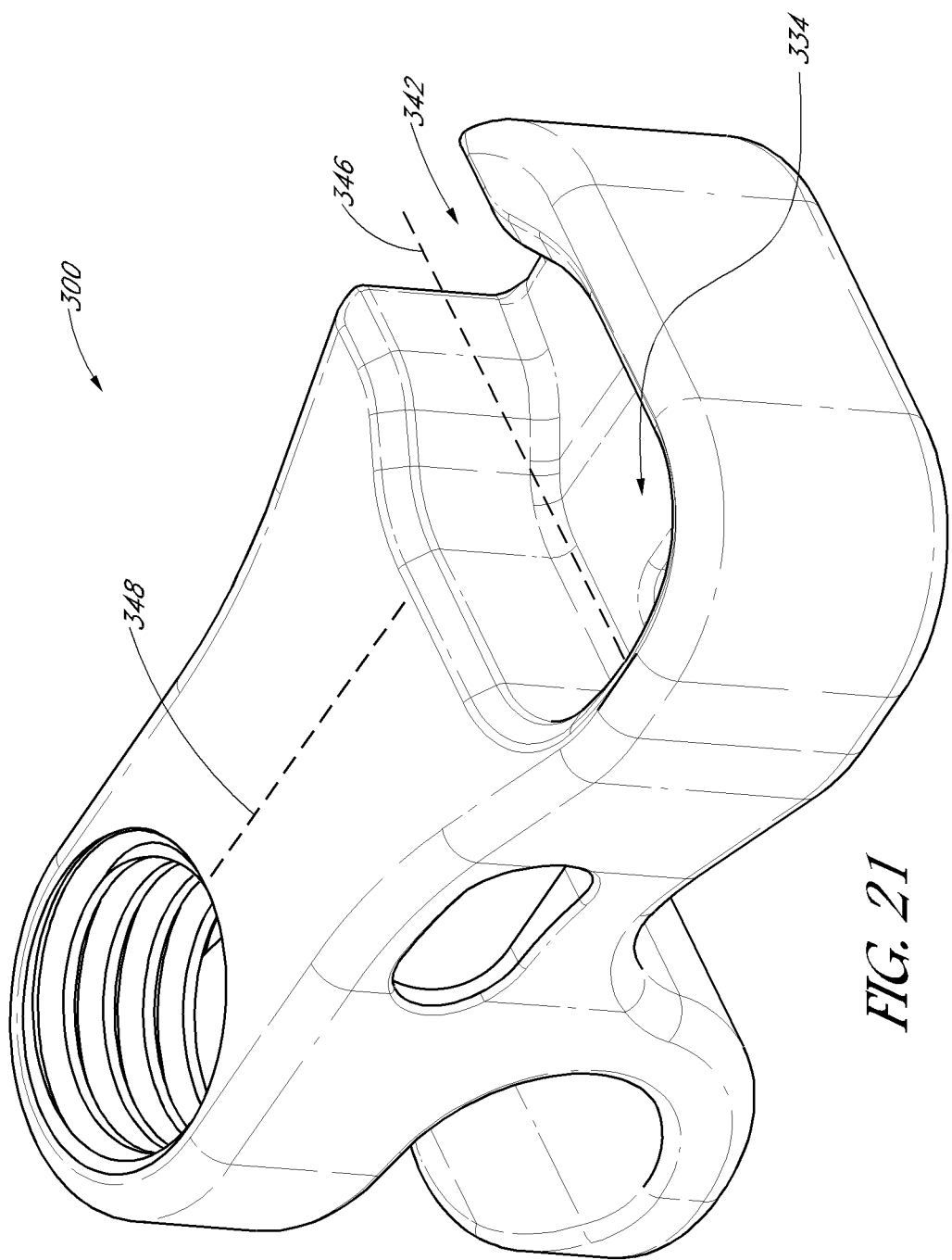
FIG. 21 is a perspective view of a flexible fastening band connector according to an embodiment.
Figure 22:
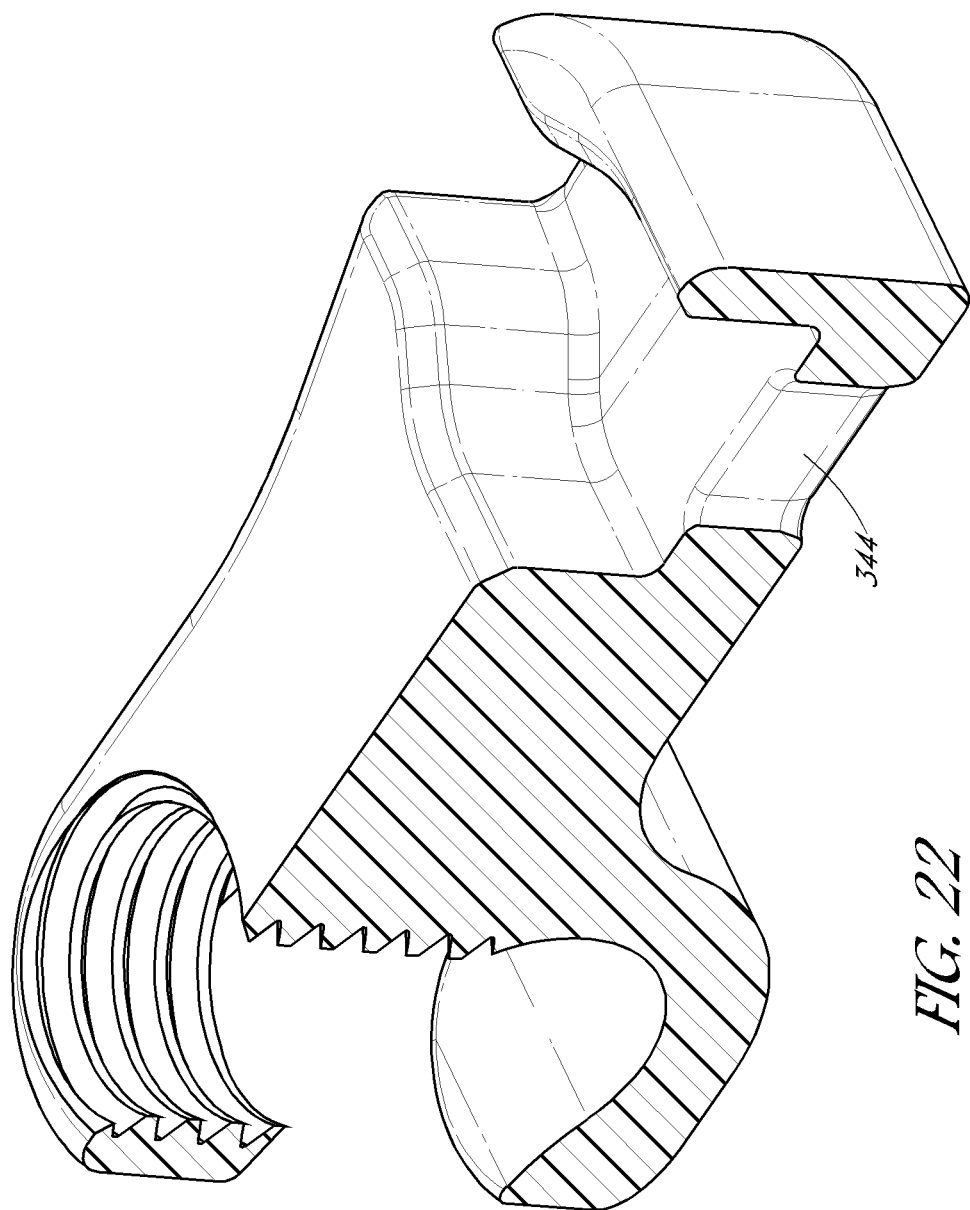
FIG. 22 is a cross-sectional view the flexible fastening band connector depicted in FIG. 21.

FIGS. 21-22 depict a modified position of recess 334. When viewed from the distal end of the connector 300 (as shown in FIG. 21), the opening 342 is on the right side of the second portion 318. The opening 342 shown in FIG. 21 is approximately 180° relative to opening 342 shown in FIG. 19. In the illustrated embodiment, the longitudinal axis 346 of the recess 334 is angled relative to the longitudinal axis 348 of the connector 300. As mentioned herein, the recess 334 can be at any angle relative to the longitudinal axis. In the illustrated embodiment, the longitudinal axis 346 of the recess 334 is perpendicular or substantially perpendicular relative to the longitudinal axis 348 of the connector 300.

Figure 23:
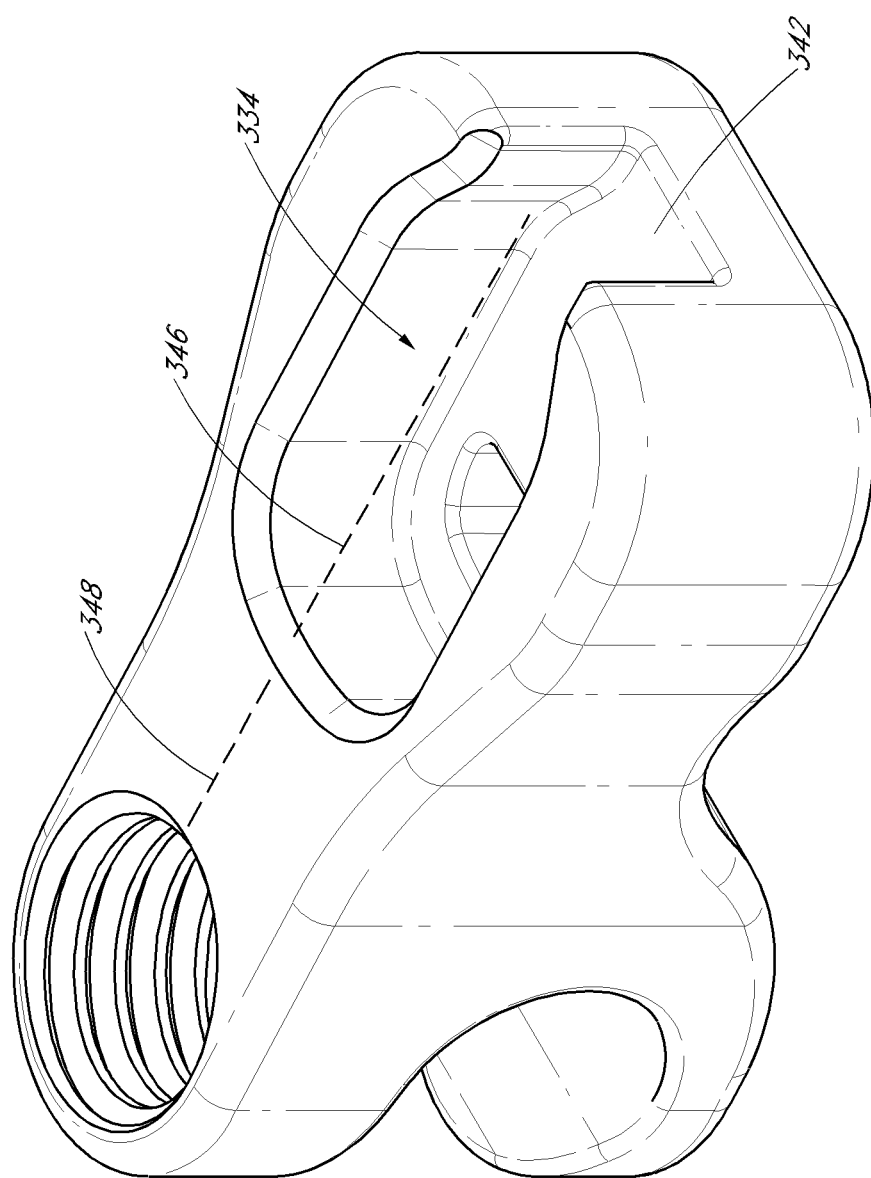
FIG. 23 is a perspective view of a flexible fastening band connector according to an embodiment.
Figure 24:
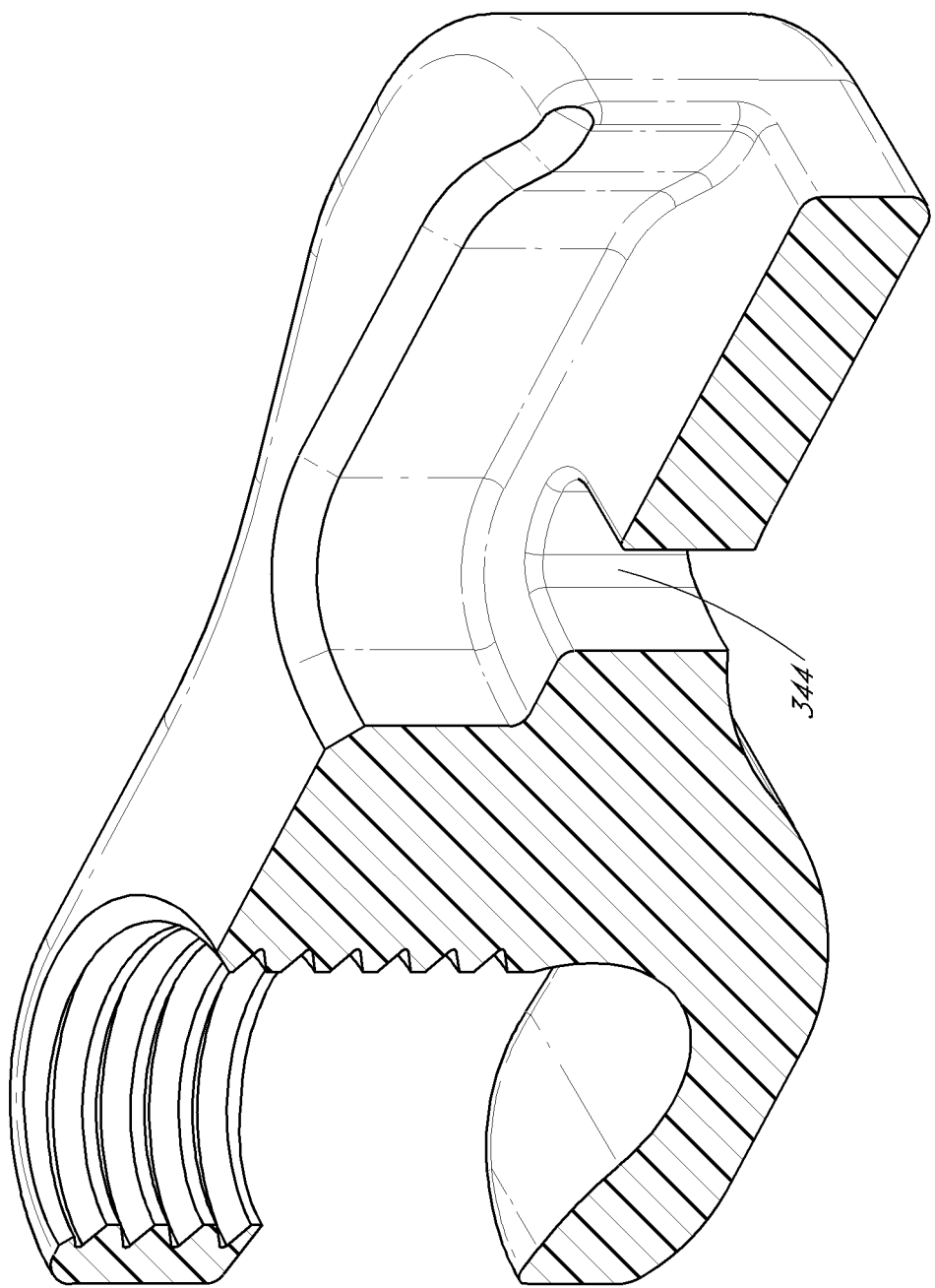
FIG. 24 is a cross-sectional view the flexible fastening band connector depicted in FIG. 23.

FIGS. 23-24 depict another modified position of recess 334. When viewed from the distal end of the connector 300 (as shown in FIG. 21), the opening 342 is on the front of the second portion 318. The opening 342 shown in FIG. 23 is approximately 90° relative to the opening 342 shown in FIG. 19 and approximately 90° relative to the opening 342 shown in FIG. 21. In some such embodiments, the longitudinal axis 346 of the recess 334 and the longitudinal axis 348 of the connector 300 may be substantially coplanar with one another. Indeed in some embodiments, the longitudinal axis 346 of the recess 334 and the longitudinal axis 348 of the connector 300 are substantially parallel to one another. In some such embodiments, the longitudinal axis 346 of the recess 334 and the longitudinal axis 348 of the connector 300 may be substantially coaxial with one another. In particular embodiments, the longitudinal axis 346 of the recess 334 and the longitudinal axis 348 of the connector 300 are coplanar with, parallel to, or at some pre-determined skew angle with respect to one another.

In some embodiments, the connector 300 has more than one recess 334 for receiving the distal end portions 148 of multiple bands 140. The recesses 334 can be in the same orientation or can be oriented in different directions. For example, the connector can have two recesses 334 that are both oriented with the openings 342 facing toward the distal end of the connector 300. In another example, when viewed from the distal end of the connector 300 (as shown in FIG. 21), a first opening of a first recess can face to the right and a second opening of a second recess can face to the left, such that the first opening and the second opening are approximately 180° relative to each other. Other orientations (e.g., angles) between recesses are also contemplated. A plurality of different positions of the recesses are also contemplated, such as a first recess extending into the top surface of the connector and a second recess extending into the bottom surface of the connector.

Figure 25:
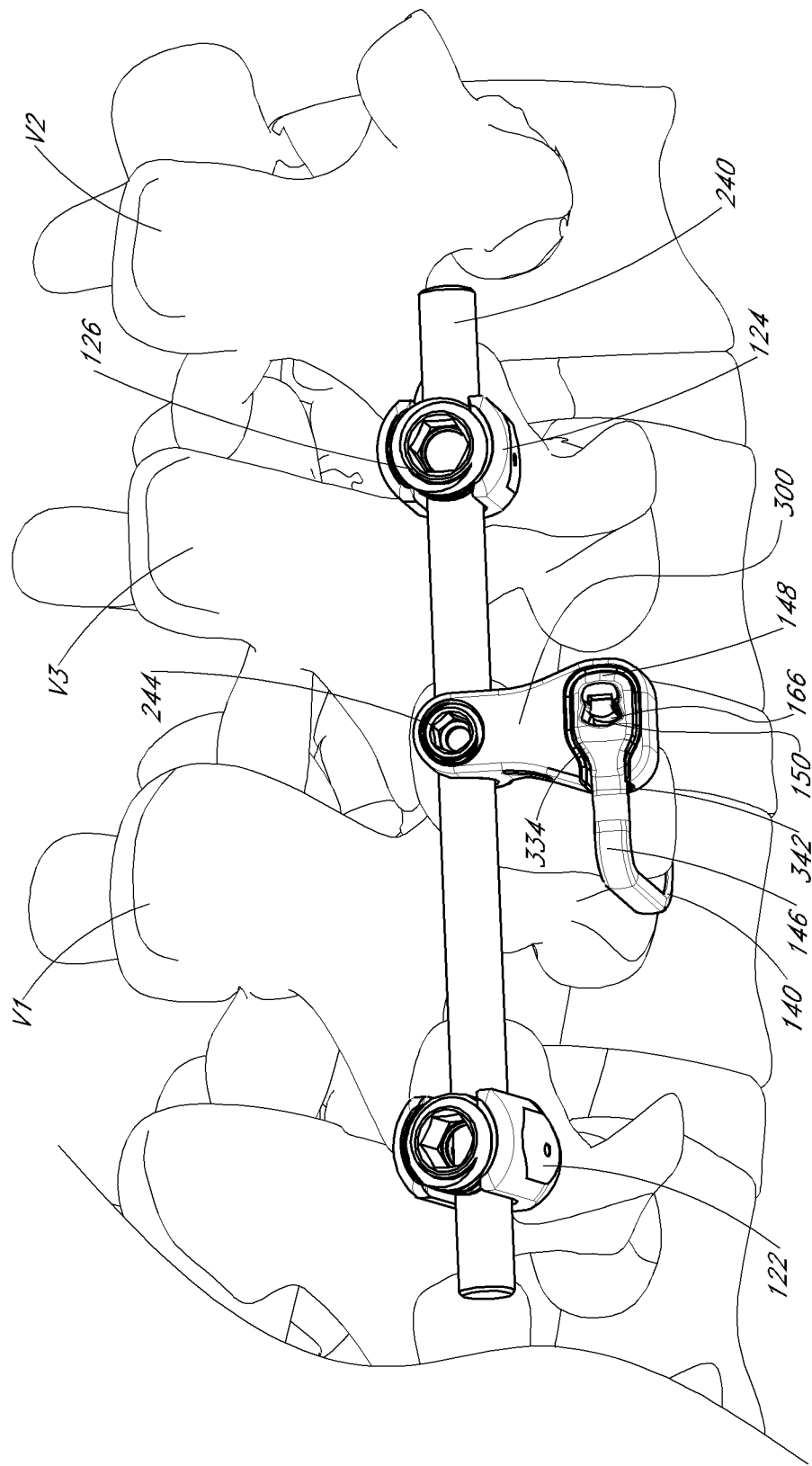
FIG. 25 is a perspective view of the portion of the vertebral column including the flexible fastening band connector depicted in FIG. 19.

FIG. 25 shows a method of use of the connector 300 of FIG. 19. In the illustrated embodiment, the band 140 and the spinal rod 240 can stabilize a first vertebra and/or a second vertebra, and/or can be configured to define a distraction between the first vertebra and the second vertebra. In some uses, the spinal rod 240 can stabilize the first vertebra to a second vertebra (e.g., by securing a pedicle of the first vertebra to a pedicle of a second vertebra) and the band 140 can connect to a transverse process (see, e.g., FIGS. 25-26). In some uses, the spinal rod 240 can stabilize the first vertebra to a second vertebra and the band 140 can connect to a lamina (see, e.g., FIGS. 27-29). In some uses, the spinal rod 240 can stabilize the first vertebra to a second vertebra and the band 140 can connect to a spinous process (see, e.g., FIGS. 30-31). In some uses, the spinal rod 240 can stabilize the first vertebra to a second vertebra and the band 140 can be inserted into a lumen through the superior articular process and the inferior articular process (not shown).

In some uses, the spinal rod 240 is a cylindrically or substantially cylindrical elongate member. For instance, the cross-sectional of the spinal rod 240 can be any appropriate shape, including but not limited to circular, oval, elliptical, rectangular, square, triangular, and polygonal. In some uses, the spinal rod 240 is a plate or plate like.

The spinal rod 240 can be part of a larger support member 120. In the illustrated embodiment, the support member 120 can include pedicle screws, as described herein. The support member can be any apparatus configured to be coupled to one or more bone portions. Examples of alternative support members are shown and described in U.S. patent application Ser. No. 13/804,521; filed Mar. 14, 2013, and titled "Apparatus for Bone Stabilization and Distraction and Methods of Use," which is incorporated herein by reference in its entirety.

In some methods of use, the band 140 can be placed into a suitable position. FIG. 25 shows the band 140 encircling a transverse process. The connector 300 is similar to the connector shown in FIG. 19, with the longitudinal axis 346 of the recess 334 perpendicular or substantially perpendicular to the longitudinal axis 348 of the connector 300. The distal end portion 148 of the band 140 can be positioned within the connector 300. The distal end portion 148 can be inserted into the recess 334. The first portion 144 can extend through the opening 342.

Figure 26:
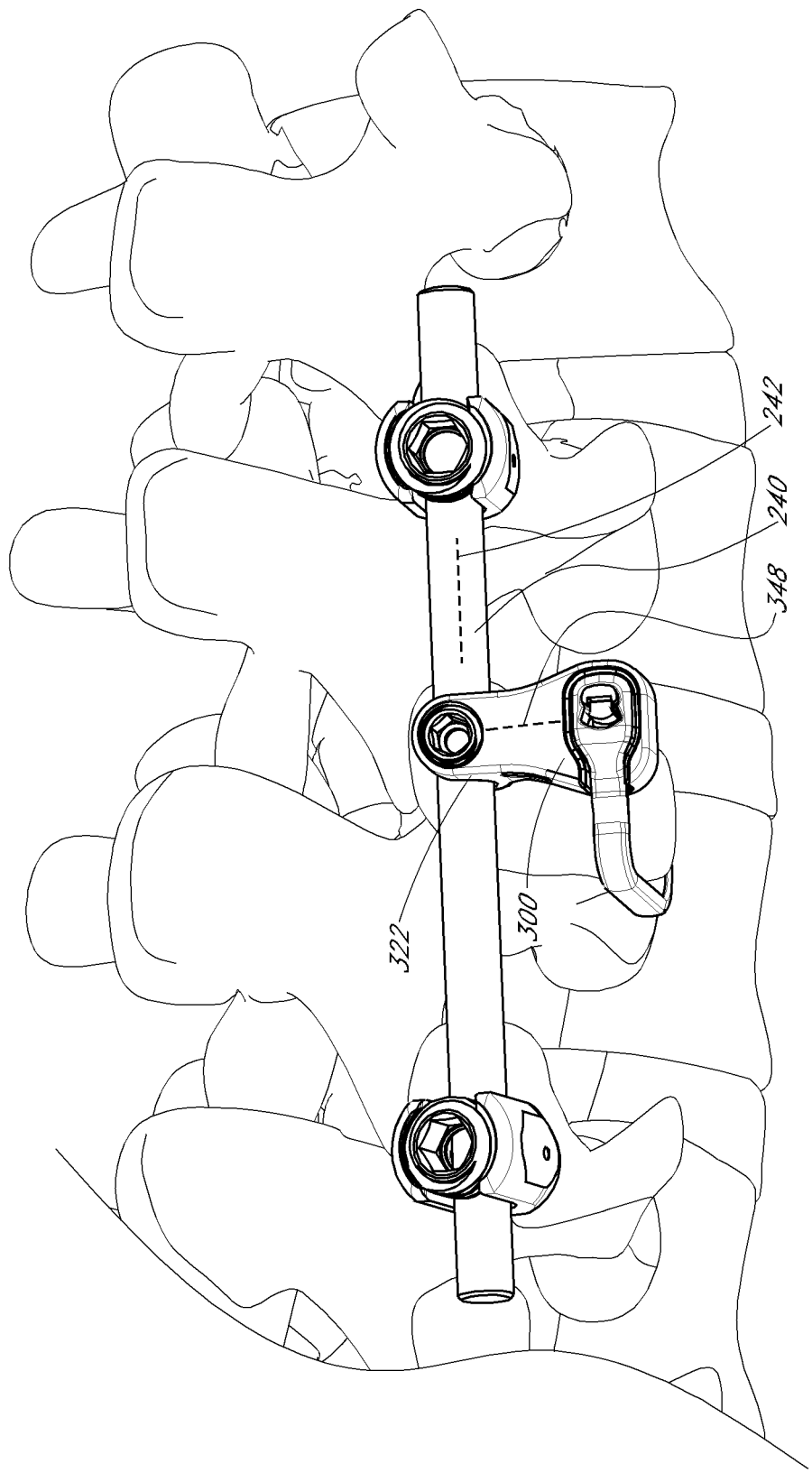
FIG. 26 is a perspective view of the portion of the vertebral column including the flexible fastening band connector depicted in FIG. 25.

The first portion 144 and/or the second portion 146 can encircle one or more bone portions. For example, in some embodiments, the band 140 can be disposed about a transverse process of a vertebra, as shown in FIGS. 25-26. The band 140 can be used in any suitable procedure to stabilize and/or fixate a bone portion. The band 140 can engage a transverse process of a third vertebra, wherein the third vertebra is disposed between the first vertebra and the second vertebra.

Once positioned relative to the bone, the band 140 can be secured. The proximal end portion 142 can be positioned within the lumen 344 of the connector 300. The connector 300 guides the proximal end portion 142 in the correct orientation relative to the distal end portion 148. In some embodiments, the proximal end portion 142 is perpendicular or substantially perpendicular to the distal end portion 148 during insertion of the proximal end portion 142 in the fastening mechanism 150. The proximal end portion 142 can extend through the lumen 166 of the fastener mechanism 150 such that the band 140 forms a loop of suitable tightness about the third bone portion.

The band 140 can be tightened by passing the proximal end portion 142 into the distal end portion 148 and advancing the proximal end portion 142 through the lumen of the fastener member 150 such that the first portion 144 and/or second portion 146 substantially encircles a portion of the vertebra, for instance the transverse process shown in FIGS. 25-26. Similarly stated, the proximal end portion 142 can be inserted in to the lumen of the fastener mechanism 150 such that the band 140 forms a loop about a portion of vertebra. In this manner, the proximal end portion 142, the first portion 144 and/or the second portion 146 can be advanced through the lumen of the fastener mechanism 150 such that the volume disposed within the loop formed by the band 140 is reduced. Thus, the band 140 exerts a compressive force on the bone portion of the vertebra that it encircles. In some methods of use, the band 140 is at least partially tightened or fully tightened around the bone portion prior to placement of the spinal rod 240. In other embodiments, the spinal rod 240 is secured prior to using the band 140 to encircle a portion of the vertebra.

In some methods, a spinal rod 240 of a support member 120 can be fixed to one or more bone portions. In the illustrated embodiment, the support member 120 is coupled to the pedicles of a first vertebra and a second vertebra. In some embodiments, the support member 120 is coupled to the other portions of the spine (e.g., lamina, transverse processes, spinous processes, facets, vertebral body, etc.). In the illustrated embodiment, the support member 120 comprises one or more fasteners 122. In some embodiments, the fasteners 122 are pedicle screws. The fasteners 122 may be polyaxial screws. The fasteners 122 can be coupled to u-shaped yokes 124. The yokes 124 can include a slot sized to accept spinal rod 240. The yokes 124 can be threaded to receive a locking mechanism 126. The locking mechanism 126 applies a force to the spinal rod 240 to seat the spinal rod 240 within the yoke 124. In the illustrated embodiment, the locking mechanism 126 is a set screw, but other locking mechanisms are contemplated.

In some methods, fixing the support member 120 to a bone portion can include advancing a pedicle screw 122 through the yoke 124 and into a first bone portion. For instance, a first pedicle screw 122 can be advanced through a yoke 124 and into a pedicle of a first vertebra. A locking mechanism 126 can be advanced through a yoke 124 to secure the spinal rod 240. A second pedicle screw 122 can be advanced through a yoke 124 and into a pedicle of a second vertebra. The spinal rod 240 can be placed within the yokes 124. A locking mechanism 126 can be advanced through a yoke 124 to secure the spinal rod 240.

The first yoke 124 and the second yoke 124 can be spaced apart to define a distraction distance between the first bone portion and the second bone portion to define a corresponding distraction distance between a first vertebra and a second vertebra. In this manner, the distance between the first yoke 124 and the second yoke 124, e.g., the distance between the first bone portion and the second bone portion, can be increased (or decreased) to increase (or decrease) the distraction between the first vertebra and the second vertebra. The locking mechanism 126 can be advanced to apply a force on the spinal rod 240. The locking mechanisms 126 can maintain the distraction of the first vertebra and the second vertebra. In some methods of use, the locking mechanisms 126 are at least partially tightened or fully tightened onto the spinal rod 240 prior to placement of the spinal rod 240 within the opening 322 of the connector 300. In other embodiments, the spinal rod 240 is placed within the opening 322 of the connector 300 prior to tightening the one or more locking mechanisms 126.

The spinal rod 240 can be positioned within the opening 322 of the connector 300. A locking mechanism 244 is inserted into the threaded bore 330. In the illustrated embodiment, the locking mechanism 244 is a set screw, but other locking mechanisms are contemplated. Further advancement of the locking mechanism 244 will apply a force to the spinal rod 240 and seat the spinal rod 240 within the connector 300. In some methods of use, the locking mechanism 244 is at least partially tightened or fully tightened prior to placement of the spinal rod 240 within the yokes 124. In some methods of use, locking mechanism 244 is at least partially tightened or fully tightened prior to placement of the band 140 within the recess 334.

Figure 27:
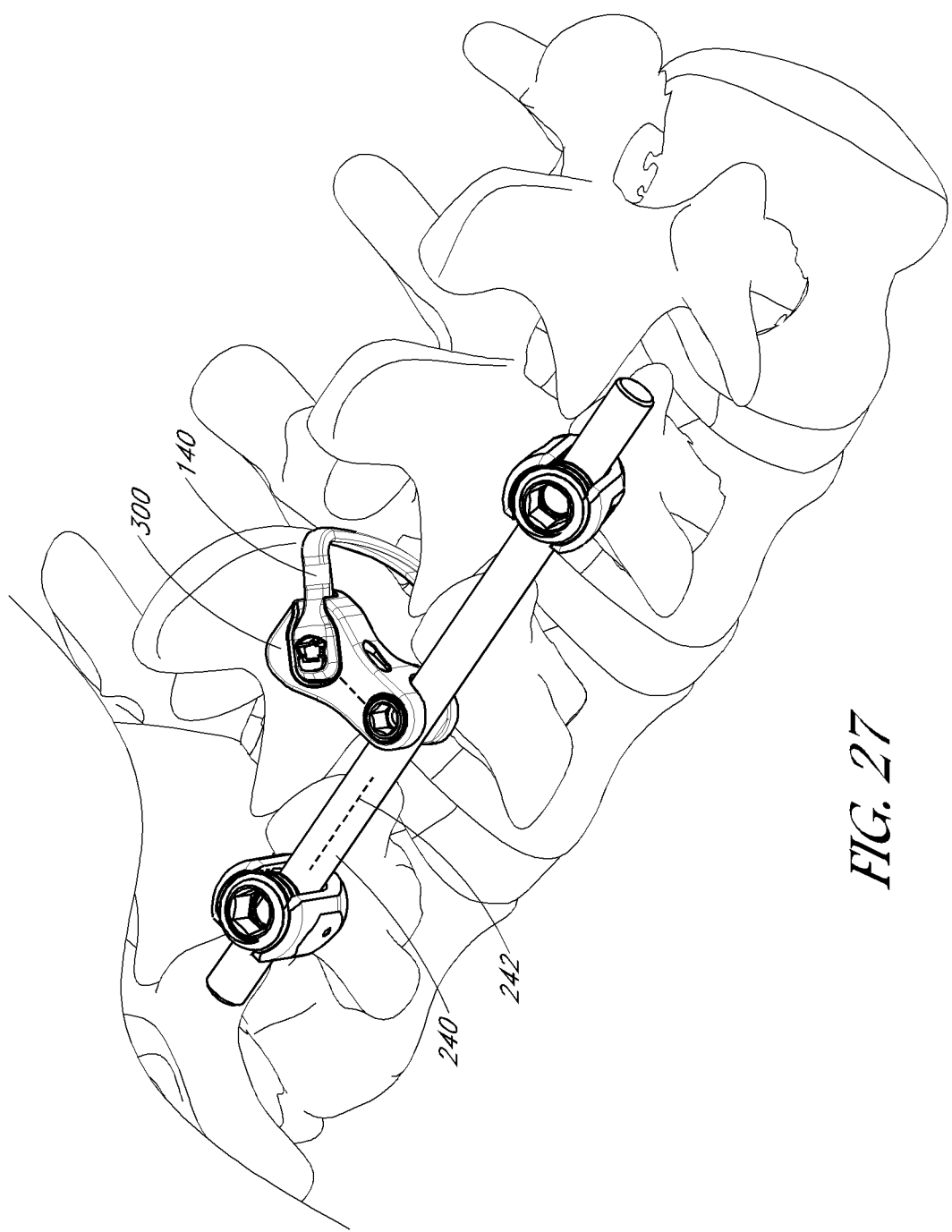
FIG. 27 is a perspective view of the portion of the vertebral column including a flexible fastening band connector according to an embodiment.
Figure 28:
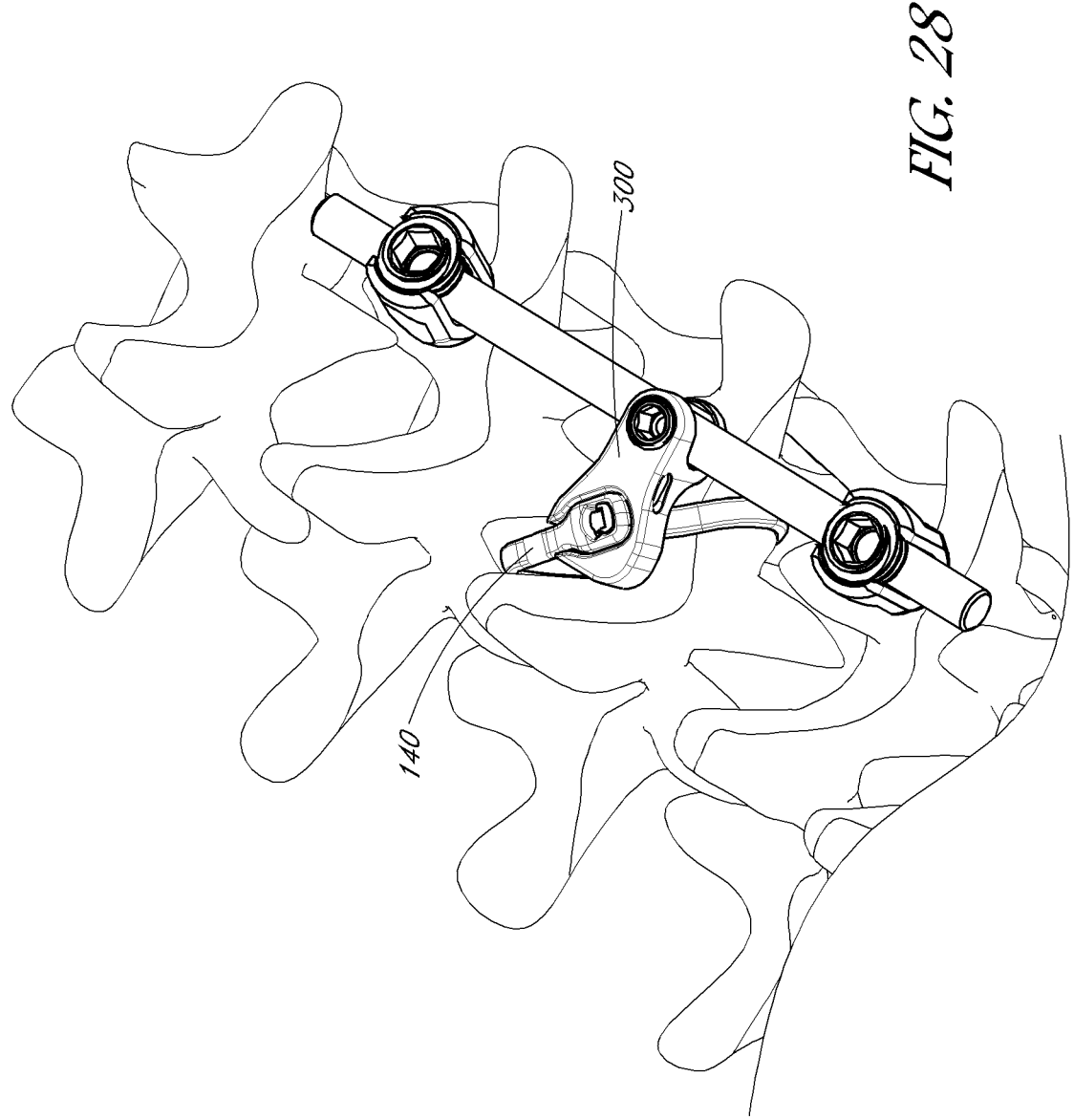
FIG. 28 is another perspective view of the flexible fastening band connector of FIG. 27.
Figure 29:
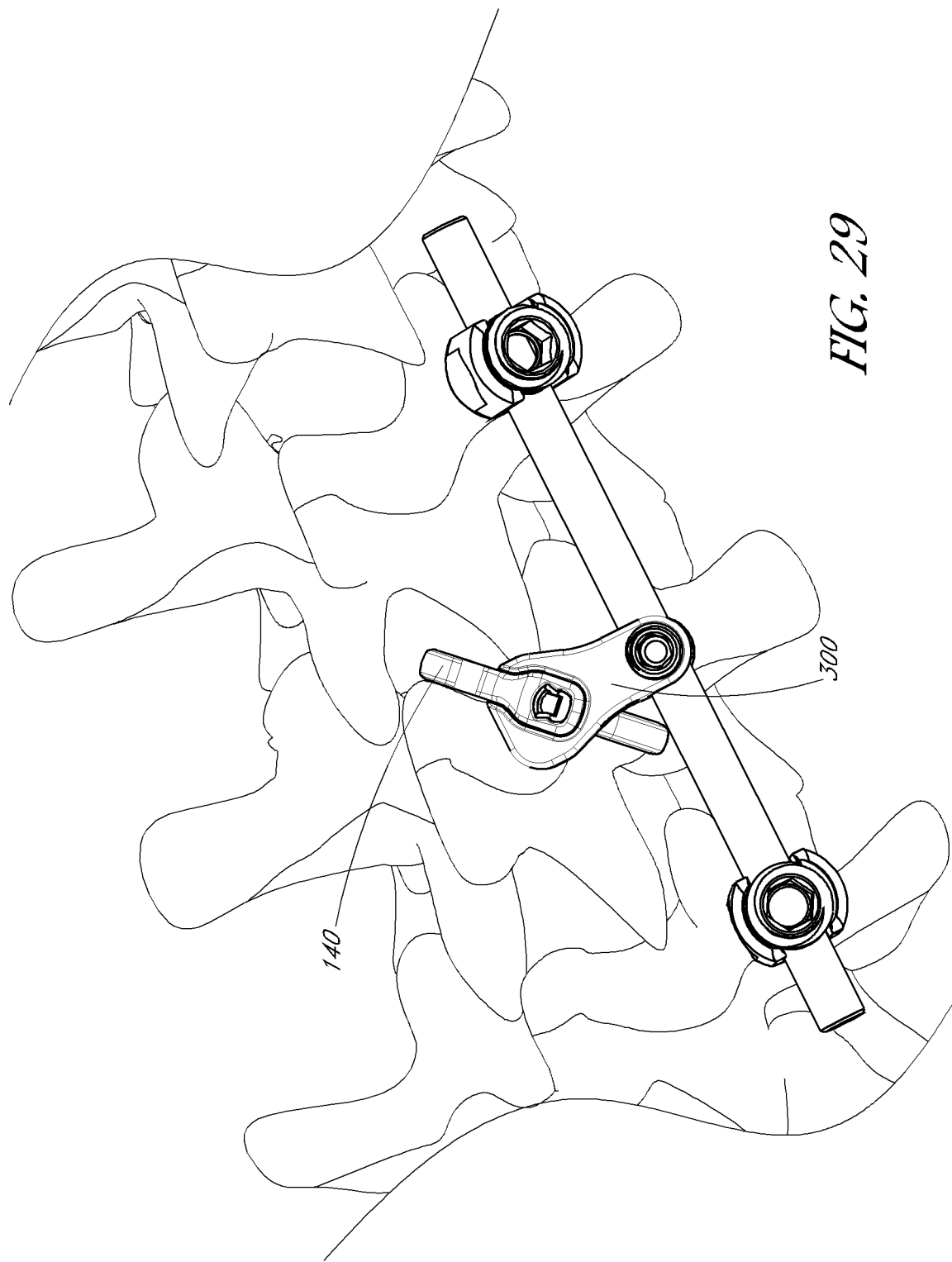
FIG. 29 is another perspective view of the flexible fastening band connector of FIG. 27.

FIGS. 27-29 show a method of use of the connector 300. The connector 300 is similar to the connector shown in FIG. 19, with the longitudinal axis 346 of the recess 334 angled relative to the longitudinal axis 348 of the connector 300. In the illustrated embodiment, the longitudinal axis 346 of the recess 334 is angled relative to the longitudinal axis 348 of the connector 300. For instance, the longitudinal axis 346 of the recess 334 can be at any angle relative to the longitudinal axis 348 of the connector 300. In the illustrated embodiment, the longitudinal axis 346 of the recess 334 is approximately 45° relative to the longitudinal axis 348 of the connector 300. In some uses, the spinal rod 240 can stabilize the first vertebra to a second vertebra by securing a pedicle of the first vertebra to a pedicle of a second vertebra and the band 140 can connect to a lamina (see, e.g., FIGS. 26-28).

The distal end portion 148 of the band 140 can be positioned within the connector 300. The distal end portion 148 can be inserted into the recess 334. The first portion 144 can extend through the opening 342. In some methods of use, the band 140 can be placed into a suitable position. The first portion 144 and/or the second portion 146 can encircle a bone portion. For example, in some embodiments, the band 140 can be disposed about a lamina of a vertebra, as shown in FIGS. 26-28. The band 140 can engage a lamina of a third vertebra, wherein the third vertebra is disposed between the first vertebra and the second vertebra.

Figure 30:
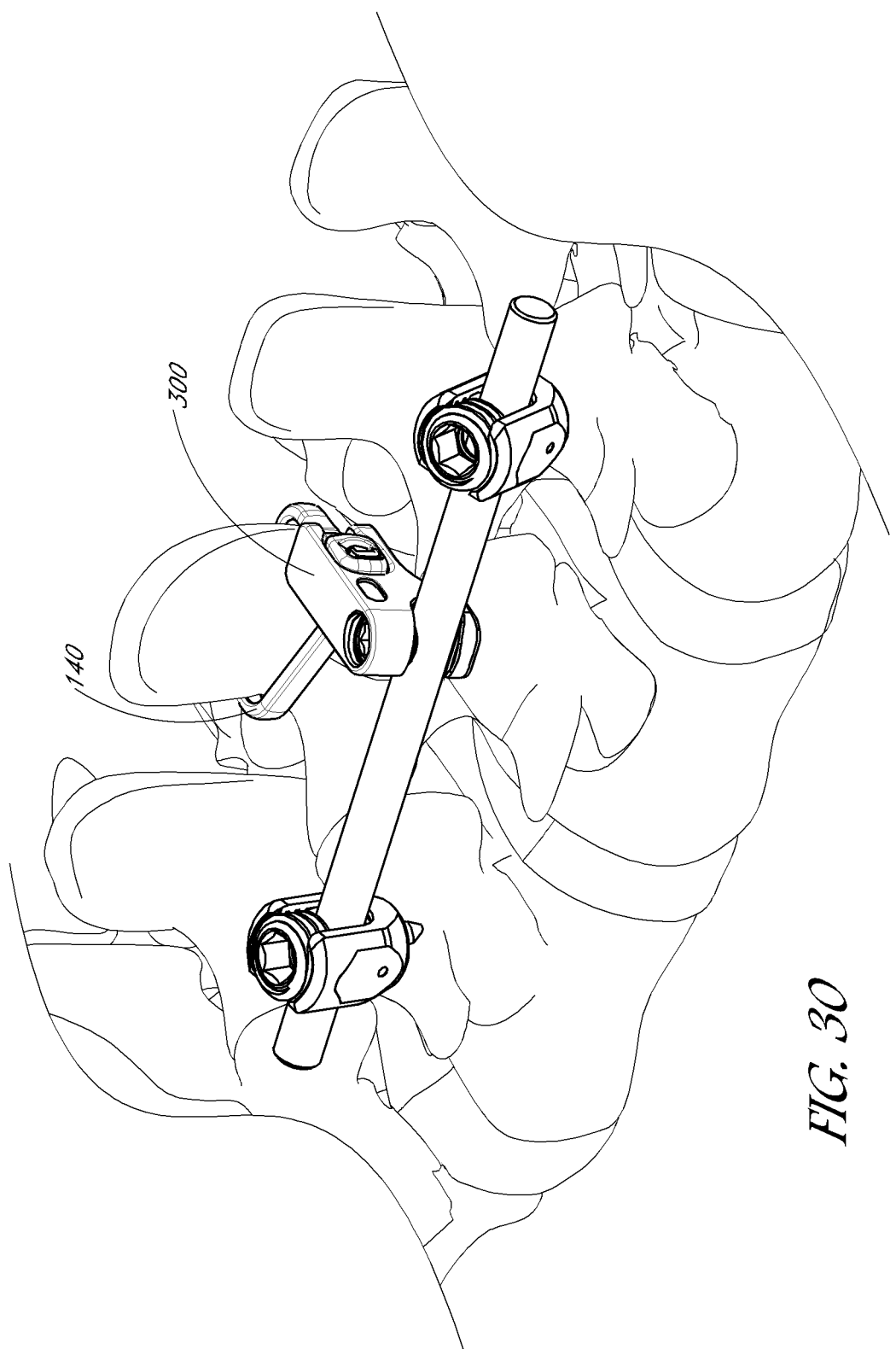
FIG. 30 is a perspective view of the portion of the vertebral column including a flexible fastening band connector according to an embodiment.

FIG. 30 shows a method of use of the connector 300. In the illustrated embodiment, the longitudinal axis 346 of the recess 334 is parallel or substantially parallel to the longitudinal axis 348 of the connector 300. However, unlike the embodiment of FIGS. 23-24, the recess 334 is disposed on the side surface of the connector 300. For instance, the distal end portion 148 is lowered into the recess 334 from the top surface of the connector 300 toward the bottom surface of the connector 300 in FIGS. 23-24. In FIG. 30, the distal end portion 148 is slid into the recess 34 from the side surface of the connector 300 toward the other side surface of the connector 300. In the illustrated embodiment, the side surface also includes the engagement features 332.

Figure 31:
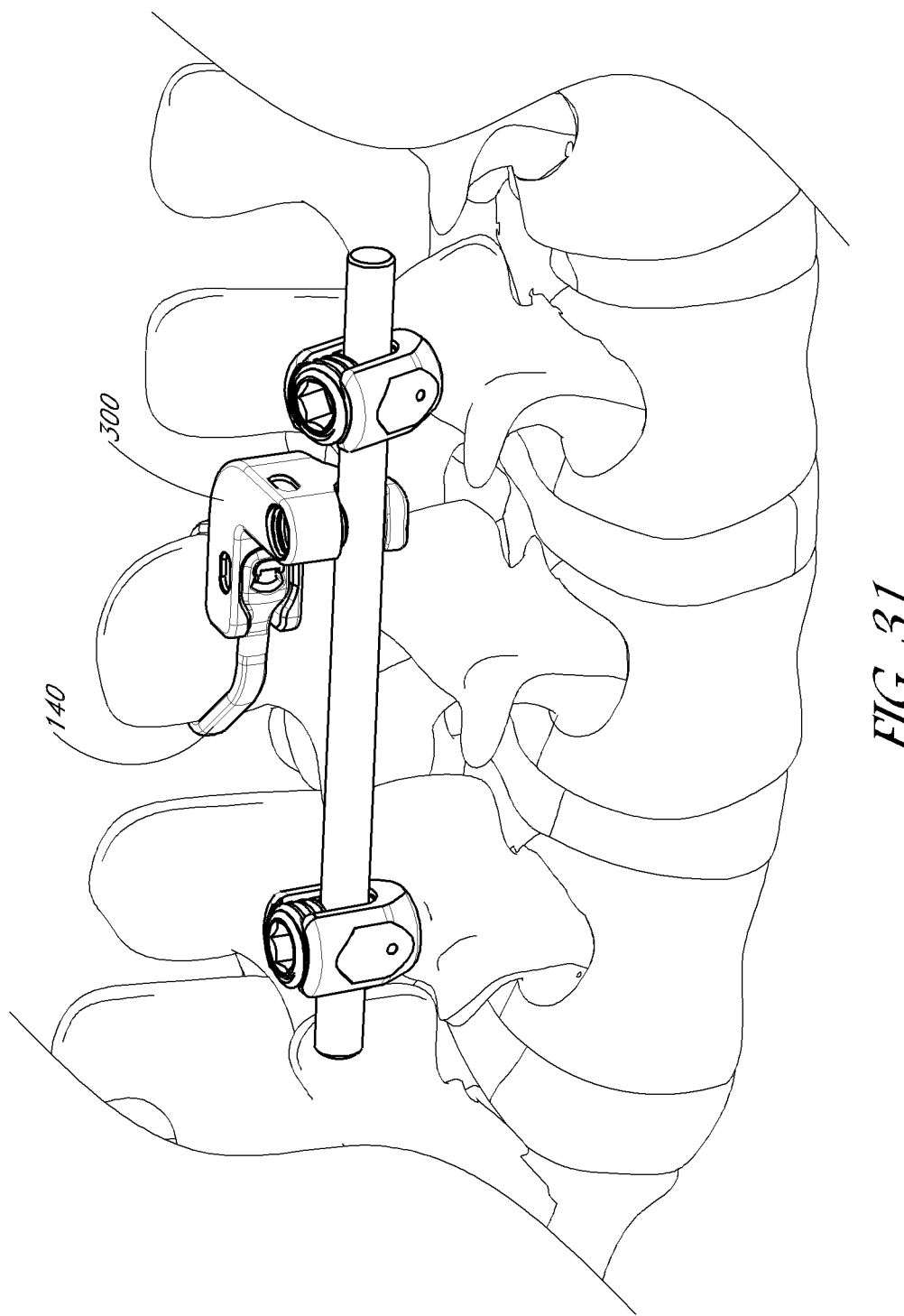
FIG. 31 is a perspective view of the portion of the vertebral column including a flexible fastening band connector according to an embodiment.

FIG. 31 shows one method of use of the connector 300. The connector 300 of FIG. 31 has a L-shaped configuration. Like the embodiment of FIG. 30, the recess 334 is disposed on the side of the connector 300. For instance, the distal end portion 148 is lowered into the recess 334 from the top surface of the connector 300 toward the middle of the connector 300 in FIGS. 23-24. In FIG. 31, the distal end portion 148 is slid into the recess 334 from the side surface of the connector 300 toward the other side surface of the connector 300.

In some methods of use, the band 140 can be placed into a suitable position. FIGS. 30-31 show the band 140 encircling a spinous process of a vertebra. The distal end portion 148 of the band 140 can be positioned within the connector 300. The distal end portion 148 can be inserted into the recess 334. The first portion 144 can extend through the opening 342. The first portion 144 and/or the second portion 146 can encircle a bone portion. For example, in some embodiments, the band 140 can be disposed about a spinous process of a vertebra, as shown in FIGS. 30-31. The band 140 can engage a spinous process of a third vertebra, wherein the third vertebra is disposed between the first vertebra and the second vertebra.

Figure 32:
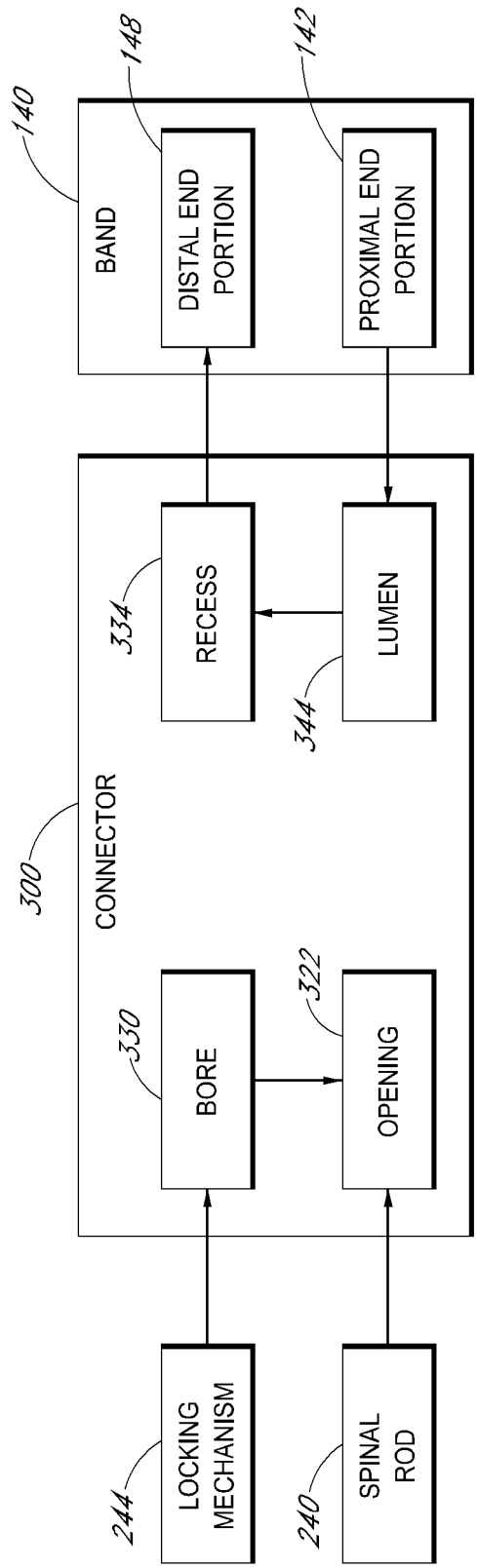
FIG. 32 is a block diagram of a bone stabilization and distraction system according to an embodiment.

FIG. 32 depicts a block diagram of an embodiment of the flexible fastening band connector ("connector") 300 and the flexible fastening band ("band") 140. The connector 300 can include a bore 330 in communication with an opening 322. The bore 330 is sized to receive a locking mechanism 244. The opening 322 is sized to receive a spinal rod 240. The locking mechanism 244 extends through the bore 330 into the opening 322 and into contact with the spinal rod 240 disposed within the opening 322. The connector 300 can include recess 334 in communication with a lumen 344. The recess 334 is sized to receive the distal end portion 148 of a band 140. The lumen 344 is sized to receive the proximal end portion 142 of the band 140. The proximal end portion 142 of the band 140 extends through the lumen 344 into the recess 334 and into contact with the distal end portion 148 disposed within the recess 334.

Figure 33:
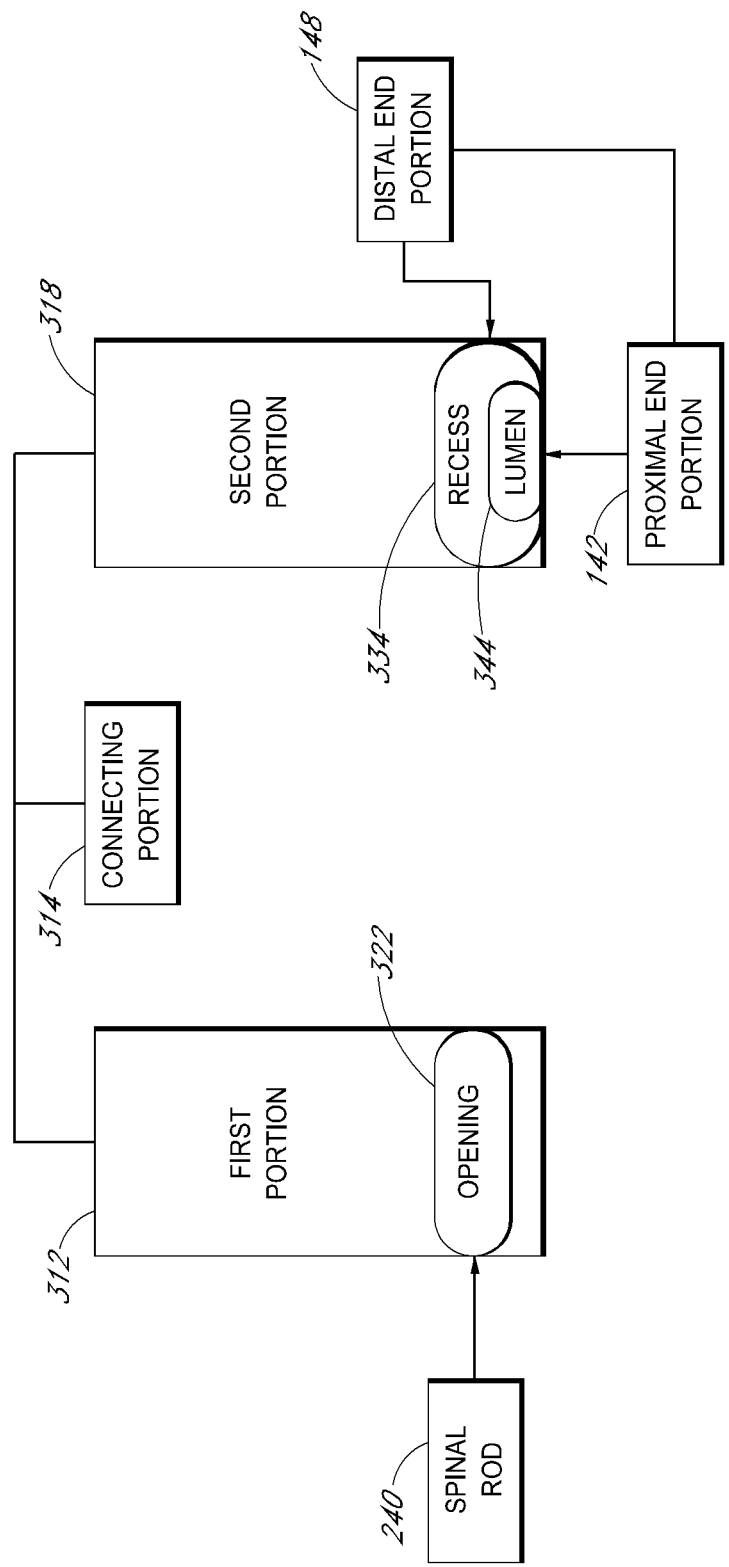
FIG. 33 is a block diagram of a bone stabilization and distraction system according to an embodiment.

FIG. 33 depicts a block diagram of an embodiment of the flexible fastening band connector ("connector") 300 and the flexible fastening band ("band") 140. The connector 300 can include the first portion 312, the connecting portion 314, and the second portion 318. The first portion 312, the connecting portion 314, and the second portion 318 can form a unitary structure. The first portion 312 can include an opening 322 sized to receive a spinal rod 240. The second portion 318 can include a recess 334 sized to receive a distal end portion 148 of a band 140. The second portion 318 can include a lumen 344 sized to receive a proximal end portion 142 of a band 140. The distal end portion 148 and the proximal end portion 142 can form a unitary structure.

In some uses, the spinal rod 240 can stabilize the first vertebra to a second vertebra and the band 140 can be inserted into lumen between one or more bone portions (e.g., the superior articular process and the inferior articular process). The method of forming an artificial lumen is shown and described in U.S. patent application Ser. No. 13/033,791; filed Feb. 24, 2011, and titled "Methods and Apparatus for Stabilizing Bone," U.S. patent application Ser. No. 13/403,698; filed Feb. 23, 2012, and titled "Vertebral Facet Joint Fusion Implant and Method for Fusion," which are incorporated herein by reference in their entirety.

In some embodiments, the band can include a spacer (not shown). The spacer can be similar to, and have similar features to the embodiments of the prosthesis shown and described in U.S. patent application Ser. No. 12/859,009; filed Aug. 18, 2010, and U.S. Provisional Application 61/883,911, filed Sep. 27, 2013, and are incorporated herein by reference in their entirety. As described in the '009 patent, the spacer can be implanted and deployed to restore the space between facets of a superior articular process of a first vertebra and an inferior articular process of an adjacent vertebra. As described herein, the spacer can be implanted and deployed to help stabilize adjacent vertebrae with adhesives, and/or can be implanted and deployed to deliver a medication. For example, in some embodiments, the spacer can be at least temporarily maintained in a desired position via an adhesive while the band 140 is positioned relative to the first vertebra and/or second vertebra. In some embodiments, an adhesive can be used in conjunction with the band 240 to stabilize and/or fixate the first vertebra to the second vertebra. In some embodiments, the band can be used in combination with a plate (not shown). The plate can be similar to, and have similar features to the embodiments of the plates shown and described in and U.S. Provisional Application 61/883,960, filed Sep. 27, 2013, which is incorporated herein by reference in its entirety.

In such embodiments, the spacer can be, for example, substantially disc shaped. In other embodiments, the spacer can be other shapes, e.g., square, elliptical, or any other shape. The spacer can include a first side and a second side. The first side and/or the second side can be, for example, convex, concave, or flat. Said another way, the first side of the spacer can be concave, convex, or flat, and the second side of the spacer can be concave, convex, or flat, for example, the first side can be concave and the second side concave, the first side can be concave and the second side convex, etc. The spacer can include the same materials as band 140. In some embodiments, the spacer can include substances configured to release medication and/or increase the stability of a vertebra and/or band 140. As discussed above, the substances can include a medicine(s) and/or an adhesive(s).

The method of use can include one or more of the following steps in any order: couple a first fastener to a first bone portion; advance a first fastener through a first yoke and into a first bone portion; advance a first locking mechanism into the first yoke to secure a spinal rod to the first yoke; and/or couple a first bone fastener to a spinal rod. The method of use can include one or more of the following steps in any order: couple a second fastener to a second bone portion; advance a second fastener through a second yoke and into a second bone portion; advance a second locking mechanism into the second yoke to secure a spinal rod to the second yoke; and/or couple a second bone fastener to a spinal rod. The method of use can include one or more of the following steps in any order: distract the first bone portion from the second bone portion; fix a distance between the first bone portion and the second bone portion; move the first bone portion relative to the second bone portion; increase the distraction distance between a first bone portion and a second bone portion and/or decrease the distraction distance between a first bone portion and a second bone portion.

The method of use can include one or more of the following steps in any order: insert the spinal rod into a connector; slide a spinal rod from a proximal end toward a distal end of the connector, seat the spinal rod within an opening of the connector; retain the spinal rod within the opening with at least one lip portion; and/or advance a locking mechanism to secure a spinal rod to the connector.

The method of use can include one or more of the following steps in any order: insert a flexible fastening band into the connector; lower the flexible fastening band into a recess of the connector; lower the flexible fastening band from a top surface of the connector toward a bottom surface of the connector; slide the flexible fastening band into a recess of the connector; slide the flexible fastening band from a side surface of the connector toward an opposed side surface of the connector; place the distal end portion of the flexible fastening band within a recess of the connector; and/or abut the distal end portion of the flexible fastening band with a surface of the recess of the connector.

The method of use can include one or more of the following steps in any order: insert the flexible fastening band into a lumen between two bone portions; insert the flexible fastening band into a lumen between articular processes; and/or insert the flexible fastening band across the facet joint. The method of use can include one or more of the following steps in any order: encircle a bone portion with the flexible fastening band, encircle a bone portion of a first vertebra and a bone portion of a second vertebra with the flexible fastening band; encircle a spinous process with the flexible fastening band; encircle a transverse process with the flexible fastening band; and/or encircle a lamina with the flexible fastening band.

The method of use can include one or more of the following steps in any order: insert a flexible fastening band into a lumen of the connector; align the lumen of the connector with the lumen of the fastening mechanism; advance the flexible fastening band through the lumen of the connector; advance the flexible fastening band through the fastening mechanism. The method of use can include one or more of the following steps in any order: insert the gears of the flexible fastening band into a lumen of the connector; align the lumen of the connector with the lumen of the fastening mechanism; advance the gears of the flexible fastening band through the fastening mechanism; advance the gears of the flexible fastening band through the ratchet of the fastening mechanism.

While certain embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

Further features of this disclosure are given in the following numbered clauses:

Clause 1. A system comprising:
a band comprising a flexible elongate body including a proximal end portion and a distal end portion, the distal end portion including a fastener having an opening that can receive the proximal end portion of the flexible elongate body;
a connector comprising a first portion for engaging a fixation device, and a second portion with a recess formed on a first side of the connector and a lumen formed on a second side of the connector, the lumen extending to the recess, wherein the recess is configured to receive at least a portion of the fastener of the distal end portion of the flexible elongate body and wherein the lumen is configured to guide the proximal end portion of the flexible elongated body into the opening in the fastener when the fastener is positioned at least partially within the recess.

Clause 2. The system of Clause 1, wherein the first portion of the connector includes an opening configured to accept a spinal rod.

Clause 3. The system of Clause 1, wherein the first side of the connector and the second side of the connector are opposed parallel sides of the connector.

Clause 4. The system of Clause 2, wherein the first portion of the connector includes a locking mechanism configured to apply a force to the spinal rod within the opening.

Clause 5. The system of Clause 1, wherein the first side of the connector is the top of the connector and the second side of the connector is the bottom of the connector.

Clause 6. The system of Clause 1, wherein the first side of the connector is a side surface of the connector and the second side of the connector is the opposed side surface.

Clause 7. The system of Clause 1, wherein a side surface of the recess has a depth equal or greater than a thickness of the distal end portion.

Clause 8. The system of Clause 1, wherein the distal end portion does not protrude from the connector when the distal end portion is disposed in the recess.

Clause 9. The system of Clause 1, wherein the recess is sized to be greater than the distal end portion in all three dimensions.

Clause 10. The system of Clause 1 wherein the recess includes a neck which limits movement of the distal end portion within the recess.

Clause 11. They system Clause 10, wherein the neck aligns the opening of the fastener with the lumen.

Clause 12. The system of Clause 1, wherein a longitudinal axis of the recess forms an angle with a longitudinal axis of the connector.

Clause 13. The system of Clause 12, wherein the angle is approximately 0°.

Clause 14. The system of Clause 12, wherein the angle is approximately 45°.

Clause 15. The system of Clause 12, wherein the angle is approximately 90°.

Clause 16. The system of Clause 1, wherein a longitudinal axis of the recess forms an angle with a longitudinal axis of the lumen.

Clause 17. The system of Clause 16, wherein the angle is approximately 90°.

Clause 18. The system of Clause 1, further comprising one or more pedicle screws configured to couple to the spinal rod.

Clause 19. The system of Clause 1, further comprising a second flexible elongate body configured to couple to the spinal rod.

Clause 20. A spinal fixation device connector comprising:
a body comprising a first portion and a second portion, the first portion of the body including an opening configured to accept a spinal rod, and the second portion having a first side and a second side, a recess formed in the first side of the body configured to receive a distal end portion of a flexible elongate body, wherein the flexible elongate body comprises a proximal end portion and a distal end portion, wherein the distal end portion of the flexible elongate body comprises a fastener configured to accept the proximal end portion; and
a lumen formed on the second side of the body, the lumen intersecting the recess and configured to guide a proximal end portion toward a fastener when the distal end portion of the flexible elongate body is received in the recess.

Clause 21. The connector of Clause 20, further comprising a locking mechanism in communication with the opening, wherein the locking mechanism is configured to apply a force to the spinal rod within the opening.

Clause 22. The connector of Clause 20, wherein a longitudinal axis of the recess forms an angle with a longitudinal axis of the connector.

Clause 23. The connector of Clause 22, wherein the angle is approximately 0°.

Clause 24. The connector of Clause 22, wherein the angle is approximately 45°.

Clause 25. The connector of Clause 22, wherein the angle is approximately 90°.

Clause 26. The connector of Clause 20, further comprising the flexible elongate body.

Clause 27. The connector of Clause 20, wherein a longitudinal axis of the recess forms an angle with a longitudinal axis of the lumen.

Clause 28. The connector of Clause 27, wherein the angle is approximately 90°.

Clause 29. The connector of Clause 20, wherein a longitudinal axis of the recess is substantially perpendicular to a longitudinal axis of the lumen.

Clause 30. The connector of Clause 20, wherein a longitudinal axis of the recess is perpendicular to a longitudinal axis of the lumen.

Clause 31. The connector of Clause 20, wherein a longitudinal axis of the recess is substantially parallel to a longitudinal axis of the spinal rod received within the opening.

Clause 32. The connector of Clause 20, wherein a longitudinal axis of the recess is parallel to a longitudinal axis of the spinal rod received within the opening.

Clause 33. The connector of Clause 20, wherein a longitudinal axis of the lumen is substantially perpendicular to a longitudinal axis of the spinal rod received within the opening.

Clause 34. The connector of Clause 20, wherein a longitudinal axis of the lumen is perpendicular to a longitudinal axis of the spinal rod received within the opening.

Clause 35. The connector of Clause 20, further comprising a bore in communication with the opening, wherein the bore is configured to receive a locking mechanism for securing the spinal rod to the connector.

Clause 36. The connector of Clause 35, wherein a longitudinal axis of the bore is substantially parallel to a longitudinal axis of the lumen.

Clause 37. The connector of Clause 35, wherein a longitudinal axis of the bore is parallel to a longitudinal axis of the lumen.

Clause 38. The connector of Clause 35, wherein a longitudinal axis of the bore is substantially perpendicular to a longitudinal axis of the spinal rod received within the opening.

Clause 39. The connector of Clause 35, wherein a longitudinal axis of the bore is perpendicular to a longitudinal axis of the spinal rod received within the opening.

Clause 40. A method, comprising:
inserting a distal end portion of a flexible elongate body into a recess of a connector, disposing a portion of the flexible elongate body into contact with a first bone portion, inserting a proximal end portion of the flexible elongate body into a lumen of the connector, and
guiding the proximal end portion through the lumen and through a fastener of the distal end portion.

Clause 41. The method of Clause 40, wherein disposing a portion of a flexible elongate body into contact with a first bone portion comprises encircling a first bone portion.

Clause 42. The method of Clause 40, wherein disposing a portion of a flexible elongate body into contact with a first bone portion comprises disposing a portion of the flexible elongate body through an artificial lumen of the first bone portion.

Clause 43. The method of Clause 40, wherein disposing a portion of a flexible elongate body into contact with a first bone portion comprises encircling a spinous process.

Clause 44. The method of Clause 40, wherein disposing a portion of a flexible elongate body into contact with a first bone portion comprises encircling a transverse process.

Clause 45. The method of Clause 40, wherein disposing a portion of a flexible elongate body into contact with a first bone portion comprises encircling a lamina.

Clause 46. The method of Clause 40, further comprising disposing a spinal rod in an opening of the connector.

Clause 47. The method of Clause 46, further comprising securing the spinal rod in the opening of the connector with a locking mechanism.

Clause 48. The method of Clause 46, further comprising securing the spinal rod to one or more vertebra with one or more fasteners.

Clause 49. The method of Clause 46, further comprising securing the spinal rod to one or more vertebra with one or more flexible elongate bodies.

What is claimed is:
1. A method, comprising:
providing a flexible elongate body for positioning relative to a first bone portion, the flexible elongate body comprising a proximal end and a distal end, wherein the distal end of the flexible elongate body comprises an enlarged head defining a fastener and a body portion extending from the enlarged head defining the fastener to the proximal end, wherein the distal end, the body portion, and the proximal end are monolithically formed,
positioning a connector relative to the first bone portion, the connector comprising a top surface, a bottom surface, and a middle surface disposed between the top surface and the bottom surface, wherein the connector comprises a wall extending from the top surface to the middle surface, the wall forming a recess in the connector, wherein the recess is shaped to receive the enlarged head defining the fastener and seat the enlarged head defining the fastener within the connector, wherein the connector comprises a lumen extending from the middle surface to the bottom surface, wherein the connector is disposed between the enlarged head defining the fastener and the first bone portion,
disposing the body portion of the flexible elongate body into contact with the first bone portion,
inserting the proximal end of the flexible elongate body into the lumen of the connector which guides the proximal end of the flexible elongate body toward the enlarged head defining the fastener and inserting the proximal end of the flexible elongate body through the enlarged head defining the fastener; and
inserting the enlarged head defining the fastener into the recess of the connector to seat the enlarged head defining the fastener against the middle surface within the connector such that the wall at least partially encloses the distal end of the flexible elongate body.

2. The method of claim 1, wherein disposing the body portion of the flexible elongate body into contact with the first bone portion comprises encircling the first bone portion.

3. The method of claim 1, wherein disposing the body portion of the flexible elongate body into contact with the first bone portion comprises disposing the body portion of the flexible elongate body through an artificial lumen of the first bone portion.

4. The method of claim 1, further comprising disposing a spinal rod in an opening of the connector.

5. The method of claim 4, further comprising securing the spinal rod in the opening of the connector with a locking mechanism.

6. The method of claim 4, further comprising securing the spinal rod to one or more vertebra with one or more fasteners.

7. The method of claim 4, further comprising securing the spinal rod to one or more vertebra with one or more flexible elongate bodies.

8. The method of claim 1, wherein the flexible elongate body travels through the fastener in only one direction.

9. A method, comprising:
   providing a flexible elongate body for positioning relative to a first bone portion, the flexible elongate body comprising a proximal end and a distal end, wherein the distal end of the flexible elongate body comprises a fastening mechanism configured to receive the proximal end, and the flexible elongate body comprises a body portion extending from the fastening mechanism to the proximal end,
   positioning a connector relative to the first bone portion, the connector comprising a proximal end, a closed distal end, a recess extending from the proximal end of the connector toward the closed distal end of the connector, and a lumen, wherein the recess is sized and shaped to receive the distal end of the flexible elongate body and allow the body portion to extend through the proximal end of the connector when the fastening mechanism is seated within the connector, wherein the lumen is sized and shaped to receive the proximal end of the flexible elongate body, the lumen of the connector positioned closer to the first bone portion than the recess of the connector,
   inserting the proximal end of the flexible elongate body into the lumen of the connector which guides the proximal end of the flexible elongate body toward the fastening mechanism and inserting the proximal end of the flexible elongate body through the fastening mechanism, wherein the proximal end of the flexible elongate body travels through the fastening mechanism in a first direction, thereby tightening the flexible elongate body about the first bone portion, wherein movement of the body portion is limited through the fastening mechanism in a second direction, opposite the first direction; and
   inserting the distal end of the flexible elongate body into the recess of the connector to seat the fastening mechanism within the connector, wherein the closed distal end of the connector is distal to the distal end of the flexible elongate body when the distal end of the flexible elongate body is in the recess.

10. The method of claim 9, further comprising encircling the first bone portion with the flexible elongate body.

11. The method of claim 9, further comprising disposing a portion of the flexible elongate body through an artificial lumen of the first bone portion.

12. The method of claim 9, further comprising disposing a spinal rod in an opening of the connector.

13. The method of claim 12, further comprising securing the spinal rod in the opening of the connector with a locking mechanism.

14. The method of claim 12, further comprising securing the spinal rod to one or more vertebra.

* * * * *